United States Patent
Cortez et al.

(10) Patent No.: US 10,844,068 B2
(45) Date of Patent: *Nov. 24, 2020

(54) COMPOUNDS AND COMPOSITIONS AS TOLL-LIKE RECEPTOR 7 AGONISTS

(71) Applicant: NOVARTIS AG, Basel (CH)

(72) Inventors: Alex Cortez, San Diego, CA (US); Timothy Hoffman, San Diego, CA (US); Yongkai Li, Del Mar, CA (US); Tom Yao-Hsiang Wu, San Diego, CA (US); Xiaoyue Zhang, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/521,211

(22) Filed: Jul. 24, 2019

(65) Prior Publication Data

US 2019/0345166 A1  Nov. 14, 2019

Related U.S. Application Data

(63) Continuation of application No. 15/906,424, filed on Feb. 27, 2018, now Pat. No. 10,407,431, which is a continuation of application No. 15/307,510, filed as application No. PCT/US2015/028285 on Apr. 29, 2015, now Pat. No. 9,944,649.

(60) Provisional application No. 61/987,314, filed on May 1, 2014.

(51) Int. Cl.
| | |
|---|---|
| *A61K 31/519* | (2006.01) |
| *C07D 487/04* | (2006.01) |
| *A61P 17/00* | (2006.01) |
| *A61P 35/00* | (2006.01) |
| *A61P 35/04* | (2006.01) |
| *A61P 29/00* | (2006.01) |
| *A61P 31/00* | (2006.01) |
| *A61P 11/10* | (2006.01) |
| *A61P 11/00* | (2006.01) |

(52) U.S. Cl.
CPC .......... *C07D 487/04* (2013.01); *A61K 31/519* (2013.01); *A61P 11/10* (2018.01); *A61P 17/00* (2018.01); *A61P 29/00* (2018.01); *A61P 31/00* (2018.01); *A61P 35/00* (2018.01); *A61P 35/04* (2018.01)

(58) Field of Classification Search
CPC .............................. C07D 487/04; A61K 31/519
See application file for complete search history.

(56) References Cited

U.S. PATENT DOCUMENTS

| | | | |
|---|---|---|---|
| 2007/0225303 | A1 | 9/2007 | Ogita et al. |
| 2009/0105212 | A1 | 4/2009 | Isobe et al. |
| 2012/0087893 | A1 | 4/2012 | Lahser et al. |
| 2015/0239888 | A1 | 8/2015 | Graupe et al. |
| 2017/0057968 | A1 | 3/2017 | Li et al. |

FOREIGN PATENT DOCUMENTS

| | | |
|---|---|---|
| EP | 0530537 A1 | 10/1993 |
| WO | 1995033752 A1 | 12/1995 |
| WO | 2000068213 A1 | 5/2000 |
| WO | 2005080393 A1 | 9/2005 |
| WO | 2005107760 A1 | 11/2005 |
| WO | 2005118588 A1 | 12/2005 |
| WO | 2006101783 A2 | 9/2006 |
| WO | 2008100565 A | 8/2008 |
| WO | 2009098236 A1 | 8/2009 |
| WO | 2010048149 A2 | 4/2010 |
| WO | 2010080537 A1 | 7/2010 |
| WO | 2011140338 A1 | 11/2011 |
| WO | 2011162515 A2 | 12/2011 |
| WO | 2012066336 A1 | 5/2012 |
| WO | 2013037960 A1 | 3/2013 |
| WO | 2013103931 A1 | 7/2013 |
| WO | 2014056953 A1 | 4/2014 |

OTHER PUBLICATIONS

U.S. Appl. No. 15/906,424.
U.S. Appl. No. 15/307,510.
U.S. Appl. No. 61/987,314.

*Primary Examiner* — Susanna Moore
(74) *Attorney, Agent, or Firm* — Daniel E. Raymond; Novartis Institutes for BioMedical Research, Inc.

(57) ABSTRACT

The invention provides compounds of Formula (I), immunogenic compositions and pharmaceutical compositions comprising such compounds and methods of using such compounds to treat diseases or disorders associated with Toll-Like Receptor 7 activity.

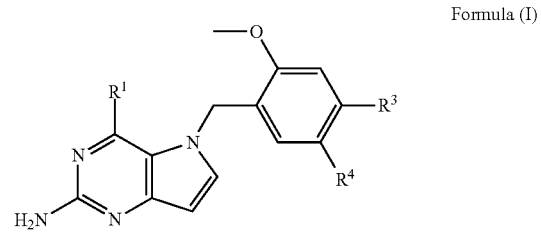

Formula (I)

16 Claims, No Drawings

COMPOUNDS AND COMPOSITIONS AS TOLL-LIKE RECEPTOR 7 AGONISTS

CROSS-REFERENCE TO RELATED APPLICATIONS

This application is a U.S. Continuation Patent Application of U.S. patent application Ser. No. 15/906,424, filed Feb. 27, 2018, which is a U.S. Continuation Patent Application of U.S. patent application Ser. No. 15/307,510, filed Oct. 28, 2016, which is a 371 U.S. national phase application of international application number PCT/US2015/028285 filed 29 Apr. 2015, which application claims the benefit of priority under 35 U.S.C. § 119(e) to U.S. Provisional Patent Application No. 61/987,314, filed 1 May 2014, the disclosures of which are incorporated herein by reference in its entirety and for all purposes.

FIELD OF THE INVENTION

The invention relates to compounds which are Toll-Like Receptor 7 (TLR7) agonists, compositions containing such compounds and methods of using such compounds.

BACKGROUND OF THE INVENTION

Early detection of specific classes of pathogens is accomplished by the innate immune system with the help of pattern recognition receptors (PRRs). The detected pathogens include viruses, bacteria, protozoa and fungi, and each constitutively expresses a set of class-specific, mutation-resistant molecules called pathogen-associated molecular patterns (PAMPs). These molecular markers may be composed of proteins, carbohydrates, lipids, nucleic acids or combinations thereof, and may be located internally or externally. Examples of PAMPs include bacterial carbohydrates (lipopolysaccharide or LPS, mannose), nucleic acids (bacterial or viral DNA or RNA), peptidoglycans and lipotechoic acids (from Gram positive bacteria), N-formylmethionine, lipoproteins and fungal glucans.

Pattern recognition receptors have evolved to take advantage of three PAMP qualities. First, constitutive expression allows the host to detect the pathogen regardless of its life cycle stage. Second, the PAMPs are class specific, which allows the host to distinguish between pathogens and thereby tailor its response. Third, mutation resistance allows the host to recognize the pathogen regardless of its particular strain.

Pattern recognition receptors are involved in more than just recognition of pathogens via their PAMPs. Once bound, pattern recognition receptors tend to cluster, recruit other extracellular and intracellular proteins to the complex, and initiate signaling cascades that ultimately impact transcription. Additionally, pattern recognition receptors are involved in activation of complement, coagulation, phagocytosis, inflammation, and apoptosis functions in response to pathogen detection.

Pattern recognition receptors (PRRs) may be divided into endocytic PRRs or signaling PRRs. The signaling PRRs include the large families of membrane-bound Toll-like receptors (TLRs) and cytoplasmic NOD-like receptors, while the endocytic PRRs promote the attachment, engulfment and destruction of microorganisms by phagocytes without relaying an intracellular signal, are found on all phagocytes and mediate removal of apoptotic cells. In addition, endocytic PRRs recognize carbohydrates and include mannose receptors of macrophages, glucan receptors present on all phagocytes and scavenger receptors that recognize charged ligands.

SUMMARY OF THE INVENTION

Provided herein are compounds and pharmaceutical compositions thereof, which are agonists of toll-like receptor 7 (TLR7). Such TLR7 agonists are immune potentiators. Also provided herein are immunogenic compositions that contain such TLR7 agonists.

In one aspect such compounds, and the pharmaceutically acceptable salts, individual isomers and mixture of isomers thereof, have a structure according to Formula (I):

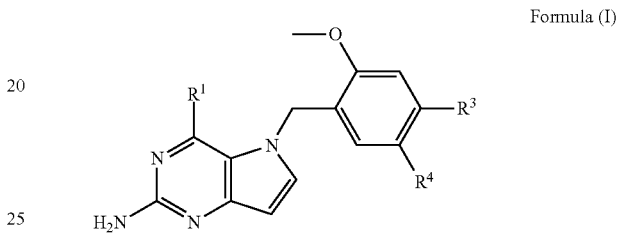

Formula (I)

wherein:
$R^1$ is —NHR$^6$ or —NHCHR$^6$R$^9$;
$R^3$ is H, -L$_2$C(=O)OR$^7$, —C(=O)OL$_6$R$^{12}$, —C(=O)OL$_2$R$^{12}$, -L$_2$C(=O)OL$_2$R$^{12}$, -L$_4$C(=O)OL$_5$OH, -L$_4$R$^{12}$, -L$_2$C(=O)OL$_4$C(=O)L$_2$R$^{12}$, -L$_2$C(=O)OL$_6$R$^{12}$, -L$_2$C(=O)OL$_4$C(=O)OL$_2$R$^{12}$, -L$_2$C(=O)OL$_4$C(=O)R$^{12}$, -L$_4$C(=O)OL$_2$C(=O)R$^{12}$, —CF$_2$C(=O)R$^7$, —CH=CHC(=O)OL$_4$C(=O)R$^{12}$, —OL$_2$C(=O)OL$_4$C(=O)R$^{12}$, —OL$_4$C(=O)OL$_2$R$^{12}$, —OL$_4$C(=O)OL$_2$C(=O)R$^{12}$ or -L$_2$C(=O)OL$_3$R$^{12}$;
$R^4$ is H, -L$_2$C(=O)OR$^7$, —C(=O)OL$_6$R$^{12}$, —C(=O)OL$_2$R$^{12}$, -L$_2$C(=O)OL$_2$R$^{12}$, -L$_4$C(=O)OL$_5$OH, -L$_4$R$^{12}$, -L$_2$C(=O)OL$_4$C(=O)L$_2$R$^{12}$, -L$_2$C(=O)OL$_6$R$^{12}$, -L$_2$C(=O)OL$_4$C(=O)OL$_2$R$^{12}$, -L$_2$C(=O)OL$_4$C(=O)R$^{12}$, -L$_4$C(=O)OL$_2$C(=O)R$^{12}$, —CF$_2$C(=O)R$^7$, —CH=CHC(=O)OL$_4$C(=O)R$^{12}$, —OL$_2$C(=O)OL$_4$C(=O)R$^{12}$, —OL$_4$C(=O)OL$_2$R$^{12}$, —OL$_4$C(=O)OL$_2$C(=O)R$^{12}$ or -L$_2$C(=O)OL$_3$R$^{12}$;
where when $R^4$ is H, then $R^3$ is -L$_2$C(=O)OR$^7$, —C(=O)OL$_6$R$^{12}$, —C(=O)OL$_2$R$^{12}$, -L$_2$C(=O)OL$_2$R$^{12}$, -L$_4$C(=O)OL$_5$OH, -L$_4$R$^{12}$, -L$_2$C(=O)OL$_4$C(=O)L$_2$R$^{12}$, -L$_2$C(=O)OL$_6$R$^{12}$, -L$_2$C(=O)OL$_4$C(=O)OL$_2$R$^{12}$, -L$_2$C(=O)OL$_4$C(=O)R$^{12}$, -L$_4$C(=O)OL$_2$C(=O)R$^{12}$, —CF$_2$C(=O)R$^7$, —CF$_2$C(=O)OR$^7$, —C(=O)OR$^7$, —N(R$^{11}$)$_2$, —CH=CHC(=O)OL$_4$C(=O)R$^{12}$, —OL$_2$C(=O)OL$_4$C(=O)R$^{12}$, —OL$_4$C(=O)OL$_2$R$^{12}$, —OL$_4$C(=O)OL$_2$C(=O)R$^{12}$ or -L$_2$C(=O)OL$_3$R$^{12}$;
or when $R^3$ is H, then $R^4$ is -L$_2$C(=O)OR$^7$, —C(=O)OL$_6$R$^{12}$, —C(=O)OL$_2$R$^{12}$, -L$_2$C(=O)OL$_2$R$^{12}$, -L$_4$C(=O)OL$_5$OH, -L$_4$R$^{12}$, -L$_2$C(=O)OL$_4$C(=O)L$_2$R$^{12}$, -L$_2$C(=O)OL$_6$R$^{12}$, -L$_2$C(=O)OL$_4$C(=O)OL$_2$R$^{12}$, -L$_2$C(=O)OL$_4$C(=O)R$^{12}$, -L$_4$C(=O)OL$_2$C(=O)R$^{12}$, —CF$_2$C(=O)R$^7$, —CF$_2$C(=O)OR$^7$, —C(=O)OR$^7$, —N(R$^{11}$)$_2$, —CH=CHC(=O)OL$_4$C(=O)R$^{12}$, —OL$_2$C(=O)OL$_4$C(=O)R$^{12}$, —OL$_4$C(=O)OL$_2$R$^{12}$, —OL$_4$C(=O)OL$_2$C(=O)R$^{12}$ or -L$_2$C(=O)OL$_3$R$^{12}$;
$L_1$ is —(CH$_2$)$_m$—; $L_2$ is —(CH$_2$)$_m$—; $L_3$ is —(CH$_2$)$_m$—; $L_4$ is —(CH$_2$)$_m$—; $L_5$ is —(CH$_2$)$_m$—; $L_6$ is —(CH$_2$)$_m$O(CH$_2$)$_m$—;

$L_9$ is —(CH$_2$)$_m$—; $R^6$ is —C$_4$-C$_6$alkyl; $R^7$ is —C$_1$-C$_3$alkyl; $R^9$ is $L_1$OH; each $R^{11}$ is independently selected from H or —C$_1$-C$_3$alkyl;

$R^{12}$ is
  a) —N(R$^{11}$)$_2$;
  b) an unsubstituted 5-6 membered heterocycloalkyl having 1 to 2 heteroatoms independently selected from N and O;
  c) a 5-6 membered heterocycloalkyl having 1 to 2 heteroatoms independently selected from N and O substituted with ═O;
  d) a 5-6 membered heterocycloalkyl having 1 to 2 heteroatoms independently selected from N and O substituted with C$_1$-C$_3$alkyl or —C(═O)OR$^7$;
  or
  e) an unsubstituted phenyl;
and
each m is independently selected from 1, 2, 3, and 4.

In certain embodiments, of the compound of Formula (I) wherein:
$R^1$ is —NHR$^6$ or —NHCHR$^6$R$^9$;
$R^3$ is H, -L$_2$C(═O)OR$^7$, —C(═O)OL$_6$R$^{12}$, —C(═O)OL$_2$R$^{12}$, -L$_2$C(═O)OL$_2$R$^{12}$, -L$_4$C(═O)OL$_6$OH, -L$_4$R$^{12}$, -L$_2$C(═O)OL$_4$C(═O)OL$_2$R$^{12}$, -L$_2$C(═O)OL$_6$R$^{12}$, -L$_2$C(═O)OL$_4$C(═O)OL$_2$R$^{12}$, -L$_2$C(═O)OL$_4$C(═O)R$^{12}$, -L$_4$C(═O)OL$_2$C(═O)R$^{12}$, —CF$_2$C(═O)R$^7$, —CH═CHC(═O)OL$_4$C(═O)R$^{12}$, —OL$_2$C(═O)OL$_4$C(═O)R$^{12}$, —OL$_4$C(═O)OL$_2$R$^{12}$, —OL$_4$C(═O)OL$_2$C(═O)R$^{12}$ or -L$_2$C(═O)OL$_3$R$^{12}$;
$R^4$ is H, -L$_2$C(═O)OR$^7$, —C(═O)OL$_6$R$^{12}$, —C(═O)OL$_2$R$^{12}$, -L$_2$C(═O)OL$_2$R$^{12}$, -L$_4$C(═O)OL$_6$OH, -L$_4$R$^{12}$, -L$_2$C(═O)OL$_4$C(═O)L$_2$R$^{12}$, -L$_2$C(═O)OL$_6$R$^{12}$, -L$_2$C(═O)OL$_4$C(═O)OL$_2$R$^{12}$, -L$_2$C(═O)OL$_4$C(═O)R$^{12}$, -L$_4$C(═O)OL$_2$C(═O)R$^{12}$, —CF$_2$C(═O)R$^7$, —CH═CHC(═O)OL$_4$C(═O)R$^{12}$, —OL$_2$C(═O)OL$_4$C(═O)R$^{12}$, —OL$_4$C(═O)OL$_2$R$^{12}$, —OL$_4$C(═O)OL$_2$C(═O)R$^{12}$ or -L$_2$C(═O)OL$_3$R$^{12}$;
where when $R^4$ is H, then $R^3$ is -L$_2$C(═O)OR$^7$, —C(═O)OL$_6$R$^{12}$, —C(═O)OL$_2$R$^{12}$, -L$_2$C(═O)OL$_2$R$^{12}$, -L$_4$C(═O)OL$_6$OH, -L$_4$R$^{12}$, -L$_2$C(═O)OL$_4$C(═O)L$_2$R$^{12}$, -L$_2$C(═O)OL$_6$R$^{12}$, -L$_2$C(═O)OL$_4$C(═O)OL$_2$R$^{12}$, -L$_2$C(═O)OL$_4$C(═O)R$^{12}$, -L$_4$C(═O)OL$_2$C(═O)R$^{12}$, —CF$_2$C(═O)R$^7$, —CH═CHC(═O)OL$_4$C(═O)R$^{12}$, —OL$_2$C(═O)OL$_4$C(═O)R$^{12}$, —OL$_4$C(═O)OL$_2$R$^{12}$, —OL$_4$C(═O)OL$_2$C(═O)R$^{12}$ or -L$_2$C(═O)OL$_3$R$^{12}$;
or when $R^3$ is H, then $R^4$ is -L$_2$C(═O)OR$^7$, —C(═O)OL$_6$R$^{12}$, —C(═O)OL$_2$R$^{12}$, -L$_2$C(═O)OL$_2$R$^{12}$, -L$_4$C(═O)OL$_6$OH, -L$_4$R$^{12}$, -L$_2$C(═O)OL$_4$C(═O)L$_2$R$^{12}$, -L$_2$C(═O)OL$_6$R$^{12}$, -L$_2$C(═O)OL$_4$C(═O)OL$_2$R$^{12}$, -L$_2$C(═O)OL$_4$C(═O)R$^{12}$, -L$_4$C(═O)OL$_2$C(═O)R$^{12}$, —CF$_2$C(═O)R$^7$, —CH═CHC(═O)OL$_4$C(═O)R$^{12}$, —OL$_2$C(═O)OL$_4$C(═O)R$^{12}$, —OL$_4$C(═O)OL$_2$R$^{12}$, —OL$_4$C(═O)OL$_2$C(═O)R$^{12}$ or -L$_2$C(═O)OL$_3$R$^{12}$;

$L_1$ is —(CH$_2$)$_m$—; $L_2$ is —(CH$_2$)$_m$—; $L_3$ is —(CH$_2$)$_m$—; $L_4$ is —(CH$_2$)$_m$—; $L_5$ is —(CH$_2$)$_m$—; $L_6$ is —(CH$_2$)$_m$O(CH$_2$)$_m$—;

$L_9$ is —(CH$_2$)$_m$—; $R^6$ is —C$_4$-C$_6$alkyl; $R^7$ is —C$_1$-C$_3$alkyl; $R^9$ is $L_1$OH; each $R^{11}$ is independently selected from H or —C$_1$-C$_3$alkyl;

$R^{12}$ is
  a) —N(R$^{11}$)$_2$;
  b) an unsubstituted 5-6 membered heterocycloalkyl having 1 to 2 heteroatoms independently selected from N and O;
  c) a 5-6 membered heterocycloalkyl having 1 to 2 heteroatoms independently selected from N and O substituted with ═O;
  d) a 5-6 membered heterocycloalkyl having 1 to 2 heteroatoms independently selected from N and O substituted with C$_1$-C$_3$alkyl or —C(═O)OR$^7$;
  or
  e) an unsubstituted phenyl;
and each m is independently selected from 1, 2, 3, and 4.

In certain embodiments, the compound of Formula (I) is a compound of Formula (Ia) or Formula (Ib):

Formula (Ia)

Formula (Ib)

In certain embodiments of the compounds of Formula (I), Formula (Ia) or Formula (Ib):
$R^1$ is —NHR$^6$ or —NHCHR$^6$R$^9$;
$R^3$ is H, -L$_2$C(═O)OR$^7$, —C(═O)OL$_6$R$^{12}$, —C(═O)OL$_2$R$^{12}$, -L$_2$C(═O)OL$_2$R$^{12}$, -L$_4$C(═O)OL$_5$OH, -L$_4$R$^{12}$, -L$_2$C(═O)OL$_4$C(═O)L$_2$R$^{12}$, -L$_2$C(═O)OL$_6$R$^{12}$, -L$_2$C(═O)OL$_4$C(═O)OL$_2$R$^{12}$, -L$_2$C(═O)OL$_4$C(═O)R$^{12}$, -L$_4$C(═O)OL$_2$C(═O)R$^{12}$ or -L$_2$C(═O)OL$_3$R$^{12}$;
$R^4$ is H, —CF$_2$C(═O)R$^7$, -L$_4$R$^{12}$, —CH═CHC(═O)OL$_4$C(═O)R$^{12}$, —OL$_2$C(═O)OL$_4$C(═O)R$^{12}$, —OL$_4$C(═O)OL$_2$R$^{12}$, -L$_2$C(═O)OR$^7$, -L$_2$C(═O)OL$_4$C(═O)R$^{12}$, —OL$_4$C(═O)OL$_2$C(═O)R$^{12}$ or -L$_2$C(═O)OL$_3$R$^{12}$;
where when $R^4$ is H, then $R^3$ is -L$_2$C(═O)OR$^7$, —C(═O)OL$_6$R$^{12}$, —C(═O)OL$_2$R$^{12}$, -L$_2$C(═O)OL$_2$R$^{12}$, -L$_4$C(═O)OL$_5$OH, -L$_4$R$^{12}$, -L$_2$C(═O)OL$_4$C(═O)L$_2$R$^{12}$, -L$_2$C(═O)OL$_6$R$^{12}$, -L$_2$C(═O)OL$_4$C(═O)OL$_2$R$^{12}$, -L$_2$C(═O)OL$_4$C(═O)R$^{12}$, -L$_4$C(═O)OL$_2$C(═O)R$^{12}$ or -L$_2$C(═O)OL$_3$R$^{12}$;
or when $R^3$ is H, then $R^4$ is —CF$_2$C(═O)R$^7$, -L$_4$R$^{12}$, —CH═CHC(═O)OL$_4$C(═O)R$^{12}$, —OL$_2$C(═O)OL$_4$C(═O)R$^{12}$, —OL$_4$C(═O)OL$_2$R$^{12}$, -L$_2$C(═O)OR$^7$, -L$_2$C(═O)OL$_4$C(═O)R$^{12}$, —OL$_4$C(═O)OL$_2$C(═O)R$^{12}$ or -L$_2$C(═O)OL$_3$R$^{12}$;
$L_1$ is —CH$_2$—; $L_2$ is —CH$_2$— or —CH$_2$CH$_2$—; $L_3$ is —CH$_2$CH$_2$— or —CH$_2$CH$_2$CH$_2$CH$_2$—; $L_4$ is —CH$_2$—, $L_5$ is —CH$_2$CH$_2$—, $L_6$ is —(CH$_2$)$_2$O(CH$_2$)$_2$—; $L_9$ is —CH$_2$CH$_2$CH$_2$CH$_2$—; $R^6$ is —C$_4$alkyl or —C$_5$alkyl; $R^7$ is methyl, ethyl or propyl; $R^9$ is $L_1$OH; each $R^{11}$ is independently selected from —C$_1$-C$_3$alkyl;

$R^{12}$ is
  a) —N(R$^{11}$)$_2$;
  b) an unsubstituted piperazinyl or an unsubstituted morpholinyl;
  c) a 5-6 membered heterocycloalkyl having 1 to 2 heteroatoms independently selected from N and O substituted with ═O;
  d) a piperazinyl substituted with C$_1$-C$_3$alkyl or —C(═O)OR$^7$;

or e) an unsubstituted phenyl;

and each m is independently selected from 1, 2, 3, and 4.

In certain embodiments of the compounds of Formula (Ia) or Formula (Ib), $R^1$ is $-NHR^6$ or $-NHCHR^6R^9$;

$R^3$ is $-L_2C(=O)OR^7$, $-C(=O)OL_6R^{12}$, $-C(=O)OL_2R^{12}$, $-L_2C(=O)OL_2R^{12}$, $-L_4C(=O)OL_6OH$, $-L_4R^{12}$, $-L_2C(=O)OL_4C(=O)L_2R^{12}$, $-L_2C(=O)OL_6R^{12}$, $-L_2C(=O)OL_4C(=O)OL_2R^{12}$, $-L_2C(=O)OL_4C(=O)R^{12}$, $-L_4C(=O)OL_2C(=O)R^{12}$, $-CF_2C(=O)OR^7$, $-C(=O)OR^7$, $-N(R^{11})_2$ or $-L_2C(=O)OL_3R^{12}$;

$R^4$ is $-CF_2C(=O)R^7$, $-L_4R^{12}$, $-CH=CHC(=O)OL_4C(=O)R^{12}$, $-OL_2C(=O)OL_4C(=O)R^{12}$, $-OL_4C(=O)OL_2R^{12}$, $-L_2C(=O)OR^7$, $-L_2C(=O)OL_4C(=O)R^{12}$, $-OL_4C(=O)OL_2C(=O)R^{12}$, $-CF_2C(=O)OR^7$, $-C(=O)OR^7$, $-N(R^{11})_2$ or $-L_2C(=O)OL_3R^{12}$;

$L_1$ is $-CH_2-$; $L_2$ is $-CH_2-$ or $-CH_2CH_2-$; $L_3$ is $-CH_2CH_2-$ or $-CH_2CH_2CH_2CH_2-$; $L_4$ is $-CH_2-$, $L_5$ is $-CH_2CH_2-$, $L_6$ is $-(CH_2)_2O(CH_2)_2-$; $L_9$ is $-CH_2CH_2CH_2CH_2-$; $R^6$ is $-C_4$alkyl or $-C_5$alkyl; $R^7$ is methyl, ethyl or propyl; $R^9$ is $L_1OH$; each $R^{11}$ is independently selected from $-C_1-C_3$alkyl;

$R^{12}$ is a) $-N(R^{11})_2$;

b) an unsubstituted piperazinyl or an unsubstituted morpholinyl;

c) a 5-6 membered heterocycloalkyl having 1 to 2 heteroatoms independently selected from N and O substituted with $=O$;

d) a piperazinyl substituted with $C_1-C_3$alkyl or $-C(=O)OR^7$;

or e) an unsubstituted phenyl;

and each m is independently selected from 1, 2, 3, and 4

In certain embodiments of the compounds of Formula (Ia) or Formula (Ib), $R^1$ is $-NHR^6$ or $-NHCHR^6R^9$;

$R^3$ is $-L_2C(=O)OR^7$, $-C(=O)OL_6R^{12}$, $-C(=O)OL_2R^{12}$, $-L_2C(=O)OL_2R^{12}$, $-L_4C(=O)OL_6OH$, $-L_4R^{12}$, $-L_2C(=O)OL_4C(=O)L_2R^{12}$, $-L_2C(=O)OL_6R^{12}$, $-L_2C(=O)OL_4C(=O)OL_2R^{12}$, $-L_2C(=O)OL_4C(=O)R^{12}$ or $-L_2C(=O)OL_3R^{12}$;

$R^4$ is $-CF_2C(=O)R^7$, $-L_4R^{12}$, $-CH=CHC(=O)OL_4C(=O)R^{12}$, $-OL_2C(=O)OL_4C(=O)R^{12}$, $-OL_4C(=O)OL_2R^{12}$, $-L_2C(=O)OR^7$, $-L_2C(=O)OL_4C(=O)R^{12}$, $-OL_4C(=O)OL_2C(=O)R^{12}$ or $-L_2C(=O)OL_3R^{12}$;

$L_1$ is $-CH_2-$; $L_2$ is $-CH_2-$ or $-CH_2CH_2-$; $L_3$ is $-CH_2CH_2-$ or $-CH_2CH_2CH_2CH_2-$; $L_4$ is $-CH_2-$, $L_5$ is $-CH_2CH_2-$, $L_6$ is $-(CH_2)_2O(CH_2)_2-$; $L_9$ is $-CH_2CH_2CH_2CH_2-$; $R^6$ is $-C_4$alkyl or $-C_5$alkyl; $R^7$ is methyl, ethyl or propyl; $R^9$ is $L_1OH$; each $R^{11}$ is independently selected from $-C_1-C_3$alkyl;

$R^{12}$ is a) $-N(R^{11})_2$;

b) an unsubstituted piperazinyl or an unsubstituted morpholinyl;

c) a 5-6 membered heterocycloalkyl having 1 to 2 heteroatoms independently selected from N and O substituted with $=O$;

d) a piperazinyl substituted with $C_1-C_3$alkyl or $-C(=O)OR^7$;

or e) an unsubstituted phenyl;

and each m is independently selected from 1, 2, 3, and 4.

In certain embodiments of the compounds of Formula (I), Formula (Ia) and Formula (Ib), $R^1$ is $-NHR^6$;

$R^3$ is $-L_2C(=O)OL_4C(=O)R^{12}$ and $R^4$ is H;

or $R^3$ is H and $R^4$ is $-L_2C(=O)OL_4C(=O)R^{12}$;

$R^6$ is $-C_4-C_6$alkyl;

$L_2$ is $-(CH_2)_m-$;

$L_4$ is $-(CH_2)_m-$;

$R^{12}$ is an unsubstituted 5-6 membered heterocycloalkyl having 1 to 2 heteroatoms independently selected from N and O;

and each m is independently selected from 1, 2, 3, and 4

In certain embodiments of the compounds of Formula (I), Formula (Ia) and Formula (Ib), $R^1$ is $-NHR^6$;

$R^3$ is $-L_2C(=O)OL_4C(=O)L_2R^{12}$ and $R^4$ is H;

or $R^3$ is H and $R^4$ is $-L_2C(=O)OL_4C(=O)L_2R^{12}$;

$R^6$ is $-C_4-C_6$alkyl; $L_2$ is $-(CH_2)_m-$; $L_4$ is $-(CH_2)_m-$;

$R^{12}$ is an unsubstituted 5-6 membered heterocycloalkyl having 1 to 2 heteroatoms independently selected from N and O;

and each m is independently selected from 1, 2, 3, and 4.

In certain embodiments of the compounds of Formula (I), Formula (Ia) and Formula (Ib), $R^1$ is $-NHR^6$;

$R^3$ is $-L_2C(=O)OL_4C(=O)L_2R^{12}$ and $R^4$ is H;

or $R^3$ is H and $R^4$ is $-L_2C(=O)OL_4C(=O)L_2R^{12}$;

$R^6$ is $-C_5$alkyl; $L_2$ is $-CH_2-$ or $-CH_2CH_2-$; $L_4$ is $-CH_2-$, and $R^{12}$ is an unsubstituted piperazinyl or an unsubstituted morpholinyl.

In certain embodiments of the compounds of Formula (I), Formula (Ia) and Formula (Ib), $R^1$ is $-NHR^6$;

$R^3$ is $-L_2C(=O)OL_4C(=O)R^{12}$ and $R^4$ is H;

or $R^3$ is H and $R^4$ is $-L_2C(=O)OL_4C(=O)R^{12}$;

$R^6$ is $-C_5$alkyl;

$L_2$ is $-CH_2-$ or $-CH_2CH_2-$;

$L_4$ is $-CH_2-$, and $R^{12}$ is an unsubstituted piperazinyl or an unsubstituted morpholiny In certain embodiments of the compounds of Formula (I), Formula (Ia) and Formula (Ib), $R^1$ is $-NHR^6$ or $-NHCHR^6R^9$;

$R^3$ is H and $R^4$ is $-L_4R^{12}$;

or $R^3$ is $-L_4R^{12}$ and $R^4$ is H;

$L_1$ is $-(CH_2)_m-$; $L_4$ is $-(CH_2)_m-$; $R^6$ is $-C_4-C_6$alkyl; $R^9$ is $L_1OH$;

$R^{12}$ is an unsubstituted 5-6 membered heterocycloalkyl having 1 to 2 heteroatoms independently selected from N and O;

and each m is independently selected from 1, 2, 3, and 4.

In certain embodiments of the compounds of Formula (I), Formula (Ia) and Formula (Ib), $R^1$ is $-NHR^6$ or $-NHCHR^6R^9$;

$R^3$ is H and $R^4$ is $-L_4R^{12}$;

or $R^3$ is $-L_4R^{12}$ and $R^4$ is H;

$L_1$ is $-(CH_2)-$; $L_4$ is $-(CH_2)-$; $R^6$ is $-C_4$alkyl or $-C_5$alkyl; $R^9$ is $L_1OH$, and $R^{12}$ is an unsubstituted piperazinyl.

In certain embodiments of the compounds of Formula (I), Formula (Ia) and Formula (Ib) the compound is selected from:

2-(dimethylamino)ethyl 4-((2-amino-4-(pentylamino)-5H-pyrrolo[3,2-d]pyrimidin-5-yl)methyl)-3-methoxybenzoate;
2-(2-(dimethylamino)ethoxy)ethyl 4-((2-amino-4-(pentylamino)-5H-pyrrolo[3,2-d]pyrimidin-5-yl)methyl)-3-methoxybenzoate;
methyl 2-(3-((2-amino-4-(pentylamino)-5H-pyrrolo[3,2-d]pyrimidin-5-yl)methyl)-4-methoxyphenyl)acetate;
ethyl 3-(3-((2-amino-4-(pentylamino)-5H-pyrrolo[3,2-d]pyrimidin-5-yl)methyl)-4-methoxyphenyl)propanoate;
methyl 2-(3-((2-amino-4-(pentylamino)-5H-pyrrolo[3,2-d]pyrimidin-5-yl)methyl)-4-methoxyphenyl)-2,2-difluoroacetate;
2-morpholino-2-oxoethyl 2-(3-((2-amino-4-(pentylamino)-5H-pyrrolo[3,2-d]pyrimidin-5-yl)methyl)-4-methoxyphenoxy)acetate;
2-morpholino-2-oxoethyl 2-(3-((2-amino-4-(pentylamino)-5H-pyrrolo[3,2-d]pyrimidin-5-yl)methyl)-4-methoxyphenyl)acetate;
2-morpholino-2-oxoethyl 2-(4-((2-amino-4-(pentylamino)-5H-pyrrolo[3,2-d]pyrimidin-5-yl)methyl)-3-methoxyphenyl)acetate;
2-(morpholin-4-yl)-2-oxoethyl 3-(4-{[2-amino-4-(pentylamino)-5H-pyrrolo[3,2-d]pyrimidin 5-yl]methyl}-3-methoxyphenyl)propanoate;
(S)-2-morpholino-2-oxoethyl 3-(3-((2-amino-4-((1-hydroxyhexan-2-yl)amino)-5H-pyrrolo[3,2-d]pyrimidin-5-yl)methyl)-4-methoxyphenyl)propanoate;
(S)-2-morpholino-2-oxoethyl 2-(4-((2-amino-4-((1-hydroxyhexan-2-yl)amino)-5H-pyrrolo[3,2-d]pyrimidin-5-yl)methyl)-3-methoxyphenyl)acetate;
(S)-2-morpholino-2-oxoethyl 2-(3-((2-amino-4-((1-hydroxyhexan-2-yl)amino)-5H-pyrrolo[3,2-d]pyrimidin-5-yl)methyl)-4-methoxyphenyl)acetate;
(S)-2-morpholino-2-oxoethyl 3-(4-((2-amino-4-((1-hydroxyhexan-2-yl)amino)-5H-pyrrolo[3,2-d]pyrimidin-5-yl)methyl)-3-methoxyphenyl)propanoate;
2-(morpholin-4-yl)-2-oxoethyl (2E)-3-(3-{[2-amino-4-(pentylamino)-5H-pyrrolo[3,2-d]pyrimidin-5-yl]methyl}-4-methoxyphenyl)prop-2-enoate;
2-(morpholin-4-yl)-2-oxoethyl 3-(3-{[2-amino-4-(pentylamino)-5H-pyrrolo[3,2-d]pyrimidin 5-yl]methyl}-4-methoxyphenyl)propanoate;
2-(benzyloxy)-2-oxoethyl 2-(4-{[2-amino-4-(pentylamino)-5H-pyrrolo[3,2-d]pyrimidin-5-yl]methyl}-3-methoxyphenyl)acetate;
2-(dipropylcarbamoyl)methyl 2-(4-{[2-amino-4-(pentylamino)-5H-pyrrolo[3,2-d]pyrimidin yl]methyl}-3-methoxyphenyl)acetate;
2-(dimethylamino)-2-oxoethyl 2-(4-((2-amino-4-(pentylamino)-5H-pyrrolo[3,2-d]pyrimidin-5-yl)methyl)-3-methoxyphenyl)acetate;
2-(4-methylpiperazin-1-yl)ethyl 2-(4-{[2-amino-4-(pentylamino)-5H-pyrrolo[3,2-d]pyrimidin-5-yl]methyl}-3-methoxyphenyl)acetate;
2-hydroxyethyl 2-(4-{[2-amino-4-(pentylamino)-5H-pyrrolo[3,2-d]pyrimidin-5-yl]methyl}-3 methoxyphenyl)acetate;
4-(dimethylamino)butyl 2-(4-{[2-amino-4-(pentylamino)-5H-pyrrolo[3,2-d]pyrimidin-5-yl]methyl}-3-methoxyphenyl)acetate;
2-(morpholin-4-yl)ethyl 2-(4-{[2-amino-4-(pentylamino)-5H-pyrrolo[3,2-d]pyrimidin-5-yl]methyl}-3-methoxyphenyl)acetate;
2-(piperazin-1-yl)ethyl 2-(4-{[2-amino-4-(pentylamino)-5H-pyrrolo[3,2-d]pyrimidin-5-yl]methyl}-3-methoxyphenyl)acetate;
2-(dimethylamino)ethyl 2-(3-{[2-amino-4-(pentylamino)-5H-pyrrolo[3,2-d]pyrimidin-5-yl]methyl}-4-methoxyphenoxy)acetate;
2-(piperazin-1-yl)ethyl 2-(3-{[2-amino-4-(pentylamino)-5H-pyrrolo[3,2-d]pyrimidin-5-yl]methyl}-4-methoxyphenoxy)acetate;
2-(morpholin-4-yl)ethyl 2-(3-{[2-amino-4-(pentylamino)-5H-pyrrolo[3,2-d]pyrimidin-5-yl]methyl}-4-methoxyphenoxy)acetate;
2-(4-methylpiperazin-1-yl)ethyl 2-(3-{[2-amino-4-(pentylamino)-5H-pyrrolo[3,2-d]pyrimidin-5-yl]methyl}-4-methoxyphenoxy)acetate;
(S)-2-((2-amino-5-(2-methoxy-4-(piperazin-1-ylmethyl)benzyl)-5H-pyrrolo[3,2-d]pyrimidin-4-yl)amino)hexan-1-ol;
5-(2-methoxy-4-(piperazin-1-ylmethyl)benzyl)-N4-pentyl-5H-pyrrolo[3,2-d]pyrimidine-2,4-diamine;
5-(2-methoxy-5-(piperazin-1-ylmethyl)benzyl)-N4-pentyl-5H-pyrrolo[3,2-d]pyrimidine-2,4-diamine;
(S)-2-((2-amino-5-(2-methoxy-5-(piperazin-1-ylmethyl)benzyl)-5H-pyrrolo[3,2-d]pyrimidin-4-yl)amino)hexan-1-ol, and
5-(5-amino-2-methoxybenzyl)-N4-pentyl-5H-pyrrolo[3,2-d]pyrimidine-2,4-diamine.

In certain embodiments of the compounds of Formula (I), Formula (Ia) and Formula (Ib) the compound is selected from:
2-morpholino-2-oxoethyl 2-(3-((2-amino-4-(pentylamino)-5H-pyrrolo[3,2-d]pyrimidin-5-yl)methyl)-4-methoxyphenoxy)acetate;
2-morpholino-2-oxoethyl 2-(3-((2-amino-4-(pentylamino)-5H-pyrrolo[3,2-d]pyrimidin-5-yl)methyl)-4-methoxyphenyl)acetate;
2-morpholino-2-oxoethyl 2-(4-((2-amino-4-(pentylamino)-5H-pyrrolo[3,2-d]pyrimidin-5-yl)methyl)-3-methoxyphenyl)acetate, and
2-(morpholin-4-yl)-2-oxoethyl 3-(4-{[2-amino-4-(pentylamino)-5H-pyrrolo[3,2-d]pyrimidin-5-yl]methyl}-3-methoxyphenyl)propanoate.

In certain embodiments of the compounds of Formula (I), Formula (Ia) and Formula (Ib) the compound is selected from:
(S)-2-((2-amino-5-(2-methoxy-4-(piperazin-1-ylmethyl)benzyl)-5H-pyrrolo[3,2-d]pyrimidin-4-yl)amino)hexan-1-ol;
5-(2-methoxy-4-(piperazin-1-ylmethyl)benzyl)-N4-pentyl-5H-pyrrolo[3,2-d]pyrimidine-2,4-diamine;
5-(2-methoxy-5-(piperazin-1-ylmethyl)benzyl)-N4-pentyl-5H-pyrrolo[3,2-d]pyrimidine-2,4-diamine;
(S)-2-((2-amino-5-(2-methoxy-5-(piperazin-1-ylmethyl)benzyl)-5H-pyrrolo[3,2-d]pyrimidin-4-yl)amino)hexan-1-ol, and
5-(5-amino-2-methoxybenzyl)-N4-pentyl-5H-pyrrolo[3,2-d]pyrimidine-2,4-diamine.

Another aspect, provided herein are methods of using compounds of Formula (I), Formula (Ia) and Formula (Ib), and pharmaceutical compositions comprising such compounds of Formula (I), Formula (Ia) and Formula (Ib).

Another aspect provided herein are pharmaceutical compositions that include a therapeutically effective amount of a compound of Formula (I), Formula (Ia) or Formula (Ib), and a pharmaceutically acceptable carrier. In certain embodiments of such pharmaceutical compositions, the pharmaceutical composition is formulated for intravenous administration, intravitrial administration, intramuscular administration, oral administration, rectal administration inhalation, nasal administration, topical administration, ophthalmic administration or otic administration. In other embodiments, the pharmaceutical compositions are in the form of a tablet, a pill, a capsule, a liquid, an inhalant, a nasal spray solution, a suppository, a solution, an emulsion, an ointment, eye drop or ear drop. In other embodiments, such pharmaceutical compositions further include one or more additional therapeutic agents.

Another aspect provided herein are medicaments for treating a patient with a disease or disorder associated with TLR7 receptor activity, and such medicaments include a therapeutically effective amount of a compound of Formula (I), Formula (Ia) or Formula (Ib).

Another aspect provided herein is the use of a compound of Formula (I), Formula (Ia) or Formula (Ib) in the manufacture of a medicament for treating a disease or disorder associated with TLR7 activity. In certain embodiments of such uses the disease is an infectious disease, a viral infectious disease, an inflammatory disease, a respiratory disease, a dermatological disease, an autoimmune disease, a cell-proliferative disease or cancer. In certain embodiments of such uses the disease is asthma, chronic obstructive pulmonary disease (COPD), adult respiratory distress syndrome (ARDS), ulcerative colitis, Crohn's disease, bronchitis, dermatitis, actinic keratosis, basal cell carcinoma, bladder cancer, allergic rhinitis, psoriasis, scleroderma, urticaria, rheumatoid arthritis, multiple sclerosis, cancer, breast cancer, HIV, hepatitis, hepatitis C or lupus. In certain embodiments of such uses the disease is hepatitis B, hepatitis C, colorectal cancer or hepatocellular carcinoma.

Another aspect provided herein are methods for activating a TLR7 receptor, wherein the method includes administering to a system or a subject in need thereof, a therapeutically effective amount of a compound of Formula (I), Formula (Ia) or Formula (Ib), or pharmaceutically acceptable salts or pharmaceutical compositions thereof, thereby activating the TLR receptor. In certain embodiments of such methods, the methods include administering the compound to a cell or tissue system or to a human or animal subject.

Another aspect provided herein are methods for treating a disease or disorder associated with TLR7 activity, wherein the method includes administering to a system or subject in need of such treatment an effective amount of a compound of Formula (I), Formula (Ia) or Formula (Ib), or pharmaceutically acceptable salts thereof, thereby treating the disease or disorder. In certain embodiments of such methods, the methods include administering the compound to a cell or tissue system or to a human or animal subject. In certain embodiments of such methods, the disease or condition is an infectious disease, a viral infectious disease, an inflammatory disease, a respiratory disease, a dermatological disease, an autoimmune disease, a cell-proliferative disease or cancer. In certain embodiments of such methods, the disease or condition is asthma, chronic obstructive pulmonary disease (COPD), adult respiratory distress syndrome (ARDS), ulcerative colitis, Crohn's disease, bronchitis, dermatitis, actinic keratosis, basal cell carcinoma, bladder cancer, allergic rhinitis, psoriasis, scleroderma, urticaria, rheumatoid arthritis, multiple sclerosis, cancer, breast cancer, HIV, hepatitis, hepatitis C or lupus. In certain embodiments of such methods the disease is hepatitis B, hepatitis C, colorectal cancer or hepatocellular carcinoma.

Another aspect provided herein are methods for treating a cell-proliferative disease, comprising administering to a system or subject in need of such treatment an effective amount of a compound of Formula (I), Formula (Ia) or Formula (Ib), or pharmaceutically acceptable salts thereof; wherein the cell-proliferative disease is bladder cancer, lymphoma, osteosarcoma, melanoma, or a tumor of breast, renal, prostate, colorectal, thyroid, ovarian, pancreatic, neuronal, lung, uterine or gastrointestinal tumor. In certain embodiments of such methods the cell proliferative disease is colorectal cancer or hepatocellular carcinoma. In certain embodiments of such methods the cell proliferative disease is colorectal cancer. In certain embodiments of such methods the cell proliferative disease is hepatocellular carcinoma.

Another aspect provided herein are compounds for use in a method of medical treatment, wherein the method of medical treatment is for treating a disease associated with TLR7 receptor activity, wherein the disease is selected from an infectious disease, a viral infectious disease, an inflammatory disease, a respiratory disease, a dermatological disease, an autoimmune disease, a cell-proliferative disease or cancer, and wherein the compound is a compound of Formula (I), Formula (Ia) or Formula (Ib). In certain embodiments of such methods, the disease or condition is asthma, chronic obstructive pulmonary disease (COPD), adult respiratory distress syndrome (ARDS), ulcerative colitis, Crohn's disease, bronchitis, dermatitis, actinic keratosis, basal cell carcinoma, bladder cancer, allergic rhinitis, psoriasis, scleroderma, urticaria, rheumatoid arthritis, multiple sclerosis, cancer, breast cancer, HIV, hepatitis, hepatitis C or lupus. In certain embodiments of such methods the disease is hepatitis B, hepatitis C, colorectal cancer or hepatocellular carcinoma.

DETAILED DESCRIPTION OF THE INVENTION

Definitions

The term "alkyl," as used herein, refers to a saturated branched or straight chain hydrocarbon. In certain embodiments such alkyl groups are optionally substituted. As used herein, the terms "$C_1$-$C_3$alkyl", "$C_1$-$C_4$alkyl", "$C_1$-$C_5$alkyl", "$C_1$-$C_6$alkyl", "$C_1$-$C_7$alkyl" and "$C_1$-$C_8$alkyl" refer to an alkyl group containing at least 1, and at most 3, 4, 5, 6, 7 or 8 carbon atoms, respectively. If not otherwise specified, an alkyl group generally is a $C_1$-$C_6$ alkyl. Non-limiting examples of alkyl groups as used herein include methyl, ethyl, n-propyl, isopropyl, n-butyl, isobutyl, sec-butyl, t-butyl, n-pentyl, isopentyl, hexyl, heptyl, octyl, nonyl, decyl and the like.

The term "heteroatom," as used herein, refers to nitrogen (N), oxygen (O) or sulfur (S) atoms.

The term "heterocycloalkyl," as used herein refers to a to saturated 3-6 membered monocyclic hydrocarbon ring structure, a to saturated 5-6 membered monocyclic hydrocarbon ring structure, a saturated 6-9 membered fused bicyclic hydrocarbon ring structure, or a saturated 10-14 membered fused tricyclic hydrocarbon ring structure, wherein one to four of the ring carbons of the hydrocarbon ring structure are replaced by one to four groups independently selected from —O—, —NR—, or —S—, wherein R is hydrogen, $C_1$-$C_4$alkyl or an amino protecting group.

Non-limiting examples of heterocycloalkyl groups, as used herein, include aziridinyl, aziridin-1-yl, aziridin-2-yl, aziridin-3-yl, oxiranyl, oxiran-2-yl, oxiran-3-yl, thiiranyl, thiiran-2-yl, thiiran-3-yl, azetadinyl, azetadin-1-yl, azetadin-2-yl, azetadin-3-yl, oxetanyl, oxetan-2-yl, oxetan-3-yl, oxetan-4-yl, thietanyl, thietan-2-yl, thietan-3-yl, thietan-4-yl, pyrrolidinyl, pyrrolidin-1-yl, pyrrolidin-2-yl, pyrrolidin-3-yl, pyrrolidin-4-yl, pyrrolidin-5-yl, tetrahydrofuranyl, tetrahydrofuran-2-yl, tetrahydrofuran-3-yl, tetrahydrofuran-4- yl, tetrahydrofuran-5-yl, tetrahydrothienyl, tetrahydrothien-2-yl, tetrahydrothien-3-yl, tetrahydrothien-4-yl, tetrahydrothien-5-yl, piperidinyl, piperidin-1-yl, piperidin-2-yl, piperidin-3-yl, piperidin-4-yl, piperidin-5-yl, piperidin-6-yl, tetrahydropyranyl, tetrahydropyran-2-yl, tetrahydropyran-3-yl, tetrahydropyran-4-yl, tetrahydropyran-5-yl, tetrahydropyran-6-yl, tetrahydrothiopyranyl, tetrahydrothiopyran-2-yl, tetrahydrothiopyran-3-yl, tetrahydrothiopyran-4-yl, tetrahydrothiopyran-5-yl, tetrahydrothiopyran-6-yl, piperazinyl, piperazin-1-yl, piperazin-2-yl, piperazin-3-yl, piperazin-4-yl, piperazin-5-yl, piperazin-6-yl, morpholinyl, morpholin-2-yl, morpholin-3-yl, morpholin-4-yl, morpholin-5-yl, morpholin-6-yl, thiomorpholinyl, thiomorpholin-2-yl, thiomorpholin-3-yl, thiomorpholin-4-yl, thiomorpholin-5-yl, thiomorpholin-6-yl, oxathianyl, oxathian-2-yl, oxathian-3-yl, oxathian-5-yl, oxathian-6-yl, dithianyl, dithian-2-yl, dithian-3-yl, dithian-5-yl, dithian-6-yl, azepanyl, azepan-1-yl, azepan-2-yl, azepan-3-yl, azepan-4-yl, azepan-5-yl, azepan-6-yl, azepan-7-yl, oxepanyl, oxepan-2-yl, oxepan-3-yl, oxepan-4-yl, oxepan-5-yl, oxepan-6-yl, oxepan-7-yl, thiepanyl, thiepan-2-yl, thiepan-3-yl, thiepan-4-yl, thiepan-5-yl, thiepan-6-yl, thiepan-7-yl, dioxolanyl, dioxolan-2-yl, dioxolan-4-yl, dioxolan-5-yl, thioxanyl, thioxan-2-yl, thioxan-3-yl, thioxan-4-yl, thioxan-5-yl, dithiolanyl, dithiolan-2-yl, dithiolan-4-yl, dithiolan-5-yl, pyrrolinyl, pyrrolin-1-yl, pyrrolin-2-yl, pyrrolin-3-yl, pyrrolin-4-yl, pyrrolin-5-yl, imidazolinyl, imidazolin-1-yl, imidazolin-3-yl, imidazolin-4-yl, imidazolin-5-yl, imidazolidinyl, imidazolidin-1-yl, imidazolidin-2-yl, imidazolidin-3-yl, imidazolidin-4-yl, imidazolidin-4-yl, pyrazolinyl, pyrazolin-1-yl, pyrazolin-3-yl, pyrazolin-4-yl, pyrazolin-5-yl, pyrazolidinyl, pyrazolidin-1-yl, pyrazolidin-2-yl, pyrazolidin-3-yl, pyrazolidin-4-yl, pyrazolidin-5-yl, hexahydro-1,4-diazepinyl, dihydrofuranyldihydropyranyl, 1,2,3,6-tetrahydropyridinyl, 2H-pyranyl, 4H-pyranyl, dihydropyranyl, dihydrothienyl, dihydrofuranyl, 3-azabicyclo[3.1.0]hexanyl, 3-azabicyclo[4.1.0]heptanyl, pyrrolidinyl-2-one, piperidinyl-3-one piperidinyl-2-one, piperidinyl-4-one, and 2H-pyrrolyl The term "acceptable" with respect to a formulation, composition or ingredient, as used herein, means having no persistent detrimental effect on the general health of the subject being treated.

The term "administration" or "administering" of the subject compound means providing a compound of Formula (I) or a pharmaceutically acceptable salt thereof to a subject in need of treatment.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to chemical compounds or agents that facilitate the incorporation of a compound described herein into cells or tissues.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, actinic keratosis, basal cell carcinoma and urticaria.

The term "diluent," as used herein, refers to chemical compounds that are used to dilute a compound described herein prior to delivery. Diluents can also be used to stabilize compounds described herein.

The terms "effective amount" or "therapeutically effective amount," as used herein, refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "excipient" refers to any essentially accessory substance that may be present in the finished dosage form. For example, the term "excipient" includes vehicles, binders, disontegrants, fillers (diluents), lubricants, suspending/dispersing agents, and the like.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic," as used herein, means a condition, disorder, or disease created or worsened by medical or surgical therapy.

The term "immunologically effective amount," as used herein, means that the administration of a sufficient amount to an individual, either in a single dose or as part of a series, that is effective for treatment or prevention of an immunological disease or disorder. This amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the treating doctor's assessment of the medical situation, and other relevant factors. It is expected that the amount will fall in a relatively broad range that can be determined through routine trials.

An "immunological response" or "immune response" to an antigen or composition, as used herein, refers to the development in a subject of a humoral and/or cellular immune response to the antigen or composition.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and β-glucan receptors. Dendritic cells are recognized as some of the most important cell types for initiating the priming of naive CD4$^+$ helper T ($T_H$) cells and for inducing CD8$^+$ T cell differentiation into killer cells. TLR signaling has been reported to play an important role in determining the quality of these helper T cell responses, for instance, with the nature of the TLR signal determining the specific type of $T_H$ response that is observed (e.g., $T_H1$ versus $T_H2$ response). A combination of antibody (humoral) and cellular immunity are produced as part of a $T_H1$-type response, whereas a $T_H2$-type response is predominantly an antibody response.

A "humoral immune response" refers to an immune response mediated by antibody molecules, while a "cellular immune response" refers to an immune response mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

The term "inflammatory disorders," as used herein, refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arthritis); joints (arthritis: crystalline, osteo-, psoriatic, reactive, rheumatoid, Reiter's); gastrointestinal tract (Disease); skin (dermatitis); or multiple organs and tissues (systemic lupus erythematosus).

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjuctivitis, vernal conjunctivitis, papillary conjunctivitis and cytomegalovirus (CMV) retinitis.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt," as used herein, refers to a formulation of a compound that does not cause significant irritation to an organism to which it is administered and does not abrogate the biological activity and properties of the compounds described herein.

The terms "combination" or "pharmaceutical combination," as used herein mean a product that results from the mixing or combining of more than one active ingredient and includes both fixed and non-fixed combinations of the active ingredients. The term "fixed combination" means that the active ingredients, by way of example, a compound of Formula (I) and an additional therapeutic agent, are both administered to a patient simultaneously in the form of a single entity or dosage. The term "non-fixed combination" means that the active ingredients, by way of example, a compound of Formula (I) and an additional therapeutic agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The terms "composition" or "pharmaceutical composition," as used herein, refers to a mixture a compound of Formula (I), Formula (Ia) or Formula (Ib), or pharmaceutically acceptable salt thereof, with at least one and optionally more than one other pharmaceutically acceptable chemical components, such as carriers, stabilizers, diluents, dispersing agents, suspending agents, thickening agents, and/or excipients.

The term "respiratory disease," as used herein, refers to diseases affecting the organs that are involved in breathing, such as the nose, throat, larynx, trachea, bronchi, and lungs. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient," as used herein, encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like. Frequently the subject is a human, and may be a human who has been diagnosed as in need of treatment for a disease or disorder disclosed herein.

The term "TLR7 agonist," as used herein, refers to a compound which activates a TLR7 receptor.

The term "TLR7 disease" or a "disease or disorder associated with TLR7 activity," as used herein, refers to any disease state associated with a toll-like receptor. Such diseases or disorders include, but are not limited to, an infectious disease, a viral infectious disease, an inflammatory disease, a respiratory disease, a dermatological disease, an autoimmune disease, a cell-proliferative disease and cancer, such as, by way of example only, asthma, chronic obstructive pulmonary disease (COPD), adult respiratory distress syndrome (ARDS), ulcerative colitis, Crohn's disease, bronchitis, dermatitis, actinic keratosis, basal cell carcinoma, bladder cancer, allergic rhinitis, psoriasis, scleroderma, urticaria, rheumatoid arthritis, multiple sclerosis, cancer, breast cancer, lymphoma, osteosarcoma, melanoma, breast cancer, renal cancer, prostate cancer, colorectal cancer, thyroid cancer, ovarian cancer, pancreatic cancer, neuronal cancer, lung, uterine cancer gastrointestinal cancer, HIV, hepatitis, hepatitis B, hepatitis C, hepatocellular carcinoma or lupus.

The term "therapeutically effective amount," as used herein, refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

The compound names were obtained using ChemDraw Ultra 10.0 (CambridgeSoft®) or JChem version 5.2.2 (ChemAxon).

DESCRIPTION OF THE PREFERRED EMBODIMENTS

Provided herein are compounds and pharmaceutical compositions thereof, which are agonists of toll-like receptor-7 (TLR7). Also are compounds, pharmaceutical compositions and methods for the treatment of diseases and/or disorders associated with TLR7 activity.

The TLR7 agonists of the invention are compounds having the structure of Formula (I), and pharmaceutically acceptable salts, individual isomers and mixture of isomers thereof:

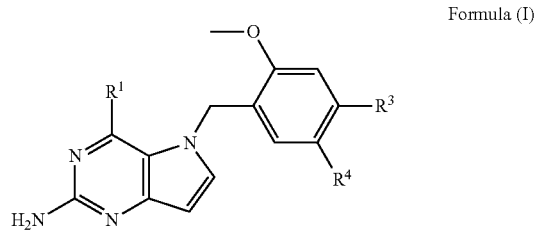

Formula (I)

wherein:
$R^1$ is —$NHR^6$ or —$NHCHR^6R^9$;
$R^3$ is H, -$L_2C(=O)OR^7$, —$C(=O)OL_6R^{12}$, —$C(=O)OL_2R^{12}$, -$L_2C(=O)OL_2R^{12}$, -$L_4C(=O)OL_5OH$, -$L_4R^{12}$, -$L_2C(=O)OL_4C(=O)L_2R^{12}$, -$L_2C(=O)OL_6R^{12}$, -$L_2C(=O)OL_4C(=O)OL_2R^{12}$, -$L_2C(=O)OL_4C(=O)R^{12}$, -$L_4C(=O)OL_2C(=O)R^{12}$, —$CF_2C(=O)R^7$, —$CH=CHC(=O)OL_4C(=O)R^{12}$, —$OL_2C(=O)OL_4C(=O)R^{12}$, —$OL_4C(=O)OL_2R^{12}$, —$OL_4C(=O)OL_2C(=O)R^{12}$ or -$L_2C(=O)OL_3R^{12}$;
$R^4$ is H, -$L_2C(=O)OR^7$, —$C(=O)OL_6R^{12}$, —$C(=O)OL_2R^{12}$, -$L_2C(=O)OL_2R^{12}$, -$L_4C(=O)OL_5OH$, -$L_4R^{12}$, -$L_2C(=O)OL_4C(=O)L_2R^{12}$, -$L_2C(=O)OL_6R^{12}$, -$L_2C(=O)OL_4C(=O)OL_2R^{12}$, -$L_2C(=O)OL_4C(=O)R^{12}$, -$L_4C(=O)OL_2C(=O)R^{12}$, —$CF_2C(=O)R^7$, —$CH=CHC(=O)OL_4C(=O)R^{12}$, —$OL_2C(=O)OL_4C(=O)R^{12}$, —$OL_4C(=O)OL_2R^{12}$, —$OL_4C(=O)OL_2C(=O)R^{12}$ or -$L_2C(=O)OL_3R^{12}$;
where when $R^4$ is H, then $R^3$ is -$L_2C(=O)OR^7$, —$C(=O)OL_6R^{12}$, —$C(=O)OL_2R^{12}$, -$L_2C(=O)OL_2R^{12}$, -$L_4C(=O)OL_5OH$, -$L_4R^{12}$, -$L_2C(=O)OL_4C(=O)L_2R^{12}$, -$L_2C(=O)OL_6R^{12}$, -$L_2C(=O)OL_4C(=O)OL_2R^{12}$, -$L_2C(=O)OL_4C(=O)R^{12}$, -$L_4C(=O)OL_2C(=O)R^{12}$, —$CF_2C(=O)R^7$, —$CH=CHC(=O)OL_4C(=O)R^{12}$, —$OL_2C(=O)OL_4C(=O)R^{12}$, —$OL_4C(=O)OL_2R^{12}$, —$OL_4C(=O)OL_2C(=O)R^{12}$ or -$L_2C(=O)OL_3R^{12}$;
or when $R^3$ is H, then $R^4$ is -$L_2C(=O)OR^7$, —$C(=O)OL_6R^{12}$, —$C(=O)OL_2R^{12}$, -$L_2C(=O)OL_2R^{12}$, -$L_4C(=O)OL_5OH$, -$L_4R^{12}$, -$L_2C(=O)OL_4C(=O)L_2R^{12}$, -$L_2C(=O)OL_6R^{12}$, -$L_2C(=O)OL_4C(=O)OL_2R^{12}$, -$L_2C(=O)OL_4C(=O)R^{12}$, -$L_4C(=O)OL_2C(=O)R^{12}$, —$CF_2C(=O)R^7$, —$CH=CHC(=O)OL_4C(=O)R^{12}$, —$OL_2C(=O)OL_4C(=O)R^{12}$, —$OL_4C(=O)OL_2R^{12}$, —$OL_4C(=O)OL_2C(=O)R^{12}$ or -$L_2C(=O)OL_3R^{12}$;
$L_1$ is —$(CH_2)_m$—; $L_2$ is —$(CH_2)_m$—; $L_3$ is —$(CH_2)_m$—; $L_4$ is —$(CH_2)_m$—; $L_5$ is —$(CH_2)_m$—; $L_6$ is —$(CH_2)_mO(CH_2)_m$—;
$L_9$ is —$(CH_2)_m$—; $R^6$ is —$C_4$-$C_6$alkyl; $R^7$ is —$C_1$-$C_3$alkyl; $R^9$ is $L_1OH$; each $R^{11}$ is independently selected from H or —$C_1$-$C_3$alkyl;
$R^{12}$ is
a) —$N(R^{11})_2$;
b) an unsubstituted 5-6 membered heterocycloalkyl having 1 to 2 heteroatoms independently selected from N and O;
c) a 5-6 membered heterocycloalkyl having 1 to 2 heteroatoms independently selected from N and O substituted with =O;

d) a 5-6 membered heterocycloalkyl having 1 to 2 heteroatoms independently selected from N and O substituted with $C_1$-$C_3$alkyl or —C(=O)O$R^7$;
   or
e) an unsubstituted phenyl;
and each m is independently selected from 1, 2, 3, and 4.

In certain embodiments, the TLR7 agonists of the invention are compounds having the structure of Formula (Ia) or Formula (Ib):

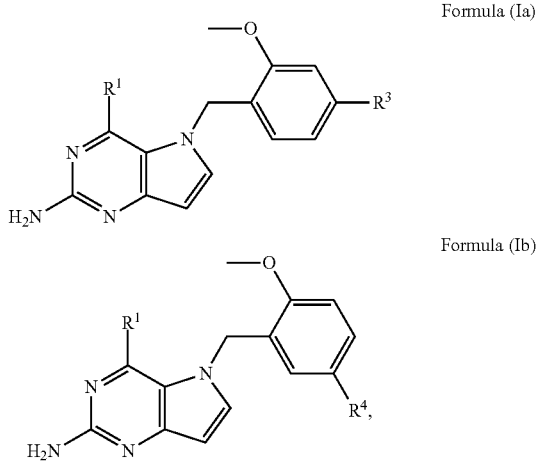

Formula (Ia)

Formula (Ib)

where $R^1$, $R^3$ and $R^4$ are as defined herein.

The compounds of Formula (I), Formula (Ia) and Formula (Ib) provided herein, and the pharmaceutically acceptable salts thereof, also includes all suitable isotopic variations of such compounds, and pharmaceutically acceptable salts. An isotopic variation of a compound or a pharmaceutically acceptable salt thereof is defined as one in which at least one atom is replaced by an atom having the same atomic number but an atomic mass different from the atomic mass usually found in nature. Examples of isotopes that may be incorporated into the compounds and pharmaceutically acceptable salts thereof include but are not limited to isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds, and pharmaceutically acceptable salts
and isomers thereof, are prepared by conventional procedures using appropriate isotopic variations of suitable reagents.

Processes for Making Compounds of Formula (I)

General procedures for preparing compounds of Formula (I), and subformulae thereof, are described in the Examples, infra. In the reactions described, reactive functional groups, for example hydroxy, amino, imino, thio or carboxy groups, where these are desired in the final product, may be protected to avoid their unwanted participation in the reactions. Conventional protecting groups may be used in accordance with standard practice (see e.g., T. W. Greene and P. G. M. Wuts in "Protective Groups in Organic Chemistry," John Wiley and Sons, 1991).

In certain embodiments, the compounds of Formula (I), and subformulae thereof, are prepared as a pharmaceutically acceptable acid addition salt by reacting the free base form of the compound of Formula (I), Formula (Ia) or Formula (Ib) with a pharmaceutically acceptable organic acid or inorganic acid. In other embodiments, a pharmaceutically acceptable base addition salt of compounds of Formula (I), Formula (Ia) or Formula (Ib) is prepared by reacting the free acid form of the compound of Formula (I), Formula (Ia) or Formula (Ib) with a pharmaceutically acceptable organic base or inorganic base. Alternatively, the salt forms of the compounds of Formula (I), Formula (Ia) or Formula (Ib) are prepared using salts of the starting materials or intermediates. In certain embodiments, the compounds of Formula (I), Formula (Ia) or Formula (Ib) are in the form of other salts including, but not limited to, oxalates and trifluoroacetates. In certain embodiments, hemisalts of acids and bases are formed, for example, hemisulphate and hemicalcium salts.

Such pharmaceutically acceptable acid addition salts of compounds of Formula (I), Formula (Ia) or Formula (Ib) include, but are not limited to, a hydrobromide, hydrochloride, sulfate, nitrate, succinate, maleate, formate, acetate, adipate, besylatye, bicarbonate/carbonate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate), hexanoate salt, bisulphate/sulphate, borate, camsylate, cyclamate, edisylate, esylate, gluceptate, gluconate, glucuronate, hexafluorophosphate, hibenzate, hydrochloride/chloride, hydrobromide/bromide, hydroiodide/iodide, isethionate, lactate, malate, malonate, mesylate, methylsulphate, naphthylate, 2-napsylate, nicotinate, orotate, oxalate, palmitate, pamoate, phosphate/hydrogen phosphate/dihydrogen phosphate, pyroglutamate, saccharate, stearate, tannate, tosylate, trifluoroacetate and xinofoate salts.

The organic acid or inorganic acids used to form certain pharmaceutically acceptable acid addition salts of compounds of Formula (I), Formula (Ia) or Formula (Ib) include, but are not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid.

Such pharmaceutically acceptable base addition salt of a compound of Formula (I), Formula (Ia) or Formula (Ib) include, but are not limited to, aluminium, arginine, benzathine, calcium, choline, diethylamine, diolamine, glycine, lysine, magnesium, meglumine, olamine, potassium, sodium, tromethamine and zinc salts.

In certain embodiments, the free acid or free base forms of the compounds of Formula (I) are prepared from the corresponding base addition salt or acid addition salt from, respectively.

For example a compound Formula (I), Formula (Ia) or Formula (Ib) in an acid addition salt form is converted to the corresponding free base by treating with a suitable base (by way of example only, an ammonium hydroxide solution, a sodium hydroxide, and the like). For example, a compound of Formula (I), Formula (Ia) or Formula (Ib) in a base addition salt form is converted to the corresponding free acid by treating with a suitable acid (by way of example only, hydrochloric acid).

In certain embodiments, compounds of Formula (I), Formula (Ia) or Formula (Ib) are prepared as protected derivatives using methods known to those of ordinary skill in the art. A detailed description of the techniques applicable to the creation of protecting groups and their removal can be found in T. W. Greene, "Protecting Groups in Organic Chemistry," 3$^{rd}$ edition, John Wiley and Sons, Inc., 1999.

In certain embodiments, compounds of Formula (I), Formula (Ia) and Formula (Ib) are prepared as their individual stereoisomers. In other embodiments, the compounds of Formula (I), Formula (Ia) and Formula (Ib) are prepared as their individual stereoisomers by reacting a racemic mixture of the compound with an optically active resolving agent to form a pair of diastereoisomeric compounds, separating the diastereomers and recovering the optically pure enantiomers. In certain embodiments, resolution of enantiomers is carried out using covalent diastereomeric derivatives of the compounds of Formula (I), Formula (Ia) or Formula (Ib), or by using dissociable complexes (e.g., crystalline diastereomeric salts). Diastereomers have distinct physical properties (e.g., melting points, boiling points, solubility, reactivity, etc.) and are readily separated by taking advantage of these dissimilarities. In certain embodiments, the diastereomers are separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981.

A non-limiting example of a synthetic scheme used to make compounds of Formula (I) is illustrated in reaction scheme (I) below.

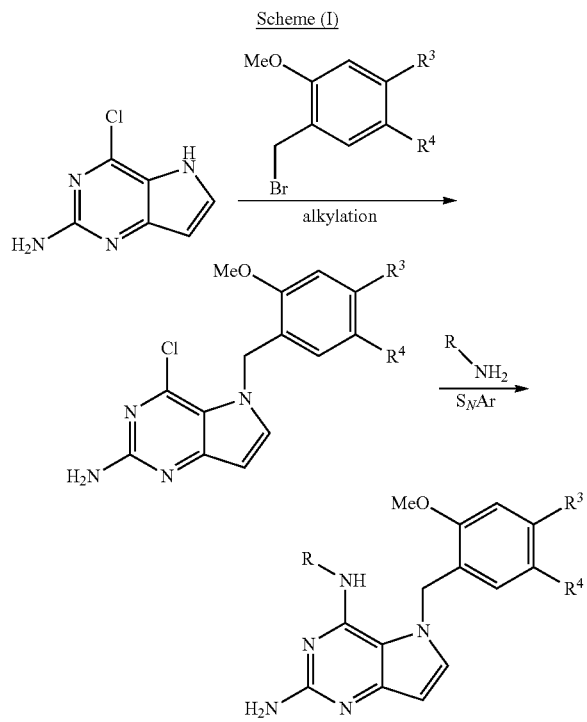

Scheme (I) illustrates the synthesis of pyrrolopyrimidines of Formula (I) using a two-step scheme starting with commercially available 4-chloro-5H-pyrrolo[3,2-d]pyrimidin-2-amine. Alkylation at the N-5 position by a benzylbromide (or benzylchloride) analog gives the corresponding 5-benzyl derivatives, where $R^3$ and $R^4$ are as defined herein. Subsequent S$_N$Ar substitution of the chloro group by an alkyl amine derivative affords the corresponding 4,5-disubstituted pyrrolopyrimidine, where R is $R^6$ or —CHR$^6$R$^9$ and $R^6$ and $R^9$ are as defined herein.

Pharmacology and Utility

When a foreign antigen challenges the immune system it responds by launching a protective response that is characterized by the coordinated interaction of both the innate and acquired immune systems. These two interdependent systems fulfill two mutually exclusive requirements: speed (contributed by the innate system) and specificity (contributed by the adaptive system).

The innate immune system serves as the first line of defense against invading pathogens, holding the pathogen in check while the adaptive responses are matured. It is triggered within minutes of infection in an antigen-independent fashion, responding to broadly conserved patterns in the pathogens (though it is not non-specific, and can distinguish between self and pathogens). Crucially, it also generates the inflammatory and co-stimulatory milieu (sometimes referred to as the danger signal) that potentiates the adaptive immune system and steers (or polarizes it) towards the cellular or humoral responses most appropriate for combating the infectious agent. The development of TLR modulators for therapeutic targeting of innate immunity has been reviewed (see *Nature Medicine*, 2007, 13, 552-559; *Drug Discovery Today: Therapeutic Stateqies*, 2006, 3, 343-352 and *Journal of Immunology*, 2005, 174, 1259-1268).

The adaptive response becomes effective over days or weeks, but ultimately provides the fine antigenic specificity required for complete elimination of the pathogen and the generation of immunologic memory. It is mediated principally by T and B cells that have undergone germline gene rearrangement and are characterized by specificity and long-lasting memory. However, it also involves the recruitment of elements of the innate immune system, including professional phagocytes (macrophages, neutrophils etc.) and granulocytes (basophils, eosinophils etc.) that engulf bacteria and even relatively large protozoal parasites. Once an adaptive immune response has matured, subsequent exposure to the pathogen results in its rapid elimination due to highly specific memory cells have been generated that are rapidly activated upon subsequent exposure to their cognate antigen.

Autoimmune diseases, are defined by (i) humoral or autoantibody response to a self antigen (by way of example only, Graves' primary hyperthyroidism with antibodies to the TSH receptor), or (ii) cellular response wherein immune cells destroy nonimmune cells from which the self-antigen is derived (by way of example only, the thyrocyte (Hashimoto's thyroiditis) or pancreatic □-islet cell (Type 1 diabetes). Many autoimmune diseases are a combination of both phenomena, for instance, Hashimoto's and Type 1 diabetes also have auto-antibodies, anti-thyroid peroxidase (TPO) or anti-glutamic acid decarboxylase (GAD)/Islet Cell. Autoimmune diseases often have an inflammatory component including, but not limited to, increases in adhesion molecules (by way of example only, vascular cell adhesion molecule-1 (VCAM-1), and altered leukocyte adhesion to the vasculature such as, by way of example only, colitis, systemic lupus, systemic sclerosis, and the vascular complications of diabetes.

Toll-like receptors (TLRs) are type-I transmembrane proteins characterized by an extracellular N-terminal leucine-rich repeat (LRR) domain, followed by a cysteine-rich region, a TM domain, and an intracellular (cytoplasmic) tail that contains a conserved region named the Toll/IL-1 receptor (TIR) domain. TLRs are pattern recognition receptors (PRR) that are expressed predominantly on immune cells including, but not limited to, dendritic cells, T lymphocytes, macrophages, monocytes and natural killer cells. The LLR domain is important for ligand binding and associated signaling and is a common feature of PRRs. The TIR domain is important in protein-protein interactions and is associated with innate immunity. The TIR domain also unites a larger IL-1 R/TLR superfamily that is composed of three subgroups. Members of the first group possess immunoglobin domains in their extracellular regions and include IL-1 and IL-18 receptors and accessory proteins as well as ST2. The second group encompasses the TLRs. The third group includes intracellular adaptor proteins important for signaling.

TLRs are a group of pattern recognition receptors which bind to pathogen-associated molecular patterns (PAMPS) from bacteria, fungi, protozoa and viruses, and act as a first line of defense against invading pathogens. TLRs are essential to induce expression of genes involved in inflammatory responses, and TLRs and the innate immune system are a critical step in the development of antigen-specific acquired immunity.

Adaptive (humoral or cell-mediated) immunity is associated with the TLR signal mechanism of innate immunity. Innate immunity is a protective immune cell response that functions rapidly to fight environmental insults including, but not limited to, bacterial or viral agents. Adaptive immunity is a slower response, which involves differentiation and activation of naive T lymphocytes into T helper 1 (Th1) or T helper 2 (Th2) cell types. Th1 cells mainly promote cellular immunity, whereas Th2 cells mainly promote humoral immunity. Though primarily a host protective system, pathologic expression of the innate immunity signals emanating from the TLR pathway are implicated in initiating autoimmune-inflammatory diseases.

All TLRs appear to function as either a homodimer or heterodimer in the recognition of a specific, or set of specific, molecular determinants present on pathogenic organisms including bacterial cell-surface lipopolysaccharides, lipoproteins, bacterial flagellin, DNA from both bacteria and viruses and viral RNA. The cellular response to TLR activation involves activation of one or more transcription factors, leading to the production and secretion of cytokines and co-stimulatory molecules such as interferons, TNF—, interleukins, MIP-1 and MCP-1 which contribute to the killing and clearance of the pathogenic invasion.

TLR spatial expression is coincident with the host's environmental interface. While only a few other Toll-like proteins have been cloned in *Drosophila*, the human TLR family is composed of at least 11 members, TLR1 through TLR11, that elicit overlapping yet distinct biological responses due to differences in cellular expression and signaling pathways they initiate. Each of the TLRs is expressed on a different subset of leukocytes and each of the TLRs is specific in its expression patterns and PAMP sensitivities and detects different subsets of pathogens allowing vigilant surveillance by the immune system.

Toll-Like Receptor 7 (TLR7)

TLR7 maps to human chromosome Xp22, and the TLR7 sequence encodes a 1049 (aa) protein containing 27 N-terminal LRRs with a calculated molecular weight of 121 kDa. TLR7 is most closely related to TLR8 and TLR9 with 43% and 36% overall (aa) sequence identity, respectively.

In vivo, TLR7 mRNA is expressed in lung, placenta, spleen, lymph node, and tonsil. TLR7 mRNA expression is highest in monocytes, B cells, and plasmocytoid dendritic cells. In vitro, TLR7 mRNA expression is upregulated in THP-1 cells upon PMA-induced differentiation. TLR7 is highly upregulated by exposure to IL-6 and to a slightly lesser extent by autocrine IFN-γ, IL-1β. TLR7 mRNA expression in THP-1 cells is elevated after exposure to both Gram-positive and Gram-negative bacteria. Ex vivo, expression of TLR7 is elevated after exposure to both Gram-positive and Gram-negative bacteria in monocytes and to a greater degree in granulocytes. TLR7 is expressed in the endosome. The role of TLR7, is to detect the presence of "foreign" single-stranded RNA within a cell, as a means to respond to viral invasion. TLR7 is a structurally highly conserved protein which recognizes guanosine- or uridine-rich, single-stranded RNA (ssRNA) from viruses such as human immunodeficiency virus, vesicular stomatitis virus and influenza virus. Thus, through activation of dendritic cells and other antigen-presenting cells, TLR7 engagement and resulting cytokine production is expected to activate diverse innate and acquired immune response mechanisms leading to the destruction of pathogens, infected cells or tumor cells.

Compounds of Formula (I), Formula (Ia) or Formula (Ib), pharmaceutically acceptable salts and isomers thereof, pharmaceutical compositions, and/or combinations are agonists of toll-like receptor 7 activity, and are used in the treatment of diseases and/or disorders associated with such TLR7 receptors.

In certain embodiments, the compounds of Formula (I), Formula (Ia) or Formula (Ib), pharmaceutically acceptable salts and isomers thereof, pharmaceutical compositions, and/or combinations are used in the treatment of respiratory diseases and/or disorders including, but not limited to, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

In certain embodiments, the compounds of Formula (I), Formula (Ia) or Formula (Ib), pharmaceutically acceptable salts and isomers thereof, pharmaceutical compositions, and/or combinations are used in the treatment of dermatological disorders including, but not limited to, psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, basal cell carcinoma, actinic keratosis, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

In certain embodiments, the compounds of Formula (I), Formula (Ia) or Formula (Ib), pharmaceutically acceptable salts and isomers thereof, pharmaceutical compositions, and/or combinations are used in the treatment of ocular diseases and/or disorders including, but not limited to, blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial.

In certain embodiments, the compounds of Formula (I), Formula (Ia) or Formula (Ib), pharmaceutically acceptable salts and isomers thereof, pharmaceutical compositions, and/or combinations are used in the treatment of other auto-immune and allergic disorders including, but not limited to, rheumatoid arthritis, irritable bowel syndrome, systemic lupus erythematosus, multiple sclerosis, Hashimoto's thyroiditis, Crohn's disease, inflammatory bowel disease (IBD), Graves' disease, Addison's disease, diabetes mellitus, idiopathic thrombocytopaenic purpura, eosinophilic fasciitis, hyper-IgE syndrome, antiphospholipid syndrome and Sazary syndrome.

In certain embodiments, the compounds of Formula (I), Formula (Ia) or Formula (Ib), pharmaceutically acceptable salts and isomers thereof, and pharmaceutical compositions are used in the treatment of cancer including, but not limited to, bladder, prostate, breast, colorectal, liver, hepatocellular carcinoma, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumor recurrences, and paraneoplastic syndromes. In certain embodiments, the compounds of Formula (I), Formula (Ia) or Formula (Ib), pharmaceutically acceptable salts and isomers thereof, and pharmaceutical compositions are useful as modulators of toll-like receptor activity, and are used in the treatment of neoplasias including, but not limited to, basal cell carcinoma, squamous cell carcinoma, actinic keratosis, melanoma, carcinomas, sarcomas, leukemias, renal cell carcinoma, Kaposi's sarcoma, myelogeous leukemia, chronic lymphocytic leukemia and multiple myeloma.

In certain embodiments, the compounds of Formula (I), Formula (Ia) or Formula (Ib), pharmaceutically acceptable salts and isomers thereof, pharmaceutical compositions, and/or combinations are used in the treatment of infectious diseases including, but not limited to, viral infectious diseases such as genital warts, common warts, plantar warts, respiratory syncytial virus (RSV), hepatitis B, hepatitis C, Dengue virus, herpes simplex virus (by way of example only, HSV-I, HSV-II, CMV, or VZV), molluscum contagiosum, vaccinia, variola, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza, parainfluenza, mumps virus, measles virus, papovavirus, hepadnavirus, flavivirus, retrovirus, arenavirus (by way of example only, LCM, Junin virus, Machupo virus, Guanarito virus and Lassa Fever) and filovirus (by way of example only, ebola virus or marbug virus).

In certain embodiments, the compounds of Formula (I), Formula (Ia) or Formula (Ib), pharmaceutically acceptable salts and isomers thereof, pharmaceutical compositions, and/or combinations are used in the treatment of bacterial, fungal, and protozoal infections including, but not limited to, tuberculosis and *Mycobacterium avium*, leprosy; *Pneumocystis carnii*, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus,* and *Chlamydia,* and fungal infections such as candidiasis, aspergillosis, histoplasmosis, cryptococcal meningitis.

Administration and Pharmaceutical Compositions

For the therapeutic uses of compounds of Formula (I), Formula (Ia) and Formula (Ib), or pharmaceutically acceptable salts and isomers thereof, such compounds are administered in therapeutically effective amounts either alone or as part of a pharmaceutical composition. Accordingly, such pharmaceutical compositions, comprise a compound of Formula (I), Formula (Ia) or Formula (Ib), or pharmaceutically acceptable salt thereof, and one or more pharmaceutically acceptable carriers, diluents, or excipients. In addition, such compounds and compositions are administered singly or in combination with one or more additional therapeutic agents. The method of administration of such compounds and compositions include, but are not limited to, oral administration, rectal administration, parenteral, intravenous administration, intravitreal administration, intramuscular administration, inhalation, intranasal administration, topical administration, ophthalmic administration or otic administration.

The therapeutically effective amount will vary depending on, among others, the disease indicated, the severity of the disease, the age and relative health of the subject, the potency of the compound administered, the mode of administration and the treatment desired. In certain embodiments, the daily dosage of a compound of Formula (I), Formula (Ia) or Formula (Ib), satisfactory results are indicated to be obtained systemically at daily dosages of from about 0.03 to 2.5 mg/kg per body weight. In certain embodiments, the daily dosage of a compound of Formula (I), Formula (Ia) or Formula (Ib), administered by inhalation, is in the range from 0.05 micrograms per kilogram body weight (µg/kg) to 100 micrograms per kilogram body weight (µg/kg). In certain embodiments, the quantit of a compound of Formula (I), Formula (Ia) or Formula (Ib) per dose administered by inhalation, is in the range from 10 ng to 500 ng. In other embodiments, the daily dosage of a compound of Formula (I), Formula (Ia) or Formula (Ib), administered orally, is in the range from 0.01 micrograms per kilogram body weight (µg/kg) to 100 milligrams per kilogram body weight (mg/kg). An indicated daily dosage in the larger mammal, e.g. humans, is in the range from about 0.5 mg to about 100 mg of a compound of Formula (I), conveniently administered, e.g. in divided doses up to four times a day or in controlled release form. In certain embodiment, unit dosage forms for oral administration comprise from about 1 to 50 mg of a compound of Formula (I), Formula (Ia) or Formula (Ib).

Other aspects provided herein are processes for the preparation of pharmaceutical composition which comprise a compound of Formula (I), Formula (Ia) or Formula (Ib), or pharmaceutically acceptable salt thereof. In certain embodiments, such processes include admixing a compound of the Formula (I), Formula (Ia) or Formula (Ib), or pharmaceutically acceptable salts thereof, with one or more pharmaceutically acceptable carriers, diluents or excipients. In certain embodiments, the pharmaceutical compositions comprising a compound of Formula (I), Formula (Ia) or Formula (Ib), in free form or in a pharmaceutically acceptable salt form, in association with at least one pharmaceutically acceptable carrier, diluent or excipient are manufactured by mixing, granulating and/or coating methods. In other embodiments, such compositions are optionally contain excipients, such as preserving, stabilizing, wetting or emulsifying agents, solution promoters, salts for regulating the osmotic pressure and/or buffers. In other embodiments, such compositions are sterilized.

Oral Dosage Forms

In certain embodiments, the pharmaceutical compositions containing a compound of Formula (I), Formula (Ia) or Formula (Ib), or pharmaceutically acceptable salt thereof, are administered orally as discrete dosage forms, wherein such dosage forms include, but are not limited to, capsules, gelatin capsules, caplets, tablets, chewable tablets, powders, granules, syrups, flavored syrups, solutions or suspensions in aqueous or non-aqueous liquids, edible foams or whips, and oil-in-water liquid emulsions or water-in-oil liquid emulsions.

The capsules, gelatin capsules, caplets, tablets, chewable tablets, powders or granules, used for the oral administration of a compound of Formula (I), Formula (Ia) or Formula (Ib), or pharmaceutically acceptable salt thereof, are prepared by admixing a compound of Formula (I), Formula (Ia) or Formula (Ib), or pharmaceutically acceptable salt thereof, together with at least one excipient using conventional pharmaceutical compounding techniques. Non-limiting examples of excipients used in oral dosage forms described herein include, but are not limited to, binders, fillers, disintegrants, lubricants, absorbents, colorants, flavors, preservatives and sweeteners.

Non-limiting examples of such binders include, but are not limited to, corn starch, potato starch, starch paste, pre-gelatinized starch, or other starches, sugars, gelatin, natural and synthetic gums such as acacia, sodium alginate, alginic acid, other alginates, tragacanth, guar gum, cellulose and its derivatives (by way of example only, ethyl cellulose, cellulose acetate, carboxymethyl cellulose calcium, sodium carboxymethylcellulose, methyl cellulose, hydroxypropyl methylcellulose and microcrystalline cellulose), magnesium aluminum silicate, polyvinyl pyrrolidone and combinations thereof.

Non-limiting examples of such fillers include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. In certain embodiments, the binder or filler in pharmaceutical compositions are present in from about 50 to about 99 weight percent of the pharmaceutical composition or dosage form.

Non-limiting examples of such disintegrants include, but are not limited to, agar-agar, alginic acid, sodium alginate, calcium carbonate, sodium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and combinations thereof. In certain embodiments, the amount of disintegrant used in the pharmaceutical compositions is from about 0.5 to about 15 weight percent of disintegrant, while in other embodiments the amount is from about 1 to about 5 weight percent of disintegrant.

Non-limiting examples of such lubricants include, but are not limited to, sodium stearate, calcium stearate, magnesium stearate, stearic acid, mineral oil, light mineral oil, glycerin, sorbitol, mannitol, polyethylene glycol, other glycols, sodium lauryl sulfate, talc, hydrogenated vegetable oil (by way of example only, peanut oil, cottonseed oil, sunflower oil, sesame oil, olive oil, corn oil, and soybean oil), zinc stearate, sodium oleate, ethyl oleate, ethyl laureate, agar, silica, a syloid silica gel (AEROSIL 200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.) and combinations thereof. In certain embodiments, the amount of lubricants used in the pharmaceutical compositions is in an amount of less than about 1 weight percent of the pharmaceutical compositions or dosage forms.

Non-limiting examples of such diluents include, but are not limited to, lactose, dextrose, sucrose, mannitol, sorbitol, cellulose, glycine or combinations thereof.

In certain embodiments, tablets and capsules are prepared by uniformly admixing a compound of Formula (I), Formula (Ia) or Formula (Ib), or pharmaceutically acceptable salt thereof, with liquid carriers, finely divided solid carriers, or both, and then shaping the product into the desired presentation if necessary. In certain embodiments, tablets are prepared by compression. In other embodiments, tablets are prepared by molding.

In certain embodiments, a compound of Formula (I), Formula (Ia) or Formula (Ib), or pharmaceutically acceptable salt thereof, is orally administered as a controlled release dosage form. Such dosage forms are used to provide slow or controlled-release of a compound of Formula (I), Formula (Ia) or Formula (Ib), or pharmaceutically acceptable salt thereof. Controlled release is obtained using, for example, hydroxypropylmethyl cellulose, other polymer matrices, gels, permeable membranes, osmotic systems, multilayer coatings, microparticles, liposomes, microspheres, or a combination thereof. In certain embodiments, controlled-release dosage forms are used to extend activity of the compound of Formula (I), reduce dosage frequency, and increase patient compliance.

Administration of compounds of Formula (I) as oral fluids such as solution, syrups and elixirs are prepared in unit dosage forms such that a given quantity of solution, syrups or elixirs contains a predetermined amount of a compound of Formula (I). Syrups are prepared by dissolving the compound in a suitably flavored aqueous solution, while elixirs are prepared through the use of a non-toxic alcoholic vehicle. Suspensions are formulated by dispersing the compound in a non-toxic vehicle. Non-limiting examples of excipients used in as oral fluids for oral administration include, but are not limited to, solubilizers, emulsifiers, flavoring agents, preservatives, and coloring agents. Non-limiting examples of solubilizers and emulsifiers include, but are not limited to, water, glycols, oils, alcohols, ethoxylated isostearyl alcohols and polyoxy ethylene sorbitol ethers. Non-limiting examples of preservatives include, but are not limited to, sodium benzoate. Non-limiting examples of flavoring agents include, but are not limited to, peppermint oil or natural sweeteners or saccharin or other artificial sweeteners.

Parenteral Dosage Forms

In certain embodiments pharmaceutical compositions containing a compound of Formula (I), Formula (Ia) or Formula (Ib), or pharmaceutically acceptable salt thereof, are administered parenterally by various routes including, but not limited to, subcutaneous, intravenous (including bolus injection), intramuscular, and intraarterial.

Such parenteral dosage forms are administered in the form of sterile or sterilizable injectable solutions, suspensions, dry and/or lyophylized products ready to be dissolved or suspended in a pharmaceutically acceptable vehicle for injection (reconstitutable powders) and emulsions. Vehicles used in such dosage forms include, but are not limited to, Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Transdermal Dosage Forms

In certain embodiments pharmaceutical compositions containing a compound of Formula (I), Formula (Ia) or Formula (Ib), or pharmaceutically acceptable salt thereof, are administered transdermally. Such transdermal dosage forms include "reservoir type" or "matrix type" patches, which are applied to the skin and worn for a specific period of time to permit the penetration of a desired amount of a compound of Formula (I). By way of example only, such transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. In other embodiments, matrix transdermal formulations are used.

Formulations for transdermal delivery of a compound of Formula (I) include an effective amount of a compound of Formula (I), a carrier and an optional diluent. A carrier includes, but is not limited to, absorbable pharmacologically acceptable solvents to assist passage through the skin of the host, such as water, acetone, ethanol, ethylene glycol, propylene glycol, butane-1,3-diol, isopropyl myristate, isopropyl palmitate, mineral oil, and combinations thereof.

In certain embodiments, such transdermal delivery systems include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In other embodiments, the pH of such a transdermal pharmaceutical composition or dosage form, or of the tissue to which the pharmaceutical composition or dosage form is applied, is adjusted to improve delivery of one or more compounds of Formula (I). In other embodiments, the polarity of a solvent carrier, its ionic strength, or tonicity are adjusted to improve delivery. In other embodiments, compounds such as stearates are added to advantageously alter the hydrophilicity or lipophilicity of one or more compounds of Formula (I) so as to improve delivery.

In certain embodiments, such stearates serve as a lipid vehicle for the formulation, as an emulsifying agent or surfactant, and as a delivery-enhancing or penetration-enhancing agent. In other embodiments, different salts, hydrates s of the compounds of Formula (I) are used to further adjust the properties of the resulting composition.

Topical Dosage Forms

In certain embodiments a compound of Formula (I), Formula (Ia) or Formula (Ib), or pharmaceutically acceptable salt thereof, is administered by topical application of pharmaceutical composition containing a compound of Formula (I), Formula (Ia) or Formula (Ib), or pharmaceutically acceptable salt thereof, in the form of lotions, gels, ointments solutions, emulsions, suspensions or creams. Suitable formulations for topical application to the skin are aqueous solutions, ointments, creams or gels, while formulations for ophthalmic administration are aqueous solutions. Such formulations optionally contain solubilizers, stabilizers, tonicity enhancing agents, buffers and preservatives.

Such topical formulations include at least one carrier, and optionally at least one diluent. Such carriers and diluents include, but are not limited to, water, acetone, ethanol, ethylene glycol, propylene glycol, butane-1,3-diol, isopropyl myristate, isopropyl palmitate, mineral oil, and combinations thereof.

In certain embodiments, such topical formulations include penetration enhancers to assist in delivering one or more compounds of Formula (I) to the tissue. Such penetration enhancers include, but are not limited to, acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

In certain embodiments pharmaceutical compositions containing a compound of Formula (I), Formula (Ia) or Formula (Ib), or pharmaceutically acceptable salt thereof, are administered by inhalation. Dosage forms for inhaled administration are formulated as aerosols or dry powders. Aerosol formulations for inhalation administration comprise a solution or fine suspension of a compound of Formula (I), Formula (Ia) or Formula (Ib), or pharmaceutically acceptable salt thereof, in a pharmaceutically acceptable aqueous or non-aqueous solvent. In addition, such pharmaceutical compositions optionally comprise a powder base such as lactose, glucose, trehalose, mannitol or starch, and optionally a performance modifier such as L-leucine or another amino acid, and/or metals salts of stearic acid such as magnesium or calcium stearate.

In certain embodiments, compounds of Formula (I) are be administered directly to the lung by inhalation using a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas, or a Dry Powder Inhaler (DPI) device which uses a burst of gas to create a cloud of dry powder inside a container, which is then be inhaled by the patient. In certain embodiments, capsules and cartridges of gelatin for use in an inhaler or insufflator are formulated containing a powder mixture of a compound of Formula (I) and a powder base such as lactose or starch. In certain embodiments, compounds of Formula (I) are delivered to the lung using a liquid spray device, wherein such devices use extremely small nozzle holes to aerosolize liquid drug formulations that can then be directly inhaled into the lung. In other embodiments, compounds of Formula (I) are delivered to the lung using a nebulizer device, wherein a nebulizers creates an aerosols of liquid drug formulations by using ultrasonic energy to form fine particles that can be readily inhaled. In other embodiments, compounds of Formula (I) are delivered to the lung using an electrohydrodynamic ("EHD") aerosol device wherein such EHD aerosol devices use electrical energy to aerosolize liquid drug solutions or suspensions.

In certain embodiments, the pharmaceutical composition containing a compound of Formula (I), Formula (Ia) or Formula (Ib), or pharmaceutically acceptable salts thereof, described herein, also contain one or more absorption enhancers. In certain embodiments, such absorption enhancers include, but are not limited to, sodium glycocholate, sodium caprate, N-lauryl-β-D-maltopyranoside, EDTA, and mixed micelles.

In certain embodiments the pharmaceutical composition containing a compound of Formula (I), Formula (Ia) or Formula (Ib), or a pharmaceutically acceptable salt thereof, are administered nasally. The dosage forms for nasal administration are formulated as aerosols, solutions, drops, gels or dry powders.

In certain embodiments the pharmaceutical composition containing a compound of Formula (I), Formula (Ia) or Formula (Ib), or a pharmaceutically acceptable salt thereof, are administered rectally in the form of suppositories, enemas, ointment, creams rectal foams or rectal gels. In certain embodiments such suppositories are prepared from fatty emulsions or suspensions, cocoa butter or other glycerides.

In certain embodiments the pharmaceutical composition containing a compound of Formula (I), Formula (Ia) or Formula (Ib), or a pharmaceutically acceptable salt thereof, are administered opthamically as eye drops. Such formulations are aqueous solutions that optionally contain solubilizers, stabilizers, tonicity enhancing agents, buffers and preservatives.

In certain embodiments the pharmaceutical composition containing a compound of Formula (I), Formula (Ia) or Formula (Ib), or a pharmaceutically acceptable salt thereof, are administered optically as ear drops. Such formulations are aqueous solutions that optionally contain solubilizers, stabilizers, tonicity enhancing agents, buffers and preservatives.

In certain embodiments the pharmaceutical composition containing a compound of Formula (I), Formula (Ia) or Formula (Ib), or a pharmaceutically acceptable salt thereof, are formulated as a depot preparation. Such formulations are administered by implantation (for example subcutaneously or intramuscularly) or by intramuscular injection. In certain embodiments, such formulations include polymeric or hydrophobic materials (for example, as an emulsion in an acceptable oil) or ion exchange resins, or as sparingly soluble derivatives, for example, as a sparingly soluble salt.

In a further embodiment, the pharmaceutical compositions comprising a compound of Formula (I), Formula (Ia) or Formula (Ib), or pharmaceutically acceptable salt thereof, are adapted for oral administration for the treatment of viral infectious diseases and/or disorders associated with TLR7 activity.

In a further embodiment, the pharmaceutical compositions comprising a compound of Formula (I), Formula (Ia) or Formula (Ib), or pharmaceutically acceptable salt thereof, are adapted for intramuscular administration for the treatment of viral infectious diseases and/or disorders associated with TLR7.

In a further embodiment, the pharmaceutical compositions comprising a compound of Formula (I), Formula (Ia) or Formula (Ib), or pharmaceutically acceptable salt thereof, are adapted for oral administration for the treatment of infectious diseases and/or disorders associated with TLR7.

In a further embodiment, the pharmaceutical compositions comprising a compound of Formula (I), Formula (Ia) or Formula (Ib), or pharmaceutically acceptable salt thereof, are adapted for oral administration for the treatment of bacterial diseases and/or disorders associated with TLR7.

In a further embodiment, the pharmaceutical compositions comprising a compound of Formula (I), Formula (Ia) or Formula (Ib), or pharmaceutically acceptable salt thereof, are adapted for oral administration for the treatment of fungal diseases and/or disorders associated with TLR7.

In a further embodiment, the pharmaceutical compositions comprising a compound of Formula (I), Formula (Ia) or Formula (Ib), or pharmaceutically acceptable salt thereof, are adapted for oral administration for the treatment of cancer associated with TLR7.

In a further embodiment, the pharmaceutical compositions comprising a compound of Formula (I), Formula (Ia) or Formula (Ib), or pharmaceutically acceptable salt thereof, are adapted for intravenous administration for the treatment of cancer associated with TLR7.

In a further embodiment, the pharmaceutical compositions comprising a compound of Formula (I), Formula (Ia) or Formula (Ib), or pharmaceutically acceptable salt thereof, are adapted for administration as eye drops for the treatment of ophthalmic diseases and/or disorders associated with TLR7.

In a further embodiment, the pharmaceutical compositions comprising a compound of Formula (I), Formula (Ia) or Formula (Ib), or pharmaceutically acceptable salt thereof, are adapted for topical administration for the treatment of dermatological diseases and/or disorders associated with TLR7.

In a further embodiment, the pharmaceutical compositions comprising a compound of Formula (I), Formula (Ia) or Formula (Ib), or pharmaceutically acceptable salt thereof, are adapted for topical administration for the treatment of actinic keratosis. In a further embodiment, the pharmaceutical compositions comprising a compound of Formula (I), Formula (Ia) or Formula (Ib), or pharmaceutically acceptable salt thereof, are adapted for topical administration as a cream for the treatment of actinic keratosis.

In a further embodiment, the pharmaceutical compositions comprising a compound of Formula (I), Formula (Ia) or Formula (Ib), or pharmaceutically acceptable salt thereof, are adapted for topical administration for the treatment of basal cell carcinoma. In a further embodiment, the pharmaceutical compositions comprising a compound of Formula (I), Formula (Ia) or Formula (Ib), or pharmaceutically acceptable salt thereof, are adapted for topical administration as a cream for the treatment of basal cell carcinoma.

In a further embodiment, the pharmaceutical compositions comprising a compound of Formula (I), Formula (Ia) or Formula (Ib), or pharmaceutically acceptable salt thereof, are adapted for administration by inhalation for the treatment of respiratory diseases and/or disorders associated with TLR7. In certain embodiments, the respiratory disease is allergic asthma.

Provided herein are compounds of Formula (I), Formula (Ia) or Formula (Ib), and pharmaceutically acceptable salts thereof, and the pharmaceutical composition containing a compound of Formula (I), Formula (Ia) or Formula (Ib), or a pharmaceutically acceptable salts thereof, and/or pharmaceutically acceptable salts thereof, for use in activating TLR7 activity, and thereby are used to in the prevention or treatment of diseases and/or disorders associated with TLR7 activity. Such compounds of Formula (I) and pharmaceutically acceptable salts thereof, and pharmaceutical compositions are agonists of TLR7.

Also are methods for the treatment of a subject suffering from a disease and/or disorder associated with TLR7 activity, wherein the methods include administering to the subject an effective amount of a compound of Formula (I) or a pharmaceutically acceptable salt thereof, either alone or as part of a pharmaceutical composition as described herein.

Provided herein is the use of a compound of Formula (I), or a pharmaceutically acceptable salt thereof, in the preparation of a medicament for the treatment of a disease or disorder associated with TLR7 activity.

Combination Treatment

In certain embodiments, a compound of Formula (I), or a pharmaceutically acceptable salt thereof, or a pharmaceutical composition containing a compound of Formula (I), Formula (Ia) or Formula (Ib), or pharmaceutically acceptable salt thereof, is administered alone (without an additional therapeutic agent) for the treatment of one or more of the disease and/or disorders associated with TLR7 activity described herein.

In other embodiments, a compound of Formula (I), or a pharmaceutically acceptable salt thereof, or a pharmaceutical composition containing a compound of Formula (I), Formula (Ia) or Formula (Ib), or pharmaceutically acceptable salt thereof, is administered in combination with one or more additional therapeutic agents, for the treatment of one or more of the disease and/or disorders associated with TLR7 activity described herein.

In other embodiments, a compound of Formula (I), or a pharmaceutically acceptable salt thereof, or a pharmaceutical composition containing a compound of Formula (I), Formula (Ia) or Formula (Ib), or pharmaceutically acceptable salt thereof, is formulated in combination with one or more additional therapeutic agents and administered for the treatment of one or more of the disease and/or disorders associated with TLR7 activity described herein.

In other embodiments, a compound of Formula (I), or a pharmaceutically acceptable salt thereof, or a pharmaceutical composition containing a compound of Formula (I), Formula (Ia) or Formula (Ib), or pharmaceutically acceptable salt thereof, is administered sequentially with one or more additional therapeutic agents, for the treatment of one or more of the disease and/or disorders associated with TLR7 activity described herein.

In other embodiments, the combination treatments include administration of a compound of Formula (I), or a pharmaceutically acceptable salt thereof, or a pharmaceutical composition containing a compound of Formula (I), prior to administration of one or more additional therapeutic agents, for the treatment of one or more of the disease and/or disorders associated with TLR7 activity described herein.

In other embodiments, the combination treatments include administration of a compound of Formula (I), or a pharmaceutically acceptable salt thereof, or a pharmaceutical composition containing a compound of Formula (I), subsequent to administration of one or more additional therapeutic agents, for the treatment of one or more of the disease and/or disorders associated with TLR7 activity described herein.

In certain embodiments, the combination treatments include administration of a compound of Formula (I), or a pharmaceutically acceptable salt thereof, or a pharmaceutical composition containing a compound of Formula (I), concurrently with one or more additional therapeutic agents, for the treatment of one or more of the disease and/or disorders associated with TLR7 activity described herein.

In certain embodiments, the combination treatments include administration of a compound of Formula (I), or a pharmaceutically acceptable salt thereof, or a pharmaceutical composition containing a compound of Formula (I) formulated with one or more additional therapeutic agents, for the treatment of one or more of the disease and/or disorders associated with TLR7 activity described herein.

In certain embodiments of the combination therapies described herein, the compounds of Formula (I), Formula (Ia) or Formula (Ib), or a pharmaceutically acceptable salt thereof, and the additional therapeutics agent(s) act additively. In certain embodiments of the combination therapies described herein, the compounds of Formula (I), or pharmaceutically acceptable salts thereof, and the additional therapeutics agent(s) act synergistically.

In other embodiments, a compound of Formula (I), Formula (Ia) or Formula (Ib), or a pharmaceutically acceptable salt thereof, or a pharmaceutical composition containing a compound of Formula (I), Formula (Ia) or Formula (Ib), or pharmaceutically acceptable salt thereof, is administered to a patient who has not previously undergone or is not currently undergoing treatment with another therapeutic agent.

The additional therapeutic agents used in combination with a compound of Formula (I), Formula (Ia) or Formula (Ib), or a pharmaceutically acceptable salt thereof, include, but are not limited to antibiotics or antibacterial agents, antiemetic agents, antifungal agents, anti-inflammatory agents, antiviral agents, viral enzyme inhibitors or anticancer agents.

In certain embodiments, the pharmaceutical composition containing a compound of Formula (I), Formula (Ia) or Formula (Ib), or a pharmaceutically acceptable salt thereof, are immunogenic compositions.

In other embodiments, the compound(s) of Formula (I), Formula (Ia) or Formula (Ib), or a pharmaceutically acceptable salt thereof, are immune potentiators and impart an immunostimulatory effect upon administration when compared to formulations that do not contain a compound of Formula (I), Formula (Ia) or Formula (Ib), or pharmaceutically acceptable salt thereof.

The immunostimulatory effect referred to herein is often an enhancement of the immunogenic composition's effect. In certain embodiments the enhancement of the efficacy of the immunogenic composition is by at least 10% relative to the effect of the immunogenic composition in the absence of the immune potentiator. In certain embodiments the enhancement of the efficacy of the immunogenic composition is by at least 20% relative to the effect of the immunogenic composition in the absence of the immune potentiator. In certain embodiments the enhancement of the efficacy of the immunogenic composition is by at least 30% relative to the effect of the immunogenic composition in the absence of the immune potentiator. In certain embodiments the enhancement of the efficacy of the immunogenic composition is by at least 40% relative to the effect of the immunogenic composition in the absence of the immune potentiator. In certain embodiments the enhancement of the efficacy of the immunogenic composition is by at least 50% relative to the effect of the immunogenic composition in the absence of the immune potentiator. In certain embodiments the enhancement of the efficacy of the immunogenic composition is by at least 60% relative to the effect of the immunogenic composition in the absence of the immune potentiator. In certain embodiments the enhancement of the efficacy of the immunogenic composition is by at least 70% relative to the effect of the immunogenic composition in the absence of the immune potentiator. In certain embodiments the enhancement of the efficacy of the immunogenic composition is by at least 80% relative to the effect of the immunogenic composition in the absence of the immune potentiator. In certain embodiments the enhancement of the efficacy of the immunogenic composition is by at least 90% relative to the effect of the immunogenic composition in the absence of the immune potentiator. In certain embodiments the enhancement of the efficacy of the immunogenic composition is by at least 100% relative to the effect of the immunogenic composition in the absence of the immune potentiator.

The immunogenic compositions as disclosed herein may be used in a method for raising or enhancing an immune response in a mammal comprising the step of administering an effective amount of an immunogenic composition as disclosed herein. The immune response is preferably protective and preferably involves antibodies and/or cell-mediated immunity.

In certain embodiments, the immunogenic compositions disclosed herein may be used as a medicament, e.g., for use in raising or enhancing an immune response in a mammal.

In certain embodiments, the immunogenic compositions disclosed herein may be used in the manufacture of a medicament for raising an immune response in a mammal. The mammal is preferably a human, but may be, e.g., a cow, a pig, a chicken, a cat or a dog.

One way of checking efficacy of therapeutic treatment involves monitoring pathogen infection after administration of the immunogenic compositions disclosed herein. One way of checking efficacy of prophylactic treatment involves monitoring immune responses, systemically (such as monitoring the level of IgG1 and IgG2a production) and/or mucosally (such as monitoring the level of IgA production), against the antigens included in or administered in conjunction with the immunogenic compositions disclosed herein after administration of the immunogenic composition (and the antigen if administered separately). Typically, antigen-specific serum antibody responses are determined post-immunisation but pre-challenge whereas antigen-specific mucosal antibody responses are determined post-immunisation and post-challenge.

Another way of assessing the immunogenicity of the immunogenic compositions disclosed herein where the antigen is a protein is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the immunogenic compositions can also be determined in vivo by challenging appropriate animal models of the pathogen of interest infection.

The immunogenic compositions disclosed herein will generally be administered directly to a subject. Direct delivery may be accomplished by parenteral injection (e.g., subcutaneously, intraperitoneally, intravenously, intramuscularly, or to the interstitial space of a tissue), or mucosally, such as by rectal, oral (e.g., tablet, spray), vaginal, topical, transdermal or transcutaneous, intranasal, ocular, aural, pulmonary or other mucosal administration.

The immunogenic compositions may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Certain aspects and examples of the invention are provided in the following listing of enumerated embodiments. It will be recognized that features specified in each embodiment may be combined with other specified features to provide further embodiments of the present invention.

1. Compounds, and the pharmaceutically acceptable salts, individual isomers and mixture of isomers thereof, have a structure according to Formula (I):

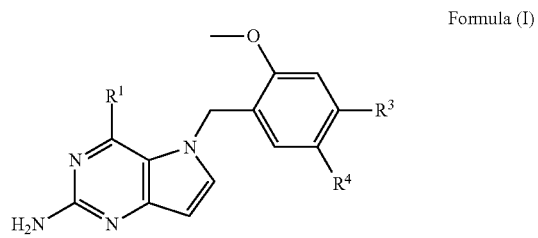

Formula (I)

$R^1$ is —$NHR^6$ or —$NHCHR^6R^9$;

$R^3$ is H, -$L_2C(=O)OR^7$, —$C(=O)OL_6R^{12}$, —$C(=O)OL_2R^{12}$, -$L_2C(=O)OL_2R^{12}$, -$L_4C(=O)OL_6OH$, -$L_4R^{12}$, -$L_2C(=O)OL_4C(=O)L_2R^{12}$, -$L_2C(=O)OL_6R^{12}$, -$L_2C(=O)OL_4C(=O)OL_2R^{12}$, -$L_2C(=O)OL_4C(=O)R^{12}$, -$L_4C(=O)OL_2C(=O)R^{12}$, —$CF_2C(=O)R^7$, —$CH=CHC(=O)OL_4C(=O)R^{12}$, —$OL_2C(=O)OL_4C(=O)R^{12}$, —$OL_4C(=O)OL_2R^{12}$, —$OL_4C(=O)OL_2C(=O)R^{12}$ or -$L_2C(=O)OL_3R^{12}$;

$R^4$ is H, -$L_2C(=O)OR^7$, —$C(=O)OL_6R^{12}$, —$C(=O)OL_2R^{12}$, -$L_2C(=O)OL_2R^{12}$, -$L_4C(=O)OL_6OH$, -$L_4R^{12}$, -$L_2C(=O)OL_4C(=O)L_2R^{12}$, -$L_2C(=O)OL_6R^{12}$, -$L_2C(=O)OL_4C(=O)OL_2R^{12}$, -$L_2C(=O)OL_4C(=O)R^{12}$, -$L_4C(=O)OL_2C(=O)R^{12}$, —$CF_2C(=O)R^7$, —$CH=CHC(=O)OL_4C(=O)R^{12}$, —$OL_2C(=O)OL_4C(=O)R^{12}$, —$OL_4C(=O)OL_2R^{12}$, —$OL_4C(=O)OL_2C(=O)R^{12}$ or -$L_2C(=O)OL_3R^{12}$;

where when $R^4$ is H, then $R^3$ is -$L_2C(=O)OR^7$, —$C(=O)OL_6R^{12}$, —$C(=O)OL_2R^{12}$, -$L_2C(=O)OL_2R^{12}$, -$L_4C(=O)OL_5OH$, -$L_4R^{12}$, -$L_2C(=O)OL_4C(=O)L_2R^{12}$, -$L_2C(=O)OL_6R^{12}$, -$L_2C(=O)OL_4C(=O)OL_2R^{12}$, -$L_2C(=O)OL_4C(=O)R^{12}$, -$L_4C(=O)OL_2C(=O)R^{12}$, —$CF_2C(=O)R^7$, —$CF_2C(=O)OR^7$, —$C(=O)OR^7$, —$N(R^{11})_2$, —$CH=CHC(=O)OL_4C(=O)R^{12}$, —$OL_2C(=O)OL_4C(=O)R^{12}$, —$OL_4C(=O)OL_2R^{12}$, —$OL_4C(=O)OL_2C(=O)R^{12}$ or -$L_2C(=O)OL_3R^{12}$;

or when $R^3$ is H, then $R^4$ is -$L_2C(=O)OR^7$, —$C(=O)OL_6R^{12}$, —$C(=O)OL_2R^{12}$, -$L_2C(=O)OL_2R^{12}$, -$L_4C(=O)OL_5OH$, -$L_4R^{12}$, -$L_2C(=O)OL_4C(=O)L_2R^{12}$, -$L_2C(=O)OL_6R^{12}$, -$L_2C(=O)OL_4C(=O)OL_2R^{12}$, -$L_2C(=O)OL_4C(=O)R^{12}$, -$L_4C(=O)OL_2C(=O)R^{12}$, —$CF_2C(=O)R^7$, —$CF_2C(=O)OR^7$, —$C(=O)OR^7$, —$N(R^{11})_2$, —$CH=CHC(=O)OL_4C(=O)R^{12}$, —$OL_2C(=O)OL_4C(=O)R^{12}$, —$OL_4C(=O)OL_2R^{12}$, —$OL_4C(=O)OL_2C(=O)R^{12}$ or -$L_2C(=O)OL_3R^{12}$;

$L_1$ is $-(CH_2)_m-$; $L_2$ is $-(CH_2)_m-$; $L_3$ is $-(CH_2)_m-$; $L_4$ is $-(CH_2)_m-$; $L_5$ is $-(CH_2)_m-$; $L_6$ is $-(CH_2)_mO(CH_2)_m-$;

$L_9$ is $-(CH_2)_m-$; $R^6$ is $-C_4$-$C_6$alkyl; $R^7$ is $-C_1$-$C_3$alkyl; $R^9$ is $L_1OH$; each $R^{11}$ is independently selected from H or $-C_1$-$C_3$alkyl;

$R^{12}$ is
  a) $-N(R^{11})_2$;
  b) an unsubstituted 5-6 membered heterocycloalkyl having 1 to 2 heteroatoms independently selected from N and O;
  c) a 5-6 membered heterocycloalkyl having 1 to 2 heteroatoms independently selected from N and O substituted with =O;
  d) a 5-6 membered heterocycloalkyl having 1 to 2 heteroatoms independently selected from N and O substituted with $C_1$-$C_3$alkyl or $-C(=O)OR^7$;
  or
  e) an unsubstituted phenyl;
and
each m is independently selected from 1, 2, 3, and 4

2. In certain embodiments, the compound of Formula (I) wherein:
$R^1$ is $-NHR^6$ or $-NHCHR^6R^9$;
$R^3$ is H, -$L_2$C(=O)OR$^7$, $-C(=O)OL_6R^{12}$, $-C(=O)OL_2R^{12}$, -$L_2$C(=O)OL$_2$R$^{12}$, -$L_4$C(=O)OL$_6$OH, -$L_4$R$^{12}$, -$L_2$C(=O)OL$_4$C(=O)L$_2$R$^{12}$, -$L_2$C(=O)OL$_6$R$^{12}$, -$L_2$C(=O)OL$_4$C(=O)OL$_2$R$^{12}$, -$L_2$C(=O)OL$_4$C(=O)R$^{12}$, -$L_4$C(=O)OL$_2$C(=O)R$^{12}$, $-CF_2C(=O)R^7$, $-CH=CHC(=O)OL_4C(=O)R^{12}$, $-OL_2C(=O)OL_4C(=O)R^{12}$, $-OL_4C(=O)OL_2R^{12}$, $-OL_4C(=O)OL_2C(=O)R^{12}$ or -$L_2$C(=O)OL$_3$R$^{12}$;

$R^4$ is H, -$L_2$C(=O)OR$^7$, $-C(=O)OL_6R^{12}$, $-C(=O)OL_2R^{12}$, -$L_2$C(=O)OL$_2$R$^{12}$, -$L_4$C(=O)OL$_5$OH, -$L_4$R$^{12}$, -$L_2$C(=O)OL$_4$C(=O)L$_2$R$^{12}$, -$L_2$C(=O)OL$_6$R$^{12}$, -$L_2$C(=O)OL$_4$C(=O)OL$_2$R$^{12}$, -$L_2$C(=O)OL$_4$C(=O)R$^{12}$, -$L_4$C(=O)OL$_2$C(=O)R$^{12}$, $-CF_2C(=O)R^7$, $-CH=CHC(=O)OL_4C(=O)R^{12}$, $-OL_2C(=O)OL_4C(=O)R^{12}$, $-OL_4C(=O)OL_2R^{12}$, $-OL_4C(=O)OL_2C(=O)R^{12}$ or -$L_2$C(=O)OL$_3$R$^{12}$;

where when $R^4$ is H, then $R^3$ is -$L_2$C(=O)OR$^7$, $-C(=O)OL_6R^{12}$, $-C(=O)OL_2R^{12}$, -$L_2$C(=O)OL$_2$R$^{12}$, -$L_4$C(=O)OL$_5$OH, -$L_4$R$^{12}$, -$L_2$C(=O)OL$_4$C(=O)L$_2$R$^{12}$, -$L_2$C(=O)OL$_6$R$^{12}$, -$L_2$C(=O)OL$_4$C(=O)OL$_2$R$^{12}$, -$L_2$C(=O)OL$_4$C(=O)R$^{12}$, -$L_4$C(=O)OL$_2$C(=O)R$^{12}$, $-CF_2C(=O)R^7$, $-CH=CHC(=O)OL_4C(=O)R^{12}$, $-OL_2C(=O)OL_4C(=O)R^{12}$, $-OL_4C(=O)OL_2R^{12}$, $-OL_4C(=O)OL_2C(=O)R^{12}$ or -$L_2$C(=O)OL$_3$R$^{12}$;

or when $R^3$ is H, then $R^4$ is -$L_2$C(=O)OR$^7$, $-C(=O)OL_6R^{12}$, $-C(=O)OL_2R^{12}$, -$L_2$C(=O)OL$_2$R$^{12}$, -$L_4$C(=O)OL$_5$OH, -$L_4$R$^{12}$, -$L_2$C(=O)OL$_4$C(=O)L$_2$R$^{12}$, -$L_2$C(=O)OL$_6$R$^{12}$, -$L_2$C(=O)OL$_4$C(=O)OL$_2$R$^{12}$, -$L_2$C(=O)OL$_4$C(=O)R$^{12}$, -$L_4$C(=O)OL$_2$C(=O)R$^{12}$, $-CF_2C(=O)R^7$, $-CH=CHC(=O)OL_4C(=O)R^{12}$, $-OL_2C(=O)OL_4C(=O)R^{12}$, $-OL_4C(=O)OL_2R^{12}$, $-OL_4C(=O)OL_2C(=O)R^{12}$ or -$L_2$C(=O)OL$_3$R$^{12}$;

$L_1$ is $-(CH_2)_m-$; $L_2$ is $-(CH_2)_m-$; $L_3$ is $-(CH_2)_m-$; $L_4$ is $-(CH_2)_m-$; $L_5$ is $-(CH_2)_m-$; $L_6$ is $-(CH_2)_mO(CH_2)_m-$;

$L_9$ is $-(CH_2)_m-$; $R^6$ is $-C_4$-$C_6$alkyl; $R^7$ is $-C_1$-$C_3$alkyl; $R^9$ is $L_1OH$; each $R^{11}$ is independently selected from H or $-C_1$-$C_3$alkyl;

$R^{12}$ is
  a) $-N(R^{11})_2$;
  b) an unsubstituted 5-6 membered heterocycloalkyl having 1 to 2 heteroatoms independently selected from N and O;
  c) a 5-6 membered heterocycloalkyl having 1 to 2 heteroatoms independently selected from N and O substituted with =O;
  d) a 5-6 membered heterocycloalkyl having 1 to 2 heteroatoms independently selected from N and O substituted with $C_1$-$C_3$alkyl or $-C(=O)OR^7$;
  or
  e) an unsubstituted phenyl;
and each m is independently selected from 1, 2, 3, and 4.

3. In certain embodiments, the compound of Formula (I) is a compound of Formula (Ia) or Formula (Ib):

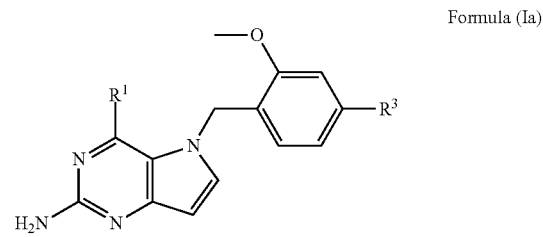

Formula (Ia)

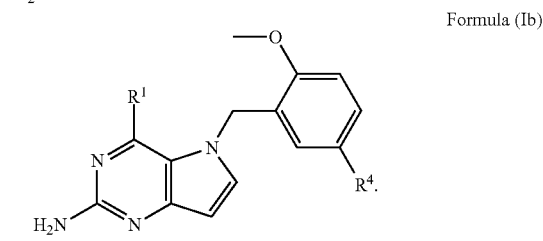

Formula (Ib)

4. In certain embodiments of the compounds of Formula (I), Formula (Ia) or Formula (Ib),
$R^1$ is $-NHR^6$ or $-NHCHR^6R^9$;
$R^3$ is H, -$L_2$C(=O)OR$^7$, $-C(=O)OL_6R^{12}$, $-C(=O)OL_2R^{12}$, -$L_2$C(=O)OL$_2$R$^{12}$, -$L_4$C(=O)OL$_6$OH, -$L_4$R$^{12}$, -$L_2$C(=O)OL$_4$C(=O)L$_2$R$^{12}$, -$L_2$C(=O)OL$_6$R$^{12}$, -$L_2$C(=O)OL$_4$C(=O)OL$_2$R$^{12}$, -$L_2$C(=O)OL$_4$C(=O)R$^{12}$, -$L_4$C(=O)OL$_2$C(=O)R$^{12}$ or -$L_2$C(=O)OL$_3$R$^{12}$;

$R^4$ is H, $-CF_2C(=O)R^7$, -$L_4$R$^{12}$, $-CH=CHC(=O)OL_4C(=O)R^{12}$, $-OL_2C(=O)OL_4C(=O)R^{12}$, $-OL_4C(=O)OL_2R^{12}$, -$L_2$C(=O)OR$^7$, -$L_2$C(=O)OL$_4$C(=O)R$^{12}$, $-OL_4C(=O)OL_2C(=O)R^{12}$ or -$L_2$C(=O)OL$_3$R$^{12}$;

where when $R^4$ is H, then $R^3$ is -$L_2$C(=O)OR$^7$, $-C(=O)OL_6R^{12}$, $-C(=O)OL_2R^{12}$, -$L_2$C(=O)OL$_2$R$^{12}$, -$L_4$C(=O)OL$_6$OH, -$L_4$R$^{12}$, -$L_2$C(=O)OL$_4$C(=O)L$_2$R$^{12}$, -$L_2$C(=O)OL$_6$R$^{12}$, -$L_2$C(=O)OL$_4$C(=O)OL$_2$R$^{12}$, -$L_2$C(=O)OL$_4$C(=O)R$^{12}$, -$L_4$C(=O)OL$_2$C(=O)R$^{12}$ or -$L_2$C(=O)OL$_3$R$^{12}$;

or when $R^3$ is H, then $R^4$ is $-CF_2C(=O)R^7$, -$L_4$R$^{12}$, $-CH=CHC(=O)OL_4C(=O)R^{12}$, $-OL_2C(=O)OL_4C(=O)R^{12}$, $-OL_4C(=O)OL_2R^{12}$, -$L_2$C(=O)OR$^7$, -$L_2$C(=O)OL$_4$C(=O)R$^{12}$, $-OL_4C(=O)OL_2C(=O)R^{12}$ or -$L_2$C(=O)OL$_3$R$^{12}$;

$L_1$ is $-CH_2-$; $L_2$ is $-CH_2-$ or $-CH_2CH_2-$; $L_3$ is $-CH_2CH_2-$ or $-CH_2CH_2CH_2CH_2-$; $L_4$ is $-CH_2-$, $L_5$ is $-CH_2CH_2-$, $L_6$ is $-(CH_2)_2O(CH_2)_2-$; $L_9$ is $-CH_2CH_2CH_2CH_2-$; $R^6$ is $-C_4$alkyl or $-C_8$alkyl; $R^7$ is methyl, ethyl or propyl; $R^9$ is $L_1OH$; each $R^{11}$ is independently selected from $-C_1$-$C_3$alkyl;

$R^{12}$ is
  a) $-N(R^{11})_2$;
  b) an unsubstituted piperazinyl or an unsubstituted morpholinyl;

c) a 5-6 membered heterocycloalkyl having 1 to 2 heteroatoms independently selected from N and O substituted with =O;
d) a piperazinyl substituted with $C_1$-$C_3$alkyl or —C(=O)OR$^7$;
or
e) an unsubstituted phenyl;
and each m is independently selected from 1, 2, 3, and 4.

5. In certain embodiments of the compounds of Formula (Ia) or Formula (Ib),
$R^1$ is —NHR$^6$ or —NHCHR$^6$R$^9$;
$R^3$ is -L$_2$C(=O)OR$^7$, —C(=O)OL$_6$R$^{12}$, —C(=O)OL$_2$R$^{12}$, -L$_2$C(=O)OL$_2$R$^{12}$, -L$_4$C(=O)OL$_6$OH, -L$_4$R$^{12}$, -L$_2$C(=O)OL$_4$C(=O)L$_2$R$^{12}$, -L$_2$C(=O)OL$_6$R$^{12}$, -L$_2$C(=O)OL$_4$C(=O)OL$_2$R$^{12}$, -L$_2$C(=O)OL$_4$C(=O)R$^{12}$, -L$_4$C(=O)OL$_2$C(=O)R$^{12}$, —CF$_2$C(=O)OR$^7$, —C(=O)OR$^7$, —N(R$^{11}$)$_2$ or -L$_2$C(=O)OL$_3$R$^{12}$;
$R^4$ is —CF$_2$C(=O)R$^7$, -L$_4$R$^{12}$, —CH=CHC(=O)OL$_4$C(=O)R$^{12}$, —OL$_2$C(=O)OL$_4$C(=O)R$^{12}$, —OL$_4$C(=O)OL$_2$R$^{12}$, -L$_2$C(=O)OR$^7$, -L$_2$C(=O)OL$_4$C(=O)R$^{12}$, —OL$_4$C(=O)OL$_2$C(=O)R$^{12}$, —CF$_2$C(=O)OR$^7$, —C(=O)OR$^7$, —N(R$^{11}$)$_2$ or -L$_2$C(=O)OL$_3$R$^{12}$;
$L_1$ is —CH$_2$—; $L_2$ is —CH$_2$— or —CH$_2$CH$_2$—; $L_3$ is —CH$_2$CH$_2$— or —CH$_2$CH$_2$CH$_2$CH$_2$—; $L_4$ is —CH$_2$—, $L_5$ is —CH$_2$CH$_2$—, $L_6$ is —(CH$_2$)$_2$O(CH$_2$)$_2$—; $L_9$ is —CH$_2$CH$_2$CH$_2$CH$_2$—; $R^6$ is —C$_4$alkyl or —C$_8$alkyl; $R^7$ is methyl, ethyl or propyl; $R^9$ is L$_1$OH; each R$^{11}$ is independently selected from —C$_1$-C$_3$alkyl;
$R^{12}$ is
a) —N(R$^{11}$)$_2$;
b) an unsubstituted piperazinyl or an unsubstituted morpholinyl;
c) a 5-6 membered heterocycloalkyl having 1 to 2 heteroatoms independently selected from N and O substituted with =O;
d) a piperazinyl substituted with $C_1$-$C_3$alkyl or —C(=O)OR$^7$;
or
e) an unsubstituted phenyl;
and
each m is independently selected from 1, 2, 3, and 4.

6. In certain embodiments of the compounds of Formula (Ia) or Formula (Ib),
$R^1$ is —NHR$^6$ or —NHCHR$^6$R$^9$;
$R^3$ is -L$_2$C(=O)OR$^7$, —C(=O)OL$_6$R$^{12}$, —C(=O)OL$_2$R$^{12}$, -L$_4$C(=O)OL$_5$OH, -L$_4$R$^{12}$, -L$_2$C(=O)OL$_4$C(=O)L$_2$R$^{12}$, -L$_2$C(=O)OL$_6$R$^{12}$, -L$_2$C(=O)OL$_4$C(=O)OL$_2$R$^{12}$, -L$_2$C(=O)OL$_4$C(=O)R$^{12}$, -L$_4$C(=O)OL$_2$C(=O)R$^{12}$ or -L$_2$C(=O)OL$_3$R$^{12}$;
$R^4$ is —CF$_2$C(=O)R$^7$, -L$_4$R$^{12}$, —CH=CHC(=O)OL$_4$C(=O)R$^{12}$, —OL$_2$C(=O)OL$_4$C(=O)R$^{12}$, —OL$_4$C(=O)OL$_2$R$^{12}$, -L$_2$C(=O)OR$^7$, -L$_2$C(=O)OL$_4$C(=O)R$^{12}$, —OL$_4$C(=O)OL$_2$C(=O)R$^{12}$ or -L$_2$C(=O)OL$_3$R$^{12}$;
$L_1$ is —CH$_2$—; $L_2$ is —CH$_2$— or —CH$_2$CH$_2$—; $L_3$ is —CH$_2$CH$_2$— or —CH$_2$CH$_2$CH$_2$CH$_2$—; $L_4$ is —CH$_2$—, $L_5$ is —CH$_2$CH$_2$—, $L_6$ is —(CH$_2$)$_2$O(CH$_2$)$_2$—; $L_9$ is —CH$_2$CH$_2$CH$_2$CH$_2$—; $R^6$ is —C$_4$alkyl or —C$_8$alkyl; $R^7$ is methyl, ethyl or propyl; $R^9$ is L$_1$OH; each R$^{11}$ is independently selected from —C$_1$-C$_3$alkyl;

$R^{12}$ is
a) —N(R$^{11}$)$_2$;
b) an unsubstituted piperazinyl or an unsubstituted morpholinyl;
c) a 5-6 membered heterocycloalkyl having 1 to 2 heteroatoms independently selected from N and O substituted with =O;
d) a piperazinyl substituted with $C_1$-$C_3$alkyl or —C(=O)OR$^7$;
or
e) an unsubstituted phenyl;
and each m is independently selected from 1, 2, 3, and 4.

7. In certain embodiments of the compounds of Formula (I), Formula (Ia) and Formula (Ib),
$R^1$ is —NHR$^6$;
$R^3$ is -L$_2$C(=O)OL$_4$C(=O)R$^{12}$ and $R^4$ is H;
or $R^3$ is H and $R^4$ is -L$_2$C(=O)OL$_4$C(=O)R$^{12}$;
$R^6$ is —C$_4$-C$_6$alkyl;
$L_2$ is —(CH$_2$)$_m$—;
$L_4$ is —(CH$_2$)$_m$—;
$R^{12}$ is an unsubstituted 5-6 membered heterocycloalkyl having 1 to 2 heteroatoms independently selected from N and O;
and
each m is independently selected from 1, 2, 3, and 4

8. In certain embodiments of the compounds of Formula (I), Formula (Ia) and Formula (Ib),
$R^1$ is —NHR$^6$;
$R^3$ is -L$_2$C(=O)OL$_{4C}$(=O)L$_2$R$^{12}$ and $R^4$ is H;
or $R^3$ is H and $R^4$ is -L$_2$C(=O)OL$_4$C(=O)L$_2$R$^{12}$;
$R^6$ is —C$_4$-C$_6$alkyl; $L_2$ is —(CH$_2$)$_m$—; $L_4$ is —(CH$_2$)$_m$—;
$R^{12}$ is an unsubstituted 5-6 membered heterocycloalkyl having 1 to 2 heteroatoms independently selected from N and O;
and each m is independently selected from 1, 2, 3, and 4.

9. In certain embodiments of the compounds of Formula (I), Formula (Ia) and Formula (Ib),
$R^1$ is —NHR$^6$;
$R^3$ is -L$_2$C(=O)OL$_4$C(=O)R$^{12}$ and $R^4$ is H;
or $R^3$ is H and $R^4$ is -L$_2$C(=O)OL$_4$C(=O)R$^{12}$;
$R^6$ is —C$_8$alkyl;
$L_2$ is —CH$_2$— or —CH$_2$CH$_2$—;
$L_4$ is —CH$_2$—,
and
$R^{12}$ is an unsubstituted piperazinyl or an unsubstituted morpholinyl;

10. In certain embodiments of the compounds of Formula (I), Formula (Ia) and Formula (Ib),
$R^1$ is —NHR$^6$;
$R^3$ is -L$_2$C(=O)OL$_4$C(=O)L$_2$R$^{12}$ and $R^4$ is H;
or $R^3$ is H and $R^4$ is -L$_2$C(=O)OL$_4$C(=O)L$_2$R$^{12}$;
$R^6$ is —C$_8$alkyl; $L_2$ is —CH$_2$— or —CH$_2$CH$_2$—; $L_4$ is —CH$_2$—,
and $R^{12}$ is an unsubstituted piperazinyl or an unsubstituted morpholinyl.

11. In certain embodiments of the compounds of Formula (I), Formula (Ia) and Formula (Ib),
$R^1$ is —NHR$^6$ or —NHCHR$^6$R$^9$;
$R^3$ is H and $R^4$ is -L$_4$R$^{12}$;
or $R^3$ is -L$_4$R$^{12}$ and $R^4$ is H;
$L_1$ is —(CH$_2$)$_m$—; $L_4$ is —(CH$_2$)$_m$—; $R^6$ is —C$_4$-C$_6$alkyl; $R^9$ is L$_1$OH;
$R^{12}$ is an unsubstituted 5-6 membered heterocycloalkyl having 1 to 2 heteroatoms independently selected from N and O;
and each m is independently selected from 1, 2, 3, and 4.

12. In certain embodiments of the compounds of Formula (I), Formula (Ia) and Formula (Ib),
$R^1$ is —$NHR^6$ or —$NHCHR^6R^9$;
$R^3$ is H and $R^4$ is -$L_4R^{12}$;
or $R^3$ is -$L_4R^{12}$ and $R^4$ is H;
$L_1$ is —$(CH_2)$—; $L_4$ is —$(CH_2)$—; $R^6$ is —$C_4$alkyl or —$C_8$alkyl; $R^9$ is $L_1$OH,
and $R^{12}$ is an unsubstituted piperazinyl.

13. In certain embodiments of the compounds of Formula (I), Formula (Ia) and Formula (Ib) the compound is selected from:
2-(dimethylamino)ethyl 4-((2-amino-4-(pentylamino)-5H-pyrrolo[3,2-d]pyrimidin-5-yl)methyl)-3-methoxybenzoate; 2-(2-(dimethylamino)ethoxy)ethyl 4-((2-amino-4-(pentylamino)-5H-pyrrolo[3,2-d]pyrimidin-5-yl)methyl)-3-methoxybenzoate; methyl 2-(3-((2-amino-4-(pentylamino)-5H-pyrrolo[3,2-d]pyrimidin-5-yl)methyl)-4-methoxyphenyl)acetate; ethyl 3-(3-((2-amino-4-(pentylamino)-5H-pyrrolo[3,2-d]pyrimidin-5-yl)methyl)-4-methoxyphenyl)propanoate; methyl 2-(3-((2-amino-4-(pentylamino)-5H-pyrrolo[3,2-d]pyrimidin-5-yl)methyl)-4-methoxyphenyl)-2,2-difluoroacetate; 2-morpholino-2-oxoethyl 2-(3-((2-amino-4-(pentylamino)-5H-pyrrolo[3,2-d]pyrimidin-5-yl)methyl)-4-methoxyphenoxy)acetate; 2-morpholino-2-oxoethyl 2-(3-((2-amino-4-(pentylamino)-5H-pyrrolo[3,2-d]pyrimidin-5-yl)methyl)-4-methoxyphenyl)acetate; 2-morpholino-2-oxoethyl 2-(4-((2-amino-4-(pentylamino)-5H-pyrrolo[3,2-d]pyrimidin-5-yl)methyl)-3-methoxyphenyl)acetate; 2-(morpholin-4-yl)-2-oxoethyl 3-(4-{[2-amino-4-(pentylamino)-5H-pyrrolo[3,2-d]pyrimidin-5-yl]methyl}-3-methoxyphenyl)propanoate; (S)-2-morpholino-2-oxoethyl 3-(3-((2-amino-4-((1-hydroxyhexan-2-yl)amino)-5H-pyrrolo[3,2-d]pyrimidin-5-yl)methyl)-4-methoxyphenyl)propanoate; (S)-2-morpholino-2-oxoethyl 2-(4-((2-amino-4-((1-hydroxyhexan-2-yl)amino)-5H-pyrrolo[3,2-d]pyrimidin-5-yl)methyl)-3-methoxyphenyl)acetate; (S)-2-morpholino-2-oxoethyl 2-(3-((2-amino-4-((1-hydroxyhexan-2-yl)amino)-5H-pyrrolo[3,2-d]pyrimidin-5-yl)methyl)-4-methoxyphenyl)acetate; (S)-2-morpholino-2-oxoethyl 3-(4-((2-amino-4-((1-hydroxyhexan-2-yl)amino)-5H-pyrrolo[3,2-d]pyrimidin-5-yl)methyl)-3-methoxyphenyl) propanoate; 2-(morpholin-4-yl)-2-oxoethyl (2E)-3-(3-{[2-amino-4-(pentylamino)-5H-pyrrolo[3,2-d]pyrimidin-5-yl]methyl}-4-methoxyphenyl) prop-2-enoate; 2-(morpholin-4-yl)-2-oxoethyl 3-(3-{[2-amino-4-(pentylamino)-5H-pyrrolo[3,2-d]pyrimidin-5-yl]methyl}-4-methoxyphenyl) propanoate; 2-(benzyloxy)-2-oxoethyl 2-(4-{[2-amino-4-(pentylamino)-5H-pyrrolo[3,2-d]pyrimidin-5-yl]methyl}-3-methoxyphenyl)acetate; 2-(dipropylcarbamoyl)methyl 2-(4-{[2-amino-4-(pentylamino)-5H-pyrrolo[3,2-d]pyrimidin-5-yl]methyl}-3-methoxyphenyl)acetate; 2-(dimethylamino)-2-oxoethyl 2-(4-((2-amino-4-(pentylamino)-5H-pyrrolo[3,2-d]pyrimidin-5-yl)methyl)-3-methoxyphenyl)acetate; 2-(4-methylpiperazin-1-yl)ethyl 2-(4-{[2-amino-4-(pentylamino)-5H-pyrrolo[3,2-d]pyrimidin-5-yl]methyl}-3-methoxyphenyl)acetate; 2-hydroxyethyl 2-(4-{[2-amino-4-(pentylamino)-5H-pyrrolo[3,2-d]pyrimidin-5-yl]methyl}-3-methoxyphenyl)acetate; 4-(dimethylamino)butyl 2-(4-{[2-amino-4-(pentylamino)-5H-pyrrolo[3,2-d]pyrimidin-5-yl]methyl}-3-methoxyphenyl)acetate; 2-(morpholin-4-yl)ethyl 2-(4-{[2-amino-4-(pentylamino)-5H-pyrrolo[3,2-d]pyrimidin-5-yl]methyl}-3-methoxyphenyl)acetate; 2-(piperazin-1-yl)ethyl 2-(4-{[2-amino-4-(pentylamino)-5H-pyrrolo[3,2-d]pyrimidin-5-yl]methyl}-3-methoxyphenyl)acetate; 2-(dimethylamino)ethyl 2-(3-{[2-amino-4-(pentylamino)-5H-pyrrolo[3,2-d]pyrimidin-5-yl]methyl}-4-methoxyphenoxy)acetate; 2-(piperazin-1-yl)ethyl 2-(3-{[2-amino-4-(pentylamino)-5H-pyrrolo[3,2-d]pyrimidin-5-yl]methyl}-4-methoxyphenoxy)acetate; 2-(morpholin-4-yl)ethyl 2-(3-{[2-amino-4-(pentylamino)-5H-pyrrolo[3,2-d]pyrimidin-5-yl]methyl}-4-methoxyphenoxy)acetate; 2-(4-methylpiperazin-1-yl)ethyl 2-(3-{[2-amino-4-(pentylamino)-5H-pyrrolo[3,2-d]pyrimidin-5-yl]methyl}-4-methoxyphenoxy)acetate; (S)-2-((2-amino-5-(2-methoxy-4-(piperazin-1-ylmethyl)benzyl)-5H-pyrrolo[3,2-d]pyrimidin-4-yl)amino)hexan-1-ol; 5-(2-methoxy-4-(piperazin-1-ylmethyl)benzyl)-N4-pentyl-5H-pyrrolo[3,2-d]pyrimidine-2,4-diamine; 5-(2-methoxy-5-(piperazin-1-ylmethyl)benzyl)-N4-pentyl-5H-pyrrolo[3,2-d]pyrimidine-2,4-diamine, (S)-2-((2-amino-5-(2-methoxy-5-(piperazin-1-ylmethyl)benzyl)-5H-pyrrolo[3,2-d]pyrimidin-4-yl)amino)hexan-1-ol, and 5-(5-amino-2-methoxybenzyl)-N4-pentyl-5H-pyrrolo[3,2-d]pyrimidine-2,4-diamine.

14. In certain embodiments of the compounds of Formula (I), Formula (Ia) and Formula (Ib) the compound is selected from:
2-morpholino-2-oxoethyl 2-(3-((2-amino-4-(pentylamino)-5H-pyrrolo[3,2-d]pyrimidin-5-yl)methyl)-4-methoxyphenoxy)acetate; 2-morpholino-2-oxoethyl 2-(3-((2-amino-4-(pentylamino)-5H-pyrrolo[3,2-d]pyrimidin-5-yl)methyl)-4-methoxyphenyl)acetate; 2-morpholino-2-oxoethyl 2-(4-((2-amino-4-(pentylamino)-5H-pyrrolo[3,2-d]pyrimidin-5-yl)methyl)-3-methoxyphenyl)acetate, and 2-(morpholin-4-yl)-2-oxoethyl 3-(4-{[2-amino-4-(pentylamino)-5H-pyrrolo[3,2-d]pyrimidin-5-yl]methyl}-3-methoxyphenyl)propanoate.

15. In certain embodiments of the compounds of Formula (I), Formula (Ia) and Formula (Ib) the compound is selected from:
(S)-2-((2-amino-5-(2-methoxy-4-(piperazin-1-ylmethyl)benzyl)-5H-pyrrolo[3,2-d]pyrimidin-4-yl)amino)hexan-1-ol; 5-(2-methoxy-4-(piperazin-1-ylmethyl)benzyl)-N4-pentyl-5H-pyrrolo[3,2-d]pyrimidine-2,4-diamine; 5-(2-methoxy-5-(piperazin-1-ylmethyl)benzyl)-N4-pentyl-5H-pyrrolo[3,2-d]pyrimidine-2,4-diamine, (S)-2-((2-amino-5-(2-methoxy-5-(piperazin-1-ylmethyl)benzyl)-5H-pyrrolo[3,2-d]pyrimidin-4-yl)amino) hexan-1-ol, and 5-(5-amino-2-methoxybenzyl)-N4-pentyl-5H-pyrrolo[3,2-d]pyrimidine-2,4-diamine.

16. Another embodiment are methods of using compounds of Formula (I), Formula (Ia) and Formula (Ib), and pharmaceutical compositions comprising such compounds of Formula (I), Formula (Ia) and Formula (Ib).

17. Another embodiment are pharmaceutical compositions that include a therapeutically effective amount of a compound of Formula (I), Formula (Ia) or Formula (Ib), and a pharmaceutically acceptable carrier. In certain embodiments of such pharmaceutical compositions, the pharmaceutical composition is formulated for intravenous administration, intravitrial administration, intramuscular administration, oral administration, rectal administration inhalation, nasal administration, topical administration, ophthalmic administration or otic administration. In other embodiments, the pharmaceutical compositions are in the form of a tablet, a pill, a capsule, a liquid, an inhalant, a nasal spray solution, a suppository, a solution, an emulsion, an ointment, eye drop or ear drop. In other embodiments, such pharmaceutical compositions further include one or more additional therapeutic agents.

18. Another embodiment are medicaments for treating a patient with a disease or disorder associated with TLR7 receptor activity, and such medicaments include a therapeutically effective amount of a compound of Formula (I), Formula (Ia) or Formula (Ib).

19. Another embodiment is the use of a compound of Formula (I), Formula (Ia) or Formula (Ib) in the manufacture of a medicament for treating a disease or disorder associated with TLR7 activity.

20. In certain embodiments of the use of a compound of Formula (I), Formula (Ia) or Formula (Ib) in the manufacture of a medicament the disease is an infectious disease, a viral infectious disease, an inflammatory disease, a respiratory disease, a dermatological disease, an autoimmune disease, a cell-proliferative disease or cancer.

21. In certain embodiments of such the use of a compound of Formula (I), Formula (Ia) or Formula (Ib) in the manufacture of a medicament the disease is asthma, chronic obstructive pulmonary disease (COPD), adult respiratory distress syndrome (ARDS), ulcerative colitis, Crohn's disease, bronchitis, dermatitis, actinic keratosis, basal cell carcinoma, bladder cancer, allergic rhinitis, psoriasis, scleroderma, urticaria, rheumatoid arthritis, multiple sclerosis, cancer, breast cancer, HIV, hepatitis, hepatitis C or lupus.

22. In certain embodiments of such the use of a compound of Formula (I), Formula (Ia) or Formula (Ib) in the manufacture of a medicament the disease is hepatitis B, hepatitis C, colorectal cancer or hepatocellular carcinoma.

23. Another embodiment is methods for activating a TLR7 receptor, wherein the method includes administering to a system or a subject in need thereof, a therapeutically effective amount of a compound of Formula (I), Formula (Ia) or Formula (Ib), or pharmaceutically acceptable salts or pharmaceutical compositions thereof, thereby activating the TLR receptor.

24. In certain embodiments of such methods for activating a TLR7 receptor, the methods include administering the compound to a cell or tissue system or to a human or animal subject.

25. Another embodiment is methods for treating a disease or disorder associated with TLR7 activity, wherein the method includes administering to a system or subject in need of such treatment an effective amount of a compound of Formula (I), Formula (Ia) or Formula (Ib), or pharmaceutically acceptable salts thereof, thereby treating the disease or disorder.

26. In certain embodiments of such methods for treating a disease or disorder associated with TLR7 activity, the methods include administering the compound to a cell or tissue system or to a human or animal subject.

27. In certain embodiments of such methods for treating a disease or disorder associated with TLR7 activity, the disease or condition is an infectious disease, a viral infectious disease, an inflammatory disease, a respiratory disease, a dermatological disease, an autoimmune disease, a cell-proliferative disease or cancer.

28. In certain embodiments of such methods for treating a disease or disorder associated with TLR7 activity, the disease or condition is asthma, chronic obstructive pulmonary disease (COPD), adult respiratory distress syndrome (ARDS), ulcerative colitis, Crohn's disease, bronchitis, dermatitis, actinic keratosis, basal cell carcinoma, bladder cancer, allergic rhinitis, psoriasis, scleroderma, urticaria, rheumatoid arthritis, multiple sclerosis, cancer, breast cancer, HIV, hepatitis, hepatitis C or lupus.

29. In certain embodiments of such methods for treating a disease or disorder associated with TLR7 activity, the disease or condition is hepatitis B, hepatitis C, colorectal cancer or hepatocellular carcinoma.

30. Another embodiment is methods for treating a cell-proliferative disease, comprising administering to a system or subject in need of such treatment an effective amount of a compound of Formula (I), Formula (Ia) or Formula (Ib), or pharmaceutically acceptable salts thereof; wherein the cell-proliferative disease is bladder cancer, lymphoma, osteosarcoma, melanoma, or a tumor of breast, renal, prostate, colorectal, thyroid, ovarian, pancreatic, neuronal, lung, uterine or gastrointestinal tumor.

31. In certain embodiments of such methods for treating a cell-proliferative disease, the cell-proliferative disease is, colorectal cancer or hepatocellular carcinoma.

32. Another embodiment is compounds for use in a method of medical treatment, wherein the method of medical treatment is for treating a disease associated with TLR7 receptor activity, wherein the disease is selected from an infectious disease, a viral infectious disease, an inflammatory disease, a respiratory disease, a dermatological disease, an autoimmune disease, a cell-proliferative disease or cancer, and wherein the compound is a compound of Formula (I), Formula (Ia) or Formula (Ib).

33. In certain embodiments of such use in a method of medical treatment, the disease or condition is asthma, chronic obstructive pulmonary disease (COPD), adult respiratory distress syndrome (ARDS), ulcerative colitis, Crohn's disease, bronchitis, dermatitis, actinic keratosis, basal cell carcinoma, bladder cancer, allergic rhinitis, psoriasis, scleroderma, urticaria, rheumatoid arthritis, multiple sclerosis, cancer, breast cancer, HIV, hepatitis, hepatitis C or lupus.

34. In certain embodiments of such use in a method of medical treatment, the disease is hepatitis B, hepatitis C, colorectal cancer or hepatocellular carcinoma.

EXAMPLES

The following examples illustrate the preparation of certain exemplary compounds of Formula (I). Table 1 gives the Human TLR7 $EC_{50}$ (nM) values obtained using these exemplary compounds.

Synthesis of Exemplary Compounds

Example 1

Synthesis of methyl 4-((2-amino-4-(pentylamino)-5H-pyrrolo[3,2-d]pyrimidin-5-yl)methyl)-3-methoxybenzoate

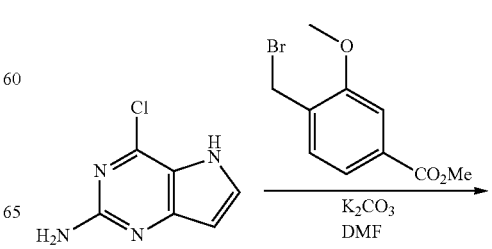

43

-continued

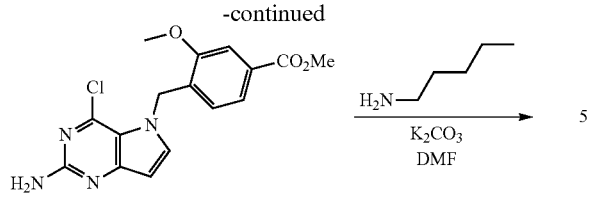

Step 1: Preparation of methyl 4-(bromomethyl)-3-methoxybenzoate

Methyl 3-methoxy-4-methylbenzoate (commercially available, 1.0 equiv.) was dissolved in chloroform (0.1 M), and was treated with N-bromosuccinimide (1.1 equiv.) and azobisisobutyronitrile (AIBN, catalytic amount). The reaction mixture was stirred at reflux overnight. After cooling down to room temperature, the reaction mixture was purified by ISCO (silica gel column, EtOAc/hexanes) to afford methyl 4-(bromomethyl)-3-methoxybenzoate as a white solid.

Step 2: Preparation of methyl 4-((2-amino-4-(pentylamino)-5H-pyrrolo[3,2-d]pyrimidin-5-yl)methyl)-3-methoxybenzoate 4-Chloro-5H-pyrrolo[3,2-d]pyrimidin-2-amine (commercially available, 1 equiv.) was dissolved in NMP (0.1 M) and stirred at room temperature under $N_2$. Potassium carbonate (1 equiv.) was added, followed by addition of methyl 4-(bromomethyl)-3-methoxybenzoate (from the previous step, 1 equiv.) to give a suspension. The reaction was stirred at room temperature for 18 hours and LCMS shows complete conversion into methyl 4-((2-amino-4-chloro-5-pyrrolo[3,2-d]pyrimidin-5-yl)methyl)-3-methoxybenzoate. N-pentyl amine (2 equiv.) was added, followed by potassium carbonate (1 equiv.). The reaction mixture was stirred at 60° C. overnight. After cooling down to room temperature, the reaction mixture was concentrated en vacuuo, and was purified by ISCO chromatography (0-100% EtOAc in hexanes) to afford the title product as a white solid. $^1$H NMR (DMSO-d6): δ 7.53 (d, 1H), 7.51 (d, 1H), 7.48 (dd, 1H), 7.40 (br s, 2H), 7.34 (t, 1H), 6.45 (d, 1H), 6.27 (d, 1H), 5.67 (s, 2H), 3.92 (s, 3H), 3.83 (s, 3H), 3.40 (q, 2H), 1.41-1.32 (m, 2H), 1.17-1.07 (m, 2H), 0.97-0.87 (m, 2H), 0.73 (t, 3H). LRMS [M+H]=398.2.

44

Example 2

2-(dimethylamino)ethyl 4-((2-amino-4-(pentylamino)-5H-pyrrolo[3,2-d]pyrimidin-5-yl)methyl)-3-methoxybenzoate

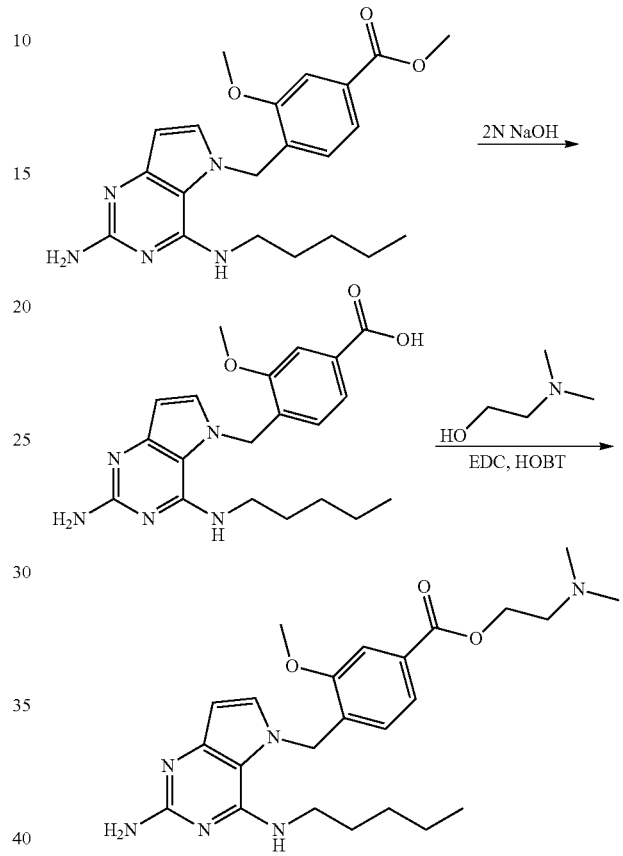

Step 1: Preparation of 4-((2-amino-4-(pentylamino)-5H-pyrrolo[3,2-d]pyrimidin-5-yl)methyl)-3-methoxybenzoic acid Methyl 4-((2-amino-4-(pentylamino)-5H-pyrrolo[3,2-d]pyrimidin-5-yl)methyl)-3-methoxybenzoate (1 equiv., Example 1) was suspended in THF-methanol (5:1, 1 M), and was treated with 2N NaOH (10 equiv.). Reaction was heated at 65° C. for 1 hour. After cooling down to room temperature, the reaction mixture was purified by reverse phase HPLC and lyophilized down to afford title compound as a white powder. 1H NMR (CDCl3-CD3OD): δ 7.68 (s, 1H), 7.57 (d, 1H), 7.42 (d, 1H), 6.65 (d, 1H), 6.26 (d, 1H), 5.62 (s, 2H), 3.98 (s, 3H), 3.53 (t, 2H), 1.46-1.42 (m, 2H), 1.24-1.20 (m, 2H), 1.05-1.00 (m, 2H), 0.82 (t, 3H). LRMS [M+H]=384.2.

Step 2: Preparation of 2-(dimethylamino)ethyl 4-((2-amino-4-(pentylamino)-5H-pyrrolo[3,2-d]pyrimidin-5-yl)methyl)-3-methoxybenzoate 4-((2-Amino-4-(pentylamino)-5H-pyrrolo[3,2-d]pyrimidin-5-yl)methyl)-3-methoxybenzoic acid (from the previous step, 1 equiv.) was dissolved in DMF (0.2 M), and was treated with 3-(ethyliminomethyleneamino)-N,N-dimethyl-propan-1-amine (EDC, 2 equiv.) and 1-hydroxybenzotriazole (HOBT, 2 equiv.). After 5 minutes, 2-(dimethylamino) ethyl alcohol (5 equiv.) was added, and the reaction mixture was heated at 50° C. for 2 hours. After cooling down to room temperature, the content was poured into equal volume of saturated sodium bicarbonate aqueous solution, and was extracted with 30% isopropanol in chloroform. The organic layers were combined and dried over anhydrous sodium sulfate, and concentrated in vacuuo. The crude was purified by reverse phase prep-HPLC to afford title compound as a white solid. 1H NMR (CD3OD): δ 7.71 (s, 1H), 7.65 (d, 1H), 7.41 (d, 1H), 6.67 (d, 1H), 6.27 (d, 1H), 5.64 (s, 2H), 4.67 (t, 2H), 4.00 (s, 3H), 3.60 (t, 2H), 3.52 (t, 2H), 2.99 (s, 6H), 1.49-1.45 (m, 2H), 1.26-1.22 (m, 2H), 1.10-1.06 (m, 2H), 0.84 (t, 3H). LRMS [M+H]=455.3.

Example 3

2-(2-(dimethylamino)ethoxy)ethyl 4-((2-amino-4-(pentylamino)-5H-pyrrolo[3,2-d]pyrimidin-5-yl) methyl)-3-methoxybenzoate

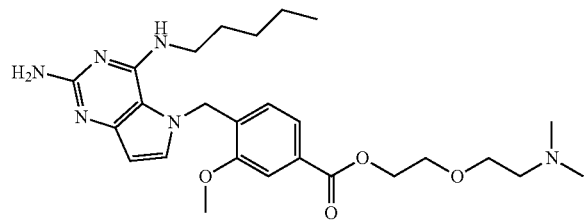 [SMILES: CCCCCNc1nc(N)nc2ccn(Cc3ccc(C(=O)OCCOCCN(C)C)cc3OC)c12]

Preparation of 2-(2-(dimethylamino)ethoxy)ethyl 4-((2-amino-4-(pentylamino)-5H-pyrrolo[3,2-d]pyrimidin-5-yl)methyl)-3-methoxybenzoate 2-(2-(Dimethylamino)ethoxy)ethyl 4-((2-amino-4-(pentylamino)-5H-pyrrolo[3,2-d]pyrimidin-5-yl)methyl)-3-methoxybenzoate was prepared from 4-((2-amino-4-(pentylamino)-5H-pyrrolo[3,2-d]pyrimidin-5-yl)methyl)-3-methoxybenzoic acid (Example 2, Step 1) and 2-(2-(dimethylamino)ethoxy)ethanol following the same protocol as Example 2, Step 2. 1H NMR (CD3OD): δ7.67 (s, 1H), 7.58 (d, 1H), 7.41 (d, 1H), 6.67 (d, 1H), 6.27 (d, 1H), 5.63 (s, 2H), 4.51 (t, 2H), 4.00 (s, 3H), 3.90-3.84 (m, 4H), 3.62 (t, 2H), 3.52 (t, 2H), 2.89 (s, 6H), 1.48-1.44 (m, 2H), 1.29-1.20 (m, 2H), 1.09-1.01 (m, 2H), 0.82 (t, 3H). LRMS [M+H]=499.3.

Example 4 methyl 3-((2-amino-4-(pentylamino)-5H-pyrrolo[3,2-d]pyrimidin-5-yl)methyl)-4-methoxybenzoate

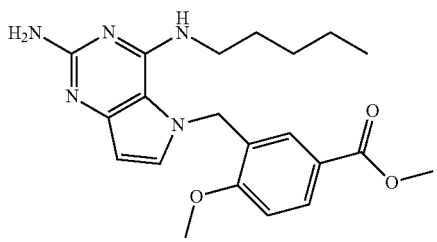 [SMILES: CCCCCNc1nc(N)nc2ccn(Cc3cc(C(=O)OC)ccc3OC)c12]

Step 1: Preparation of methyl 3-(bromomethyl)-4-methoxybenzoate

Methyl 3-(bromomethyl)-4-methoxybenzoate was prepared following the same protocol as methyl 4-(bromomethyl)-3-methoxybenzoate (Example 1, Step 1), using methyl 4-methoxy-3-methylbenzoate in place of methyl 3-methoxy-4-methylbenzoate.

Step 2: Preparation of methyl 3-((2-amino-4-(pentylamino)-5H-pyrrolo[3,2-d]pyrimidin-5-yl)methyl)-4-methoxybenzoate Methyl 3-((2-amino-4-(pentylamino)-5H-pyrrolo[3,2-d]pyrimidin-5-yl)methyl)-4-methoxybenzoate was prepared following the same protocol as Example 1, Step 2, using methyl 3-(bromomethyl)-4-methoxybenzoate (from the previous step) in place of methyl 4-(bromomethyl)-3-methoxybenzoate. $^1$H NMR (400 MHz, DMSO-$d_6$): δ 7.90 (dd, 1H), 7.30 (d, 1H), 7.18 (d, 1H), 7.14 (d, 1H), 6.04 (d, 1H), 5.96 (s, 1H), 5.66 (s, 2H), 5.48 (s, 2H), 3.94 (s, 3H), 3.72 (s, 3H), 3.32 (m, 2H), 1.46-1.38 (m, 2H), 1.20-1.10 (m, 2H), 1.03-0.95 (m, 2H), 0.77 (t, 3H). LRMS [M+H]=398.2.

Example 5 methyl 2-(3-((2-amino-4-(pentylamino)-5H-pyrrolo[3,2-d]pyrimidin-5-yl)methyl)-4-methoxyphenyl) acetate

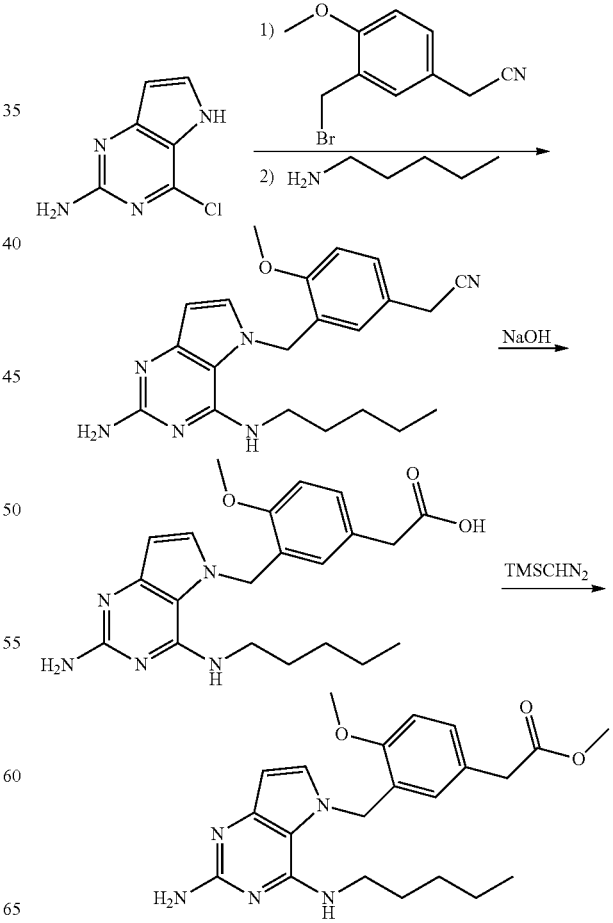

Step 1: Preparation of 2-(3-(bromomethyl)-4-methoxyphenyl)acetonitrile 2-(4-Methoxy-3-methylphenyl)acetonitrile (commercially available, 1.0 equiv.) was dissolved in carbon tetrachloride (0.1 M), and was treated with N-bromosuccinimide (1.1 equiv.) and benzoyl peroxide (catalytic amount). The reaction mixture was stirred at reflux overnight under irradiation of a 200 W floodlight. After cooling down to room temperature, the reaction mixture was purified by ISCO (silica gel column, EtOAc/hexanes) to afford 2-(3-(bromomethyl)-4-methoxyphenyl)acetonitrile as a white solid.

Step 2: Preparation of 2-(3-((2-amino-4-(pentylamino)-5H-pyrrolo[3,2-d]pyrimidin-5-yl)methyl)-4-methoxyphenyl)acetonitrile 2-(3-((2-Amino-4-(pentylamino)-5H-pyrrolo[3,2-d]pyrimidin-5-yl)methyl)-4-methoxyphenyl)acetonitrile was prepared following the same protocol as Example 1, Step 2, using 2-(3-(bromomethyl)-4-methoxyphenyl)acetonitrile (from previous step) in place of methyl 4-(bromomethyl)-3-methoxybenzoate. LRMS [M+H]=379.2.

Step 3: Preparation of 2-(3-((2-amino-4-(pentylamino)-5H-pyrrolo[3,2-d]pyrimidin-5-yl)methyl)-4-methoxyphenyl)acetic acid 2-(3-((2-Amino-4-(pentylamino)-5H-pyrrolo[3,2-d]pyrimidin-5-yl)methyl)-4-methoxyphenyl)acetonitrile (from previous step) was suspended in EtOH: 4N NaOH (v/v=1:2, 0.1 M). The reaction mixture was stirred at 80° C. overnight. After neutralization with 1 N HCl, 2-(3-((2-amino-4-(pentylamino)-5H-pyrrolo[3,2-d]pyrimidin-5-yl)methyl)-4-methoxyphenyl)acetic acid was collected by filtration as a white solid. $^1$H NMR (400 MHz, DMSO-$d_6$): δ (d-DMSO): δ 7.38 (d, 1H), 7.25 (br s, 2H), 7.19 (d, 1H), 7.01 (d, 1H), 6.64 (s, 1H), 6.56 (s, 1H), 6.17 (d, 1H), 5.50 (s, 2H), 3.81 (s, 3H), 3.52-3.42 (m, 2H), 3.38 (s, 2H), 1.50-1.43 (m, 2H), 1.29-1.20 (m, 2H), 1.16-1.07 (m, 2H), 0.82 (t, 3H). LRMS [M+H]=398.2.

Step 4: Preparation of methyl 2-(3-((2-amino-4-(pentylamino)-5H-pyrrolo[3,2-d]pyrimidin-5-yl)methyl)-4-methoxyphenyl)acetate To a suspension of 2-(3-((2-amino-4-(pentylamino)-5H-pyrrolo[3,2-d]pyrimidin-5-yl)methyl)-4-methoxyphenyl) acetic acid (1 equiv., from the previous step) in toluene and methanol (9:1 v/v, 1 M) was added trimethylsilyldiazomethane (2N solution in diethyl ether, 1.2 equiv.). The reaction mixture was stirred at room temperature overnight, and then was concentrated down to dryness. The crude was purified by ISCO (silica gel column) to afford the title compound as white solid. $^1$H NMR (CDCl$_3$): δ 7.23 (s, 1H), 7.12 (d, 1H), 6.93 (d, 1H), 6.64 (d, 1H), 6.33 (d, 1H), 5.32 (s, 2H), 3.91 (s, 3H), 3.63 (s, 3H), 3.47 (s, 2H), 3.38-3.33 (m, 2H), 1.38-1.29 (m, 2H), 1.27-1.20 (m, 2H), 1.11-1.05 (m, 2H), 0.85 (t, 3H). LRMS [M+H]=412.2.

Example 6 ethyl 3-(3-((2-amino-4-(pentylamino)-5H-pyrrolo[3,2-d]pyrimidin-5-yl)methyl)-4-methoxyphenyl) propanoate

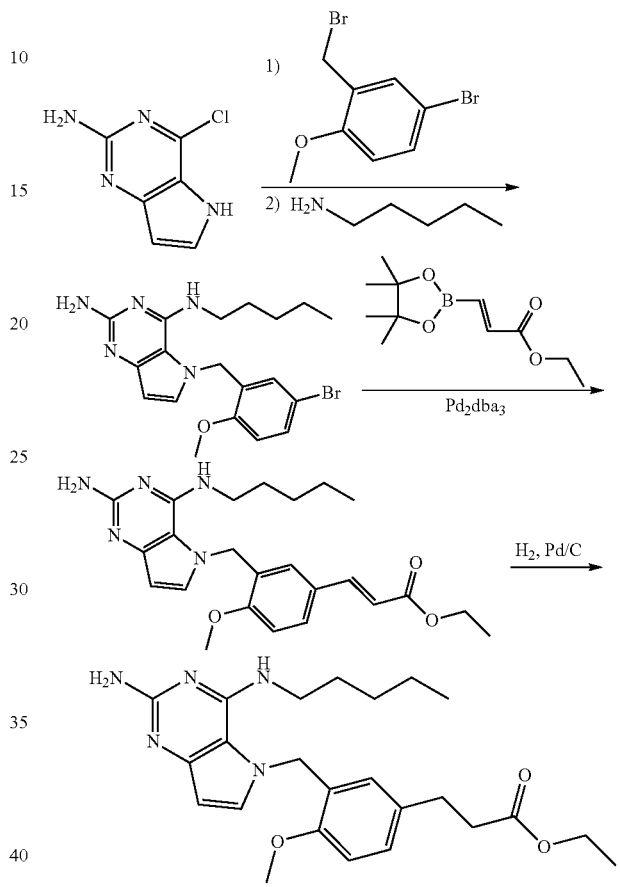

Step 1: Preparation of 4-bromo-2-(bromomethyl)-1-methoxybenzene

4-Bromo-2-(bromomethyl)-1-methoxybenzene was prepared following the same protocol as methyl 4-(bromomethyl)-3-methoxybenzoate (Example 1, Step 1), using 4-bromo-1-methoxy-2-methylbenzene (commercially available) in place of methyl 3-methoxy-4-methylbenzoate.

Step 2: Preparation of 5-(5-bromo-2-methoxybenzyl)-N4-pentyl-5H-pyrrolo[3,2-d]pyrimidine-2,4-diamine 5-(5-Bromo-2-methoxybenzyl)-N$^4$-pentyl-5H-pyrrolo[3,2-d]pyrimidine-2,4-diamine was prepared following the same protocol as Example 1, Step 2, using 4-bromo-2-(bromomethyl)-1-methoxybenzene (from the previous step) in place of methyl 4-(bromomethyl)-3-methoxybenzoate.

Step 3: Preparation of (E)-ethyl 3-(3-((2-amino-4-(pentylamino)-5H-pyrrolo[3,2-d]pyrimidin-5-yl)methyl)-4-methoxyphenyl)acrylate 5-(5-Bromo-2-methoxybenzyl)-N$^4$-pentyl-5H-pyrrolo[3,2-d]pyrimidine-2,4-diamine (from the previous step, 1 equiv.), (E)-ethyl 3-(4,4,5,5-tetramethyl-1,3,2-dioxaborolan-2-yl)acrylate (1.5 equiv.), tris(dibenzylideneacetone)dipalladium(0) (0.1 equiv.), 2-dicyclohexylphosphino-2',6'-dimethoxybiphenyl (Sphos, 0.2 equiv.) and K₃PO₄ (2 equiv.) were dissolved in 4:1 n-butanol:water (0.1 M). After degassing with N₂, the vessel was sealed and heated at 100° C. O/N. After cooling down to room temperature, the reaction mixture was quenched with equal volume of saturated sodium bicarbonate aqueous solution, and was extracted with DCM. The organic layers were combined and dried over anhydrous sodium sulfate, and concentrated in vacuuo. The crude was purified by reverse phase prep-HPLC to afford title compound as a white solid.

Step 4: Preparation of ethyl 3-(3-((2-amino-4-(pentylamino)-5H-pyrrolo[3,2-d]pyrimidin-5-yl)methyl)-4-methoxyphenyl) propanoate (E)-Ethyl 3-(3-((2-amino-4-(pentylamino)-5H-pyrrolo[3, 2-d]pyrimidin-5-yl)methyl)-4-methoxyphenyl)acrylate (from the previous step, 1 equiv.) and 10% palladium on carbon (0.1 equiv.) were suspended in ethanol (0.1 M). The mixture was stirred under H₂ atmosphere O/N with stirring. Solvents were removed under vacuuo, and the crude was purified by ISCO (DCM-EtOAc, silica gel) to afford product as white solid. ¹H NMR (CDCl3): δ 7.19 (d, 1H), 7.13 (d, 1H), 6.91 (d, 1H), 6.60 (s, 1H), 6.36 (d, 1H), 5.31 (s, 2H), 4.05 (q, 2H), 3.91 (s, 3H), 3.38 (t, 2H), 2.79 (t, 2H), 2.47 (t, 2H), 1.39-1.32 (m, 2H), 1.28-1.18 (m, 2H), 1.20 (t, 3H), 1.12-1.06 (m, 2H), 0.86 (t, 3H). LRMS [M+H]=440.3.

Example 7 methyl 2-(3-((2-amino-4-(pentylamino)-5H-pyrrolo [3,2-d]pyrimidin-5-yl)methyl)-4-methoxyphenyl)-2,2-difluoroacetate

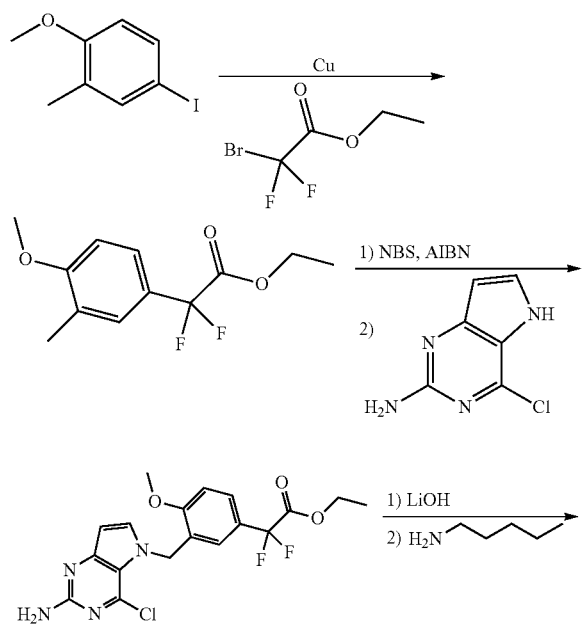

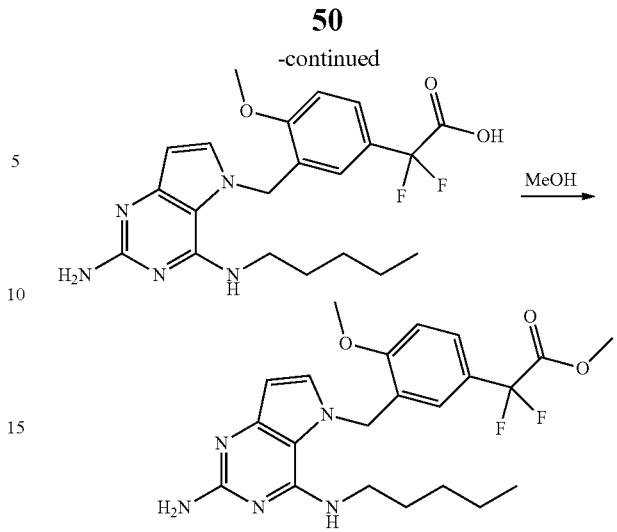

Step 1: Preparation of ethyl 2,2-difluoro-2-(4-methoxy-3-methylphenyl)acetate

To a solution 4-iodo-1-methoxy-2-methylbenzene (commercially available, 1 equiv) and ethyl 2-bromo-2,2-difluoroacetate (2 equiv) in DMF (0.3M) was added Cu powder (3 equiv). The reaction slurry was heated to 80° C. for 1.5 days, quenched with saturated NaH₂PO₄ (aq) and extracted with ethyl acetate. The organics were dried over Na₂SO₄ and concentrated under vacuum. The residual was purified via silica gel column chromatography to afford the title product.

Step 2: Preparation of ethyl 2-(3-((2-amino-4-chloro-5H-pyrrolo[3,2-d]pyrimidin-5-yl)methyl)-4-methoxyphenyl)-2,2-difluoroacetate Ethyl 2,2-difluoro-2-(4-methoxy-3-methylphenyl)acetate (from the previous step) was dissolved in CCl₄ (0.3 M). NBS (1.0 equiv.) and AIBN (0.05 equiv.) were added, and the reaction mixture was stirred at 80° C. for 2 hours. It was cooled down to room temperature and concentrated. The residue was purified with silica gel column chromatography to afford a colorless oil. To a solution of commercially available 4-chloro-5H-pyrrolo[3,2-d]pyrimidin-2-amine (1.0 equiv) and Cs₂CO₃ (1.3 equiv) in DMF was added the oil from above (1.0 equiv). The reaction mixture was stirred at room temperature for 5 hours. It was quenched with water and extracted with 10% MeOH/DCM (v/v). The combined organic extracts were concentrated and purified by silica gel column chromatography to afford the title compound as a white solid.

Step 3: Preparation of 2-(3-((2-amino-4-(pentylamino)-5H-pyrrolo[3,2-d]pyrimidin-5-yl)methyl)-4-methoxyphenyl)-2,2-difluoroacetic Acid To a solution of ethyl 2-(3-((2-amino-4-chloro-5H-pyrrolo[3,2-d]pyrimidin-5-yl)methyl)-4-methoxyphenyl)-2,2-difluoroacetate (from the previous step) in water/MeOH (1:1 v/v, 0.3 M) was added LiOH (1.4 equiv) and it was stirred for 10 min at room temperature. It was quenched with 1N HCl (1.0 equiv). The solution was concentrated and the residue was used crude for the next reaction. To a solution of the residue above in NMP (0.1 M) was added pentyl amine (3.0 equiv). The solution was heated at 100° C. for 2 hours and cooled down to room temperature for reverse phase HPLC purification to afford 2-(3-((2-amino-4-(pentylamino)-5H-pyrrolo[3,2-d]pyrimidin-5-yl)methyl)-4-methoxyphenyl)-2,2-difluoroacetic acid as a white solid.

Step 4: Preparation of methyl 2-(3-((2-amino-4-(pentylamino)-5H-pyrrolo[3,2-d]pyrimidin-5-yl)methyl)-4-methoxyphenyl)-2,2-difluoroacetate Methyl 2-(3-((2-amino-4-(pentylamino)-5H-pyrrolo[3,2-d]pyrimidin-5-yl)methyl)-4-methoxyphenyl)-2,2-difluoroacetate was prepared from 2-(3-((2-amino-4-(pentylamino)-5H-pyrrolo[3,2-d]pyrimidin-5-yl)methyl)-4-methoxyphenyl)-2,2-difluoroacetic acid (from the previous step) and methanol following the same protocol as Example 2, Step 2. $^1$H NMR (CD$_3$OD-CDCl$_3$): δ 7.53 (d, 1H), 7.10 (d, 1H), 6.99 (d, 1H), 6.93 (s, 1H), 6.29 (d, 1H), 5.31 (s, 2H), 3.90 (s, 3H), 3.35 (m, 2H), 1.36-1.28 (m, 2H), 1.23-1.13 (m, 2H), 1.06-0.98 (m, 2H), 0.77 (t, 3H). LRMS [M+H]=448.2.

Example 8

2-morpholino-2-oxoethyl 2-(3-((2-amino-4-(pentylamino)-5H-pyrrolo[3,2-d]pyrimidin-5-yl)methyl)-4-methoxyphenoxy)acetate

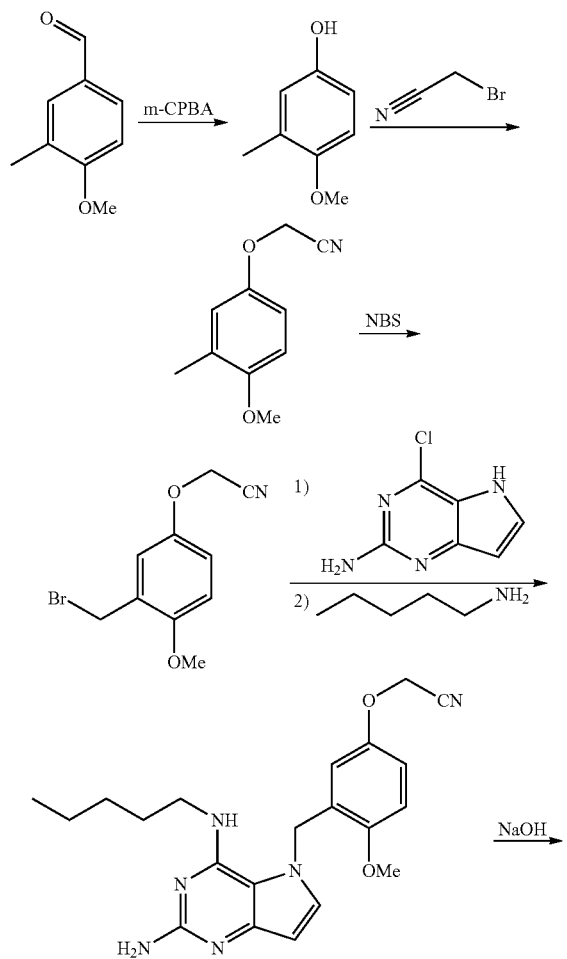

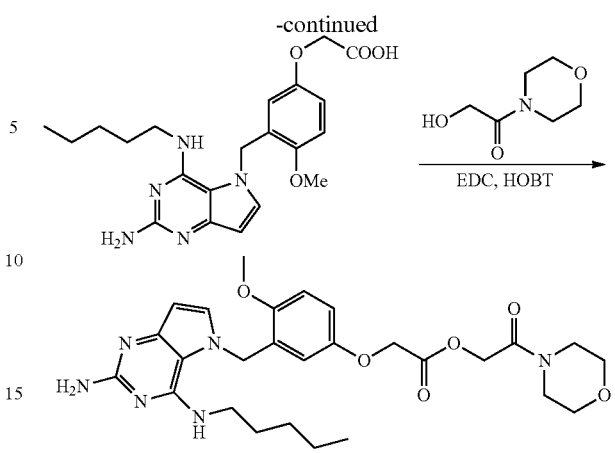

Step 1: Preparation of 4-methoxy-3-methylphenol

4-Methoxy-3-methylbenzaldehyde (commercially available, 1 equiv.) was dissolved in DCM (0.4 M), and m-CPBA (2.4 equiv.) was added slowly. The reaction mixture was stirred at r.t. for 18 h, monitored by LCMS analysis. An excessive amount of aqueous sodium thiosulfate solution was added. After an addition of equal volume of 1:1 2N NaOH and methanol, the mixture was stirred for 30 minutes and neutralized to pH 7-8 with 1N HCl and aqueous NaHCO$_3$, then extracted with DCM, and concentrated. The crude was purified by ISCO (ethyl acetate/hexane, silica gel) to afford the title product.

Step 2: Preparation of 2-(4-methoxy-3-methylphenoxy)acetonitrile

4-Methoxy-3-methylphenol (from the previous step, 1 equiv.) was dissolved in DMF (0.5 M), cesium carbonate (2.5 equiv.) was added and stirred at r.t. for 30 min. Then bromoacetonitrile (4 equiv.) was added and the reaction mixture was stirred at r.t. o/n, monitored by LCMS analysis. The reaction mixture was filtered through silica gel. After the organic solvent was evaporated, the residue was purified on ISCO (ethyl acetate/hexane, silical gel) to afford the title compound.

Step 3: Preparation of 2-(3-(bromomethyl)-4-methoxyphenoxy)acetonitrile 2-(3-(Bromomethyl)-4-methoxyphenoxy)acetonitrile was prepared following the same protocol as methyl 4-(bromomethyl)-3-methoxybenzoate (Example 1, Step 1), using 2-(4-methoxy-3-methylphenoxy)acetonitrile (from the previous step) in place of methyl 3-methoxy-4-methylbenzoate.

Step 4: Preparation of 2-(3-((2-amino-4-(pentylamino)-5H-pyrrolo[3,2-d]pyrimidin-5-yl)methyl)-4-methoxyphenoxy)acetonitrile 2-(3-((2-Amino-4-(pentylamino)-5H-pyrrolo[3,2-d]pyrimidin-5-yl)methyl)-4-methoxyphenoxy)acetonitrile was prepared following the same protocol as Example 1, Step 2, using 2-(3-(bromomethyl)-4-methoxyphenoxy)acetonitrile in place of methyl 4-(bromomethyl)-3-methoxybenzoate.

Step 5: Preparation of 2-(3-((2-amino-4-(pentylamino)-5H-pyrrolo[3,2-d]pyrimidin-5-yl)methyl)-4-methoxyphenoxy)acetic Acid 2-(3-((2-Amino-4-(pentylamino)-5H-pyrrolo[3,2-d]pyrimidin-5-yl)methyl)-4-methoxyphenoxy)acetic acid was prepared following the same protocol as 2-(3-((2-amino-4-(pentylamino)-5H-pyrrolo[3,2-d]pyrimidin-5-yl)methyl)-4-methoxyphenyl)acetic acid (Example 5, Step 3, using 2-(3-((2-amino-4-(pentylamino)-5H-pyrrolo[3,2-d]pyrimidin-5-yl)methyl)-4-methoxyphenoxy)acetonitrile (from the previous step) in place of 2-(3-((2-amino-4-(pentylamino)-5H-pyrrolo[3,2-d]pyrimidin-5-yl)methyl)-4-methoxyphenyl)acetonitrile.

Step 6: Preparation of 2-morpholino-2-oxoethyl 2-(3-((2-amino-4-(pentylamino)-5H-pyrrolo[3,2-d]pyrimidin-5-yl)methyl)-4-methoxyphenoxy)acetate 2-Morpholino-2-oxoethyl 2-(3-((2-amino-4-(pentylamino)-5H-pyrrolo[3,2-d]pyrimidin-5-yl)methyl)-4-methoxyphenoxy)acetate was prepared from 2-(3-((2-amino-4-(pentylamino)-5H-pyrrolo[3,2-d]pyrimidin-5-yl)methyl)-4-methoxyphenoxy)acetic acid (previous step) and 2-hydroxy-1-morpholinoethanone in place of 2-(dimethylamino)ethyl alcohol following the same protocol as Example 2, Step 2. $^1$H NMR (CD$_3$OD): δ 7.35 (d, 1H), 7.01 (d, 1H), 6.95 (d, 1H), 6.31 (s, 1H), 6.19 (d, 1H), 5.46 (s, 2H), 4.85 (s, 2H), 4.66 (s, 2H), 3.87 (s, 3H), 3.69-3.64 (m, 4H), 3.55 (t, 2H), 3.48-3.44 (m, 4H), 1.50-1.43 (m, 2H), 1.33-1.24 (m, 2H), 1.17-1.10 (m, 2H), 0.87 (t, 3H). LRMS [M+H]=541.3.

Example 9

2-morpholino-2-oxoethyl 2-(3-((2-amino-4-(pentylamino)-5H-pyrrolo[3,2-d]pyrimidin-5-yl)methyl)-4-methoxyphenyl)acetate

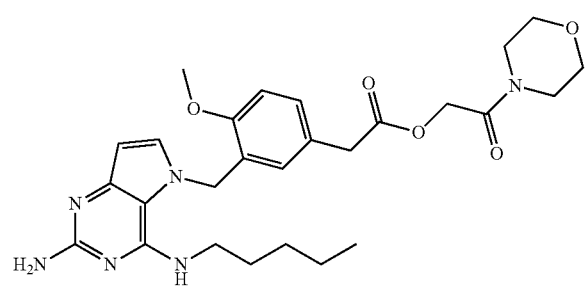 [SMILES: CCCCCNc1nc(N)nc2ccn(Cc3cc(CC(=O)OCC(=O)N4CCOCC4)ccc3OC)c12]

Preparation of 2-morpholino-2-oxoethyl 2-(3-((2-amino-4-(pentylamino)-5H-pyrrolo[3,2-d]pyrimidin-5-yl)methyl)-4-methoxyphenyl)acetate 2-Morpholino-2-oxoethyl 2-(3-((2-amino-4-(pentylamino)-5H-pyrrolo[3,2-d]pyrimidin-5-yl)methyl)-4-methoxyphenyl)acetate was prepared from 2-(3-((2-amino-4-(pentylamino)-5H-pyrrolo[3,2-d]pyrimidin-5-yl)methyl)-4-methoxyphenyl)acetic acid (Example 5, Step 3) and 2-hydroxy-1-morpholinoethanone following the same protocol as 2-(dimethylamino)ethyl 4-((2-amino-4-(pentylamino)-5H-pyrrolo[3,2-d]pyrimidin-5-yl)methyl)-3-methoxybenzoate (Example 2, Step 2). $^1$H NMR (CD3OD): δ 7.28 (d, 1H), 7.25 (d, 1H), 7.04 (d, 1H), 6.63 (s, 1H), 6.13 (d, 1H), 5.44 (s, 2H), 4.69 (s, 2H), 3.92 (s, 3H), 3.65 (t, 4H), 3.59 (s, 2H), 3.53 (t, 2H), 3.42 (t, 2H), 3.38 (t, 2H), 1.43-1.36 (m, 2H), 1.30-1.22 (m, 2H), 1.14-1.06 (m, 2H), 0.87 (t, 3H). LRMS [M+H]=525.3.

Example 10

2-morpholino-2-oxoethyl 2-(4-((2-amino-4-(pentylamino)-5H-pyrrolo[3,2-d]pyrimidin-5-yl)methyl)-3-methoxyphenyl)acetate

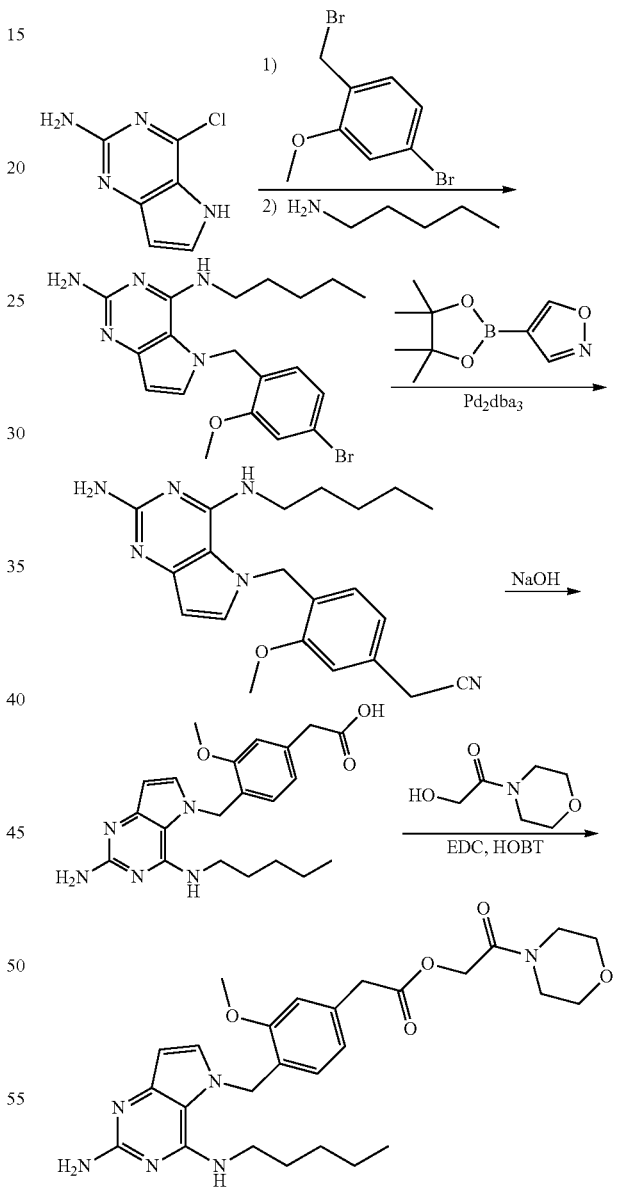

Step 1: Preparation of 4-bromo-1-(bromomethyl)-2-methoxybenzene

4-Bromo-1-(bromomethyl)-2-methoxybenzene was prepared following the same protocol as methyl 4-(bromomethyl)-3-methoxybenzoate (Example 1, Step 1), using 4-bromo-2-methoxy-1-methylbenzene (commercially available) in place of methyl 3-methoxy-4-methylbenzoate.

Step 2: Preparation of 5-(4-bromo-2-methoxybenzyl)-N4-pentyl-5H-pyrrolo[3,2-d]pyrimidine-2,4-diamine 5-(4-Bromo-2-methoxybenzyl)-N$^4$-pentyl-5H-pyrrolo[3,2-d]pyrimidine-2,4-diamine was prepared following the same protocol as Example 1, Step 2, using 4-bromo-1-(bromomethyl)-2-methoxybenzene (from the previous step) in place of methyl 4-(bromomethyl)-3-methoxybenzoate.

Step 3: Preparation of 2-(4-((2-amino-4-(pentylamino)-5H-pyrrolo[3,2-d]pyrimidin-5-yl)methyl)-3-methoxyphenyl)acetonitrile 5-(4-bromo-2-methoxybenzyl)-N$^4$-pentyl-5H-pyrrolo[3,2-d]pyrimidine-2,4-diamine (from the previous step, 1 equiv.), 4-(4,4,5,5-tetramethyl-1,3,2-dioxaborolan-2-yl)isoxazole (1.2 equiv.), PdCl$_2$(dppf) (0.1 equiv.), KF (1N solution, 3 equiv.) were added to DMSO (0.2M). The vessel was sealed and heated at 130° C. O/N. After cooling down to room temperature, the reaction mixture was filtered and then purified by reverse phase prep-HPLC to afford title compound as a brownish solid.

Step 4: Preparation of 2-(4-((2-amino-4-(pentylamino)-5H-pyrrolo[3,2-d]pyrimidin-5-yl)methyl)-3-methoxyphenyl)acetic Acid 2-(4-((2-Amino-4-(pentylamino)-5H-pyrrolo[3,2-d]pyrimidin-5-yl)methyl)-3-methoxyphenyl)acetic acid was prepared following the same protocol as 2-(3-((2-amino-4-(pentylamino)-5H-pyrrolo[3,2-d]pyrimidin-5-yl)methyl)-4-methoxyphenyl)acetic acid (Example 5, Step 3), using 2-(4-((2-amino-4-(pentylamino)-5H-pyrrolo[3,2-d]pyrimidin-5-yl)methyl)-3-methoxyphenyl)acetonitrile (from the previous step) in place of 2-(3-((2-amino-4-(pentylamino)-5H-pyrrolo[3,2-d]pyrimidin-5-yl)methyl)-4-methoxyphenyl)acetonitrile.

Step 5: Preparation of 2-morpholino-2-oxoethyl 2-(4-((2-amino-4-(pentylamino)-5H-pyrrolo[3,2-d]pyrimidin-5-yl)methyl)-3-methoxyphenyl)acetate 2-morpholino-2-oxoethyl 2-(4-((2-amino-4-(pentylamino)-5H-pyrrolo[3,2-d]pyrimidin-5-yl)methyl)-3-methoxyphenyl)acetate was prepared from 2-(4-((2-amino-4-(pentylamino)-5H-pyrrolo[3,2-d]pyrimidin-5-yl)methyl)-3-methoxyphenyl)acetic acid (previous step) and 2-hydroxy-1-morpholinoethanone following the same protocol as Example 2, Step 2. $^1$H NMR (CD$_3$OD): δ 7.25 (d, 1H), 7.09 (s, 1H), 6.83 (d, 1H), 6.59 (d, 1H), 6.12 (d, 1H), 5.42 (s, 2H), 4.84 (s, 2H), 3.94 (s, 3H), 3.77 (s, 2H), 3.65 (t, 4H), 3.55 (t, 2H), 3.43 (t, 2H), 3.37 (t, 2H), 1.45-1.38 (m, 2H), 1.30-1.23 (m, 2H), 1.17-1.09 (m, 2H), 0.87 (t, 3H). LRMS [M+H]= 525.3.

Example 11

2-(morpholin-4-yl)-2-oxoethyl 3-(4-{[2-amino-4-(pentylamino)-5H-pyrrolo[3,2-d]pyrimidin-5-yl]methyl}-3-methoxyphenyl) propanoate

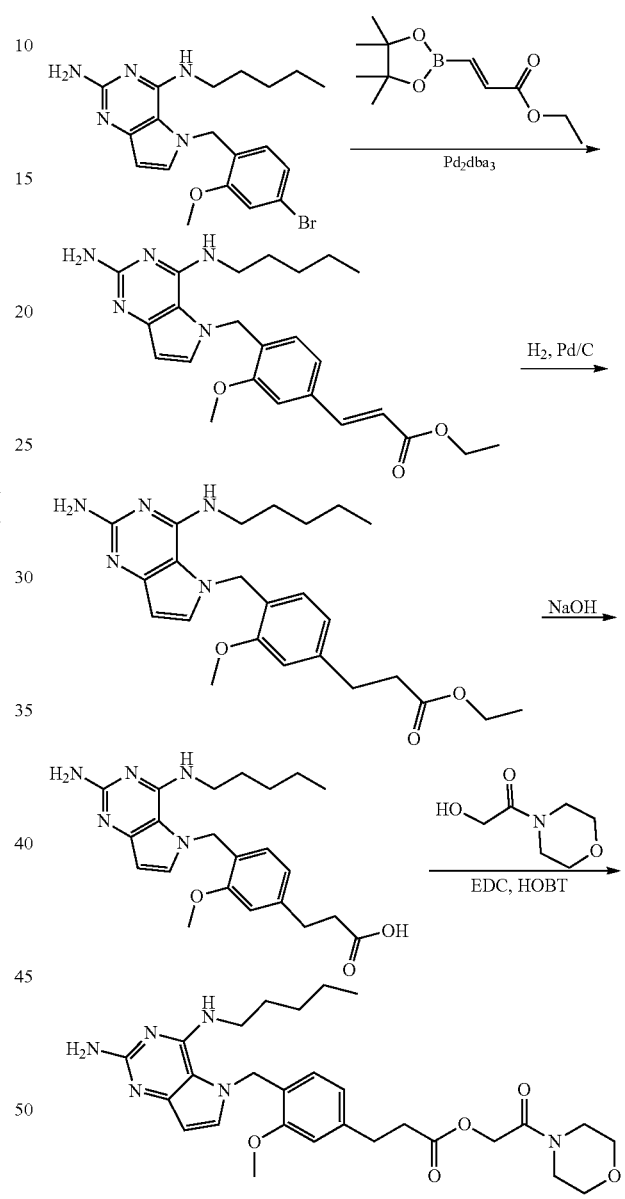

Step 1: Preparation of (E)-ethyl 3-(4-((2-amino-4-(pentylamino)-5H-pyrrolo[3,2-d]pyrimidin-5-yl)methyl)-3-methoxyphenyl)acrylate (E)-Ethyl 3-(4-((2-amino-4-(pentylamino)-5H-pyrrolo[3,2-d]pyrimidin-5-yl)methyl)-3-methoxyphenyl)acrylate was prepared from 5-(4-bromo-2-methoxybenzyl)-N$^4$-pentyl-5H-pyrrolo[3,2-d]pyrimidine-2,4-diamine (Example 10, Step 2) following the same protocol as (E)-ethyl 3-(3-((2-amino-4-(pentylamino)-5H-pyrrolo[3,2-d]pyrimidin-5-yl)methyl)-4-methoxyphenyl)acrylate (Example 6, Step 3).

Step 2: Preparation of ethyl 3-(4-((2-amino-4-(pentylamino)-5H-pyrrolo[3,2-d]pyrimidin-5-yl)methyl)-3-methoxyphenyl) propanoate Ethyl 3-(4-((2-amino-4-(pentylamino)-5H-pyrrolo[3,2-d]pyrimidin-5-yl)methyl)-3-methoxyphenyl)propanoate was prepared from (E)-ethyl 3-(4-((2-amino-4-(pentylamino)-5H-pyrrolo[3,2-d]pyrimidin-5-yl)methyl)-3-methoxyphenyl)acrylate (previous step) following the same protocol as (E)-ethyl 3-(3-((2-amino-4-(pentylamino)-5H-pyrrolo[3,2-d]pyrimidin-5-yl)methyl)-4-methoxyphenyl)acrylate (Example 6, Step 4).

Step 3: Preparation of 3-(4-((2-amino-4-(pentylamino)-5H-pyrrolo[3,2-d]pyrimidin-5-yl)methyl)-3-methoxyphenyl)propanoic Acid 3-(4-((2-Amino-4-(pentylamino)-5H-pyrrolo[3,2-d]pyrimidin-5-yl)methyl)-3-methoxyphenyl)propanoic acid was prepared from ethyl 3-(4-((2-amino-4-(pentylamino)-5H-pyrrolo[3,2-d]pyrimidin-5-yl)methyl)-3-methoxyphenyl)propanoate (previous step) following the same protocol as 2-(3-((2-amino-4-(pentylamino)-5H-pyrrolo[3,2-d]pyrimidin-5-yl)methyl)-4-methoxyphenoxy)acetic acid (Example 8, Step 5).

Step 4: Preparation of 2-morpholino-2-oxoethyl 3-(4-((2-amino-4-(pentylamino)-5H-pyrrolo[3,2-d]pyrimidin-5-yl)methyl)-3-methoxyphenyl)propanoate 2-Morpholino-2-oxoethyl 3-(4-((2-amino-4-(pentylamino)-5H-pyrrolo[3,2-d]pyrimidin-5-yl)methyl)-3-methoxyphenyl)propanoate was prepared from 3-(4-((2-amino-4-(pentylamino)-5H-pyrrolo[3,2-d]pyrimidin-5-yl)methyl)-3-methoxyphenyl)propanoic acid (previous step) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6). $^1$H NMR (CD$_3$OD): δ 7.36 (d, 1H), 7.00 (s, 1H), 6.81 (d, 1H), 6.67 (d, 1H), 6.20 (d, 1H), 5.48 (s, 2H), 4.82 (s, 2H), 3.91 (s, 3H), 3.65 (t, 4H), 3.56-3.41 (m, 6H), 2.97 (t, 2H), 2.76 (t, 2H), 1.52-1.45 (m, 2H), 1.34-1.25 (m, 2H), 1.20-1.11 (m, 2H), 0.88 (t, 3H). LRMS [M+H]=539.3.

Example 12

(S)-2-morpholino-2-oxoethyl 3-(3-((2-amino-4-((1-hydroxyhexan-2-yl)amino)-5H-pyrrolo[3,2-d]pyrimidin-5-yl)methyl)-4-methoxyphenyl) propanoate

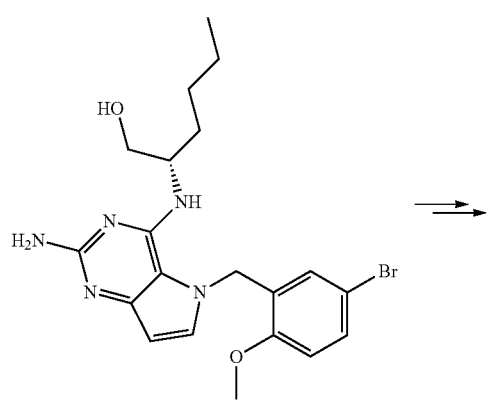

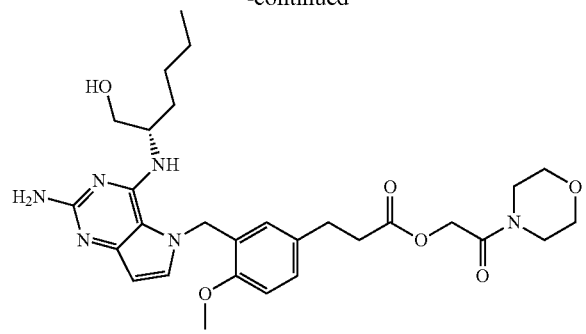

Step 1: Preparation of (S)-2-((2-amino-5-(5-bromo-2-methoxybenzyl)-5H-pyrrolo[3,2-d]pyrimidin-4-yl)amino)hexan-1-ol (S)-2-((2-Amino-5-(5-bromo-2-methoxybenzyl)-5H-pyrrolo[3,2-d]pyrimidin-4-yl)amino)hexan-1-ol was prepared following the same protocol as methyl 4-((2-amino-4-(pentylamino)-5H-pyrrolo[3,2-d]pyrimidin-5-yl)methyl)-3-methoxybenzoate (Example 1), using (S)-2-aminohexan-1-ol (commercially available) in place of N-pentyl amine, and 4-Bromo-1-(bromomethyl)-2-methoxybenzene (Example 10, Step 1) in place of methyl 4-(bromomethyl)-3-methoxybenzoate.

Step 2: Preparation of (S)-2-morpholino-2-oxoethyl 3-(3-((2-amino-4-((1-hydroxyhexan-2-yl)amino)-5H-pyrrolo[3,2-d]pyrimidin-5-yl)methyl)-4-methoxyphenyl) propanoate (S)-2-Morpholino-2-oxoethyl 3-(3-((2-amino-4-((1-hydroxyhexan-2-yl)amino)-5H-pyrrolo[3,2-d]pyrimidin-5-yl)methyl)-4-methoxyphenyl)propanoate was prepared following the same protocol as (E)-ethyl 3-(4-((2-amino-4-(pentylamino)-5H-pyrrolo[3,2-d]pyrimidin-5-yl)methyl)-3-methoxyphenyl)acrylate (Example 11, Steps 1-4), using (S)-2-((2-amino-5-(5-bromo-2-methoxybenzyl)-5H-pyrrolo[3,2-d]pyrimidin-4-yl)amino)hexan-1-ol (from previous step) in place of 5-(4-bromo-2-methoxybenzyl)-N$^4$-pentyl-5H-pyrrolo[3,2-d]pyrimidine-2,4-diamine. $^1$H NMR (CDCl$_3$): δ 7.12 (d, 1H), 7.05 (d, 1H), 6.82 (d, 1H), 6.50 (s, 1H), 6.20 (d, 1H), 5.49 (d, 1H), 5.33 (dd, 2H), 4.56 (s, 2H), 4.20 (m, 1H), 3.82 (s, 3H), 3.64-3.60 (m, 4H), 3.54-3.29 (m, 6H), 2.85-2.71 (m, 2H), 2.62-2.50 (m, 2H), 1.40-0.85 (m, 6H), 0.75 (m, 3H). LRMS [M+H]=569.3.

Example 13

(S)-2-morpholino-2-oxoethyl 2-(4-((2-amino-4-((1-hydroxyhexan-2-yl)amino)-5H-pyrrolo[3,2-d]pyrimidin-5-yl)methyl)-3-methoxyphenyl)acetate

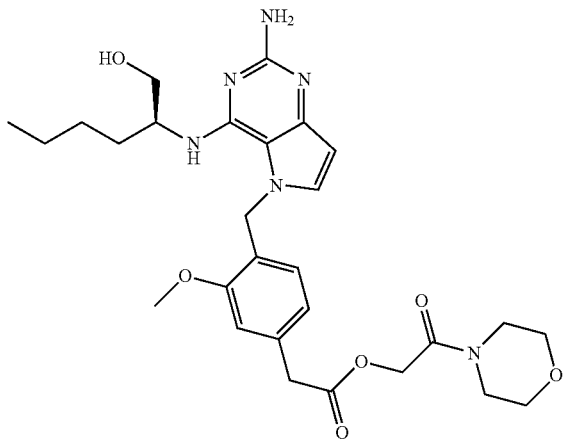 [SMILES: CCCC[C@@H](CO)Nc1nc(N)nc2ccn(Cc3ccc(CC(=O)OCC(=O)N4CCOCC4)cc3OC)c12]

(S)-2-morpholino-2-oxoethyl 2-(4-((2-amino-4-((1-hydroxyhexan-2-yl)amino)-5H-pyrrolo[3,2-d]pyrimidin-5-yl)methyl)-3-methoxyphenyl)acetate (S)-2-Morpholino-2-oxoethyl 2-(4-((2-amino-4-((1-hydroxyhexan-2-yl)amino)-5H-pyrrolo[3,2-d]pyrimidin-5-yl)methyl)-3-methoxyphenyl)acetate was prepared following the same protocol as 2-morpholino-2-oxoethyl 2-(3-((2-amino-4-(pentylamino)-5H-pyrrolo[3,2-d]pyrimidin-5-yl)methyl)-4-methoxyphenyl)acetate (Example 10), using (S)-2-aminohexan-1-ol (commercially available) in place of N-pentyl amine. $^1$H NMR (CD$_3$OD) b 7.50 (d, 1H), 7.13 (s, 1H), 6.88 (d, 1H), 6.60 (d, 1H), 6.25 (d, 1H), 5.65 (d, 1H), 5.42 (d, 1H), 4.86 (s, 2H), 4.42-4.36 (m, 2H), 3.94 (s, 3H), 3.79 (s, 2H), 3.64 (t, 4H), 3.55 (t, 2H), 3.51-3.48 (m, 1H), 3.44 (t, 2H), 1.52-1.44 (m, 2H), 1.29-1.14 (m, 2H), 1.05-0.91 (m, 2H), 0.82 (t, 3H). LRMS [M+H]=555.3.

Example 14

(S)-2-morpholino-2-oxoethyl 2-(3-((2-amino-4-((1-hydroxyhexan-2-yl)amino)-5H-pyrrolo[3,2-d]pyrimidin-5-yl)methyl)-4-methoxyphenyl)acetate

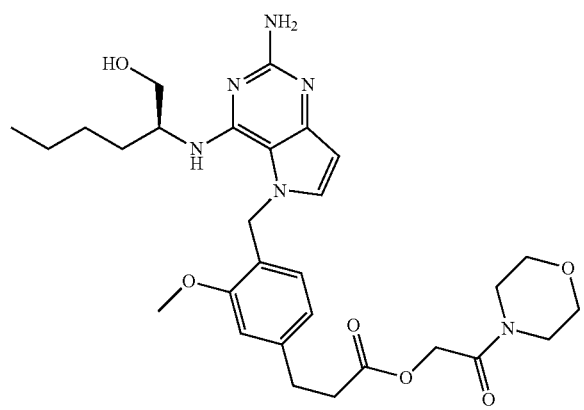 [SMILES: CCCC[C@@H](CO)Nc1nc(N)nc2ccn(Cc3ccc(CCC(=O)OCC(=O)N4CCOCC4)cc3OC)c12]

(S)-2-morpholino-2-oxoethyl 2-(3-((2-amino-4-((1-hydroxyhexan-2-yl)amino)-5H-pyrrolo[3,2-d]pyrimidin-5-yl)methyl)-4-methoxyphenyl)acetate (S)-2-Morpholino-2-oxoethyl 2-(3-((2-amino-4-((1-hydroxyhexan-2-yl)amino)-5H-pyrrolo[3,2-d]pyrimidin-5-yl)methyl)-4-methoxyphenyl)acetate was prepared following the same protocol as 2-morpholino-2-oxoethyl 2-(3-((2-amino-4-(pentylamino)-5H-pyrrolo[3,2-d]pyrimidin-5-yl)methyl)-4-methoxyphenyl)acetate (Example 9), using (S)-2-aminohexan-1-ol (commercially available) in place of N-pentyl amine. $^1$H NMR (CDCl$_3$): δ 7.20 (d, 1H), 7.03 (d, 1H), 6.85 (d, 1H), 6.57 (s, 1H), 6.17 (d, 1H), 5.27 (s, 2H), 5.08 (s, 2H), 4.89 (d, 1H), 4.56 (q, 2H), 4.04 (m, 1H), 3.83 (s, 3H), 3.62-3.58 (m, 4H), 3.54-3.49 (m, 4H), 3.30-3.24 (m, 2H), 1.35-0.95 (m, 6H), 0.76 (t, 3H). LRMS [M+H]=555.3.

Example 15

(S)-2-morpholino-2-oxoethyl 3-(4-((2-amino-4-((1-hydroxyhexan-2-yl)amino)-5H-pyrrolo[3,2-d]pyrimidin-5-yl)methyl)-3-methoxyphenyl)propanoate

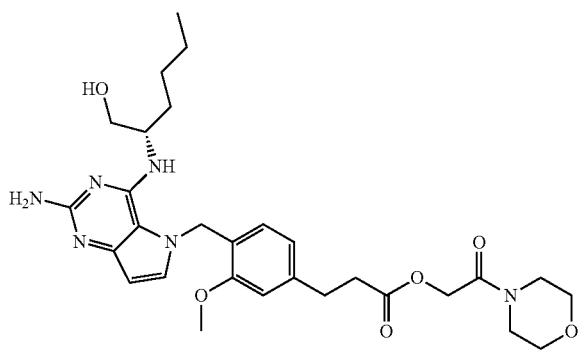 [SMILES: CCCC[C@@H](CO)Nc1nc(N)nc2ccn(Cc3ccc(CCC(=O)OCC(=O)N4CCOCC4)cc3OC)c12]

(S)-2-Morpholino-2-oxoethyl 3-(4-((2-amino-4-((1-hydroxyhexan-2-yl)amino)-5H-pyrrolo[3,2-d]pyrimidin-5-yl)methyl)-3-methoxyphenyl)propanoate (S)-2-Morpholino-2-oxoethyl 3-(4-((2-amino-4-((1-hydroxyhexan-2-yl)amino)-5H-pyrrolo[3,2-d]pyrimidin-5-yl)methyl)-3-methoxyphenyl)propanoate was prepared following the same protocol as 2-morpholino-2-oxoethyl 3-(3-((2-amino-4-(pentylamino)-5H-pyrrolo[3,2-d]pyrimidin-5-yl)methyl)-4-methoxyphenyl)propanoate (Example 17), using (S)-2-aminohexan-1-ol (commercially available) in place of N-pentyl amine. $^1$H NMR (CD$_3$OD): δ 7.34 (d, 1H), 6.99 (s, 1H), 6.78 (d, 1H), 6.51 (d, 1H), 6.16 (d, 1H), 5.56 (d, 1H), 5.32 (d, 1H), 4.82 (s, 2H), 4.28-4.22 (m, 2H), 3.93 (s, 3H), 3.66 (t, 4H), 3.55 (t, 1H), 3.46-3.43 (m, 4H), 2.96 (t, 2H), 2.75 (t, 2H), 1.50-1.42 (m, 2H), 1.25-1.09 (m, 2H), 1.02-0.90 (m, 2H), 0.82 (t, 3H). LRMS [M+H]=569.3.

Example 16

2-(morpholin-4-yl)-2-oxoethyl (2E)-3-(3-{[2-amino-4-(pentylamino)-5H-pyrrolo[3,2-d]pyrimidin-5-yl]methyl}-4-methoxyphenyl)prop-2-enoate

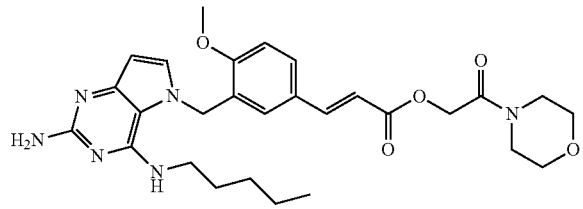 [SMILES: CCCCCNc1nc(N)nc2ccn(Cc3cc(/C=C/C(=O)OCC(=O)N4CCOCC4)ccc3OC)c12]

Step 1: Preparation of (E)-3-(3-((2-amino-4-(pentylamino)-5H-pyrrolo[3,2-d]pyrimidin-5-yl)methyl)-4-methoxyphenyl)acrylic Acid (E)-3-(3-((2-amino-4-(pentylamino)-5H-pyrrolo[3,2-d]pyrimidin-5-yl)methyl)-4-methoxyphenyl)acrylic acid was prepared from (E)-ethyl 3-(3-((2-amino-4-(pentylamino)-5H-pyrrolo[3,2-d]pyrimidin-5-yl)methyl)-4-methoxyphenyl)acrylate (Example 6, Step 3) following the same protocol as 2-(3-((2-amino-4-(pentylamino)-5H-pyrrolo[3,2-d]pyrimidin-5-yl)methyl)-4-methoxyphenoxy)acetic acid (Example 8, Step 5).

Step 2: Preparation of (E)-2-morpholino-2-oxoethyl 3-(3-((2-amino-4-(pentylamino)-5H-pyrrolo[3,2-d]pyrimidin-5-yl)methyl)-4-methoxyphenyl)acrylate (E)-2-morpholino-2-oxoethyl 3-(3-((2-amino-4-(pentylamino)-5H-pyrrolo[3,2-d]pyrimidin-5-yl)methyl)-4-methoxyphenyl)acrylate was prepared from (E)-3-(3-((2-amino-4-(pentylamino)-5H-pyrrolo[3,2-d]pyrimidin-5-yl)methyl)-4-methoxyphenyl)acrylic acid (previous step) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6). $^1$H NMR (CD$_3$OD): δ 7.61 (d, 1H), 7.39 (d, 1H), 7.27 (d, 1H), 7.14 (d, 1H), 6.95 (s, 1H), 6.32 (d, 1H), 6.25 (d, 1H), 5.55 (s, 2H), 4.91 (s, 2H), 3.94 (s, 3H), 3.70-3.66 (m, 4H), 3.58-3.48 (m, 6H), 1.52-1.45 (m, 2H), 1.29-1.21 (m, 2H), 1.14-1.08 (m, 2H), 0.84 (t, 3H). LRMS [M+H]= 537.3.

Example 17

2-(morpholin-4-yl)-2-oxoethyl 3-(3-{[2-amino-4-(pentylamino)-5H-pyrrolo[3,2-d]pyrimidin-5-yl]methyl}-4-methoxyphenyl) propanoate

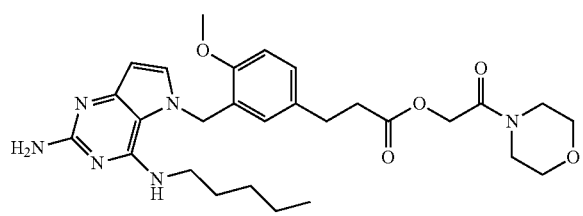 [SMILES: CCCCCNc1nc(N)nc2ccn(Cc3cc(CCC(=O)OCC(=O)N4CCOCC4)ccc3OC)c12]

Step 1: Preparation of 3-(3-((2-amino-4-(pentylamino)-5H-pyrrolo[3,2-d]pyrimidin-5-yl)methyl)-4-methoxyphenyl)propanoic Acid 3-(3-((2-Amino-4-(pentylamino)-5H-pyrrolo[3,2-d]pyrimidin-5-yl)methyl)-4-methoxyphenyl)propanoic acid was prepared from ethyl 3-(3-((2-amino-4-(pentylamino)-5H-pyrrolo[3,2-d]pyrimidin-5-yl)methyl)-4-methoxyphenyl)propanoate (Example 6) following the same protocol as 2-(3-((2-amino-4-(pentylamino)-5H-pyrrolo[3,2-d]pyrimidin-5-yl)methyl)-4-methoxyphenoxy)acetic acid (Example 8, Step 5).

Step 2: Preparation of 2-morpholino-2-oxoethyl 3-(3-((2-amino-4-(pentylamino)-5H-pyrrolo[3,2-d]pyrimidin-5-yl)methyl)-4-methoxyphenyl)propanoate 2-Morpholino-2-oxoethyl 3-(3-((2-amino-4-(pentylamino)-5H-pyrrolo[3,2-d]pyrimidin-5-yl)methyl)-4-methoxyphenyl)propanoate was prepared from 3-(3-((2-amino-4-(pentylamino)-5H-pyrrolo[3,2-d]pyrimidin-5-yl)methyl)-4-methoxyphenyl)propanoic acid (previous step) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6). $^1$H NMR (CDCl$_3$): δ 7.38 (d, 1H), 7.23 (d, 1H), 7.01 (d, 1H), 6.69 (s, 1H), 6.21 (d, 1H), 5.49 (s, 2H), 4.76 (s, 2H), 3.89 (s, 3H), 3.67-3.64 (m, 4H), 3.58-3.49 (m, 4H), 3.43 (t, 2H), 2.82 (t, 2H), 2.62 (t, 2H), 1.54-1.42 (m, 2H), 1.35-1.24 (m, 2H), 1.18-1.10 (m, 2H), 0.88 (t, 3H). LRMS [M+H]= 539.3.

Example 18

2-(benzyloxy)-2-oxoethyl 2-(4-{[2-amino-4-(pentylamino)-5H-pyrrolo[3,2-d]pyrimidin-5-yl]methyl}-3-methoxyphenyl)acetate

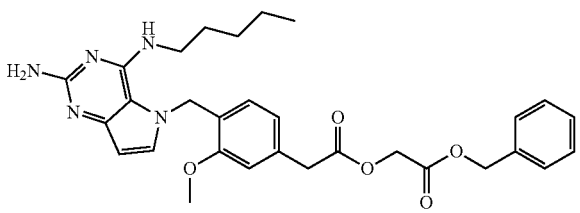 [SMILES: CCCCCNc1nc(N)nc2ccn(Cc3ccc(CC(=O)OCC(=O)OCc4ccccc4)cc3OC)c12]

Preparation of benzyl 2-(2-(4-((2-amino-4-(pentylamino)-5H-pyrrolo[3,2-d]pyrimidin-5-yl)methyl)-3-methoxyphenyl)acetoxy)acetate Benzyl 2-(2-(4-((2-amino-4-(pentylamino)-5H-pyrrolo[3,2-d]pyrimidin-5-yl)methyl)-3-methoxyphenyl)acetoxy)acetate was prepared from 2-(4-((2-amino-4-(pentylamino)-5H-pyrrolo[3,2-d]pyrimidin-5-yl)methyl)-3-methoxyphenyl)acetic acid (Example 10, Step 4) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6), using benzyl 2-hydroxyacetate (commercially available) in place of 2-hydroxy-1-morpholinoethanone. $^1$H NMR (CD$_3$OD): δ 7.73 (d, 1H), 7.68 (d, 1H), 7.37 (d, 1H), 7.36-7.32 (m, 3H), 7.07 (s, 1H), 6.84 (d, 1H), 6.67 (d, 1H), 6.21 (d, 1H), 5.50 (s, 2H), 5.16 (s, 2H), 4.72 (s, 2H), 3.90 (s, 3H), 3.76 (s, 2H), 3.51 (t, 2H), 1.52-1.42 (m, 2H), 1.31-1.24 (m, 2H), 1.20-1.11 (m, 2H), 0.87 (t, 3H). LRMS [M+H]=546.3.

Example 19

2-(dipropylcarbamoyl)methyl 2-(4-{[2-amino-4-(pentylamino)-5H-pyrrolo[3,2-d]pyrimidin-5-yl]methyl}-3-methoxyphenyl)acetate

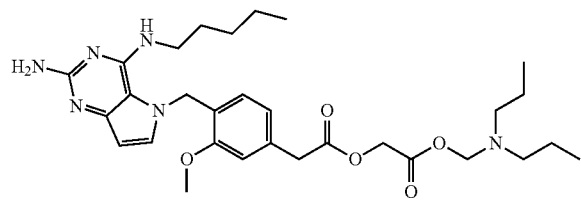 [SMILES: CCCCCNc1nc(N)nc2ccn(Cc3ccc(CC(=O)OCC(=O)OCN(CCC)CCC)cc3OC)c12]

Preparation of 2-(dipropylamino)-2-oxoethyl 2-(4-((2-amino-4-(pentylamino)-5H-pyrrolo[3,2-d]pyrimidin-5-yl)methyl)-3-methoxyphenyl)acetate 2-(Dipropylamino)-2-oxoethyl 2-(4-((2-amino-4-(pentylamino)-5H-pyrrolo[3,2-d]pyrimidin-5-yl)methyl)-3-methoxyphenyl)acetate was prepared from 2-(4-((2-amino-4-(pentylamino)-5H-pyrrolo[3,2-d]pyrimidin-5-yl)methyl)-3-methoxyphenyl)acetic acid (Example 10, Step 4) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6), using 2-hydroxy-N,N-dipropylacetamide (commercially available) in place of 2-hydroxy-1-morpholinoethanone. $^1$H NMR (CD$_3$OD): δ 7.38 (d, 1H), 7.10 (s, 1H), 6.88 (d, 1H), 6.70 (d, 1H), 6.21 (d, 1H), 5.51 (s, 2H), 4.83 (s, 2H), 3.92 (s, 3H), 3.79 (s, 2H), 3.52 (t, 2H), 3.27 (t, 2H), 3.22 (t, 2H), 1.69-1.46 (m, 6H), 1.35-1.25 (m, 2H), 1.20-1.12 (m, 2H), 0.94 (t, 3H)), 0.88 (t, 6H). LRMS [M+H]=539.3.

Example 20

2-(dimethylamino)-2-oxoethyl 2-(4-((2-amino-4-(pentylamino)-5H-pyrrolo[3,2-d]pyrimidin-5-yl)methyl)-3-methoxyphenyl)acetate

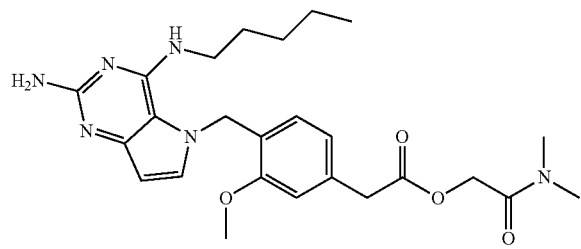 [SMILES: CCCCCNc1nc(N)nc2ccn(Cc3ccc(CC(=O)OCC(=O)N(C)C)cc3OC)c12]

Preparation of 2-(dimethylamino)-2-oxoethyl 2-(4-((2-amino-4-(pentylamino)-5H-pyrrolo[3,2-d]pyrimidin-5-yl)methyl)-3-methoxyphenyl)acetate 2-(Dimethylamino)-2-oxoethyl 2-(4-((2-amino-4-(pentylamino)-5H-pyrrolo[3,2-d]pyrimidin-5-yl)methyl)-3-methoxyphenyl)acetate was prepared from 2-(4-((2-amino-4-(pentylamino)-5H-pyrrolo[3,2-d]pyrimidin-5-yl)methyl)-3-methoxyphenyl)acetic acid (Example 10, Step 4) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6), using 2-hydroxy-N,N-dimethylacetamide (commercially available) in place of 2-hydroxy-1-morpholinoethanone. $^1$H NMR (CD3OD): δ 7.28 (d, 1H), 7.10 (s, 1H), 6.85 (d, 1H), 6.62 (d, 1H), 6.14 (d, 1H), 5.45 (s, 2H), 4.83 (s, 2H), 3.93 (s, 3H), 3.78 (s, 1H), 3.67 (s, 1H), 3.41 (t, 2H), 2.99 (s, 3H), 2.94 (s, 3H), 1.47-1.39 (m, 2H), 1.32-1.23 (m, 2H), 1.19-1.10 (m, 2H), 0.87 (t, 3H). LRMS [M+H]=483.3.

Example 21

2-(4-methylpiperazin-1-yl)ethyl 2-(4-{[2-amino-4-(pentylamino)-5H-pyrrolo[3,2-d]pyrimidin-5-yl]methyl}-3-methoxyphenyl)acetate

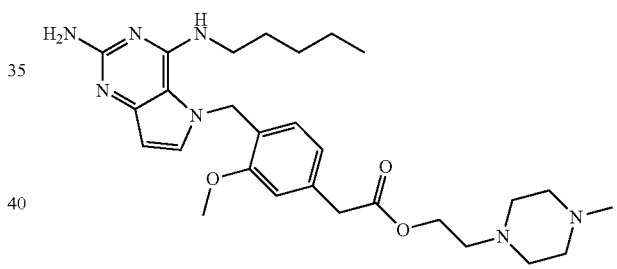

Preparation of 2-(4-methylpiperazin-1-yl)ethyl 2-(4-((2-amino-4-(pentylamino)-5H-pyrrolo[3,2-d]pyrimidin-5-yl)methyl)-3-methoxyphenyl)acetate 2-(4-Methylpiperazin-1-yl)ethyl 2-(4-((2-amino-4-(pentylamino)-5H-pyrrolo[3,2-d]pyrimidin-5-yl)methyl)-3-methoxyphenyl)acetate was prepared from 2-(4-((2-amino-4-(pentylamino)-5H-pyrrolo[3,2-d]pyrimidin-5-yl)methyl)-3-methoxyphenyl)acetic acid (Example 10, Step 4) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6), using 2-(4-methylpiperazin-1-yl)ethanol (commercially available) in place of 2-hydroxy-1-morpholinoethanone. $^1$H NMR (CD$_3$OD): δ 7.31 (d, 1H), 7.02 (s, 1H), 6.84 (d, 1H), 6.65 (d, 1H), 6.19 (d, 1H), 5.45 (s, 2H), 4.21 (t, 2H), 3.92 (s, 3H), 3.66 (s, 2H), 3.45 (t, 2H), 2.61 (t, 2H), 2.55-2.33 (m, 8H), 2.25 (s, 3H), 1.49-1.41 (m, 2H), 1.31-1.24 (m, 2H), 1.18-1.09 (m, 2H), 0.87 (t, 3H). LRMS [M+H]=524.3.

Example 22

2-hydroxyethyl 2-(4-{[2-amino-4-(pentylamino)-5H-pyrrolo[3,2-d]pyrimidin-5-yl]methyl}-3-methoxyphenyl)acetate

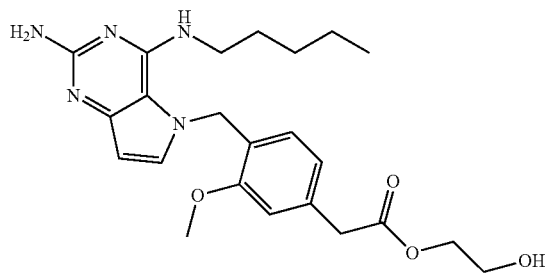 [SMILES: CCCCCNc1nc(N)nc2ccn(Cc3ccc(CC(=O)OCCO)cc3OC)c12]

Preparation of 2-hydroxyethyl 2-(4-((2-amino-4-(pentylamino)-5H-pyrrolo[3,2-d]pyrimidin-5-yl)methyl)-3-methoxyphenyl)acetate 2-Hydroxyethyl 2-(4-((2-amino-4-(pentylamino)-5H-pyrrolo[3,2-d]pyrimidin-5-yl)methyl)-3-methoxyphenyl)acetate was prepared from 2-(4-((2-amino-4-(pentylamino)-5H-pyrrolo[3,2-d]pyrimidin-5-yl)methyl)-3-methoxyphenyl)acetic acid (Example 10, Step 4) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6), using ethane-1,2-diol (commercially available) in place of 2-hydroxy-1-morpholinoethanone. $^1$H NMR (CD$_3$OD) b 7.25 (d, 1H), 7.04 (s, 1H), 6.82 (d, 1H), 6.59 (d, 1H), 6.13 (d, 1H), 5.42 (s, 2H), 4.15 (t, 2H), 3.92 (s, 3H), 3.72 (t, 2H), 3.68 (s, 2H), 3.39 (t, 2H), 1.45-1.38 (m, 2H), 1.30-1.23 (m, 2H), 1.16-1.09 (m, 2H), 0.86 (t, 3H). LRMS [M+H]=442.2.

Example 23

4-(dimethylamino)butyl 2-(4-{[2-amino-4-(pentylamino)-5H-pyrrolo[3,2-d]pyrimidin-5-yl]methyl}-3-methoxyphenyl)acetate

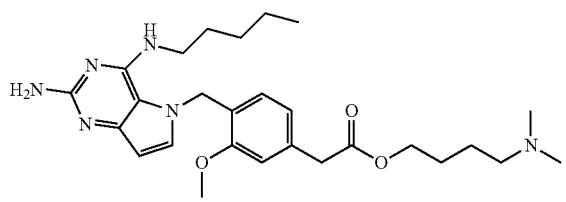 [SMILES: CCCCCNc1nc(N)nc2ccn(Cc3ccc(CC(=O)OCCCCN(C)C)cc3OC)c12]

Preparation of 4-(dimethylamino)butyl 2-(4-((2-amino-4-(pentylamino)-5H-pyrrolo[3,2-d]pyrimidin-5-yl)methyl)-3-methoxyphenyl)acetate 4-(Dimethylamino)butyl 2-(4-((2-amino-4-(pentylamino)-5H-pyrrolo[3,2-d]pyrimidin-5-yl)methyl)-3-methoxyphenyl)acetate was prepared from 2-(4-((2-amino-4-(pentylamino)-5H-pyrrolo[3,2-d]pyrimidin-5-yl)methyl)-3-methoxyphenyl)acetic acid (Example 10, Step 4) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6), using 4-(dimethylamino)butan-1-ol (commercially available) in place of 2-hydroxy-1-morpholinoethanone. $^1$H NMR (CD$_3$OD): δ 7.26 (d, 1H), 7.02 (s, 1H), 6.81 (d, 1H), 6.60 (d, 1H), 6.13 (d, 1H), 5.43 (s, 2H), 4.10 (t, 2H), 3.93 (s, 3H), 3.64 (s, 2H), 3.39 (t, 2H), 2.32 (t, 2H), 2.21 (s, 6H), 1.65-1.59 (m, 2H), 1.53-1.38 (m, 4H), 1.31-1.23 (m, 2H), 1.17-1.11 (m, 2H), 0.87 (t, 3H). LRMS [M+H]=497.3.

Example 24

2-(morpholin-4-yl)ethyl 2-(4-{[2-amino-4-(pentylamino)-5H-pyrrolo[3,2-d]pyrimidin-5-yl]methyl}-3-methoxyphenyl)acetate

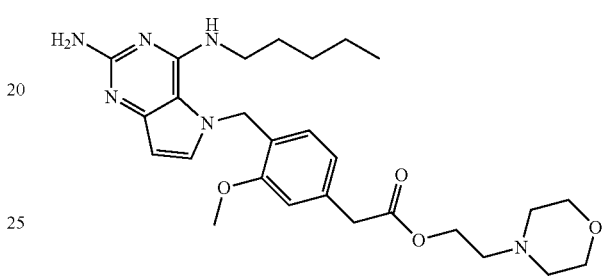

Preparation of 2-morpholinoethyl 2-(4-((2-amino-4-(pentylamino)-5H-pyrrolo[3,2-d]pyrimidin-5-yl)methyl)-3-methoxyphenyl)acetate 2-Morpholinoethyl 2-(4-((2-amino-4-(pentylamino)-5H-pyrrolo[3,2-d]pyrimidin-5-yl)methyl)-3-methoxyphenyl)acetate was prepared from 2-(4-((2-amino-4-(pentylamino)-5H-pyrrolo[3,2-d]pyrimidin-5-yl)methyl)-3-methoxyphenyl)acetic acid (Example 10, Step 4) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6), using 2-morpholinoethanol (commercially available) in place of 2-hydroxy-1-morpholinoethanone. $^1$H NMR (CD$_3$OD): δ 7.34 (d, 1H), 7.04 (s, 1H), 6.85 (d, 1H), 6.68 (d, 1H), 6.20 (d, 1H), 5.48 (s, 2H), 4.23 (t, 2H), 3.92 (s, 3H), 3.67 (s, 2H), 3.59 (t, 4H), 3.49 (t, 2H), 2.60 (t, 2H), 2.42 (t, 4H), 1.52-1.45 (m, 2H), 1.33-1.25 (m, 2H), 1.20-1.12 (m, 2H), 0.88 (t, 3H). LRMS [M+H]=511.3.

Example 25

2-(piperazin-1-yl)ethyl 2-(4-{[2-amino-4-(pentylamino)-5H-pyrrolo[3,2-d]pyrimidin-5-yl]methyl}-3-methoxyphenyl)acetate

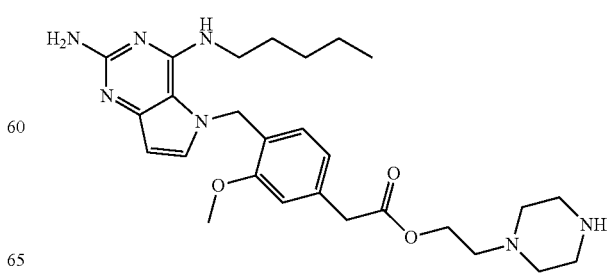

Step 1: Preparation of tert-butyl 4-(2-(2-(4-((2-amino-4-(pentylamino)-5H-pyrrolo[3,2-d]pyrimidin-5-yl)methyl)-3-methoxyphenyl)acetoxy)ethyl)piperazine-1-carboxylate Tert-butyl 4-(2-(2-(4-((2-amino-4-(pentylamino)-5H-pyrrolo[3,2-d]pyrimidin-5-yl)methyl)-3-methoxyphenyl)acetoxy)ethyl)piperazine-1-carboxylate was prepared from 2-(4-((2-amino-4-(pentylamino)-5H-pyrrolo[3,2-d]pyrimidin-5-yl)methyl)-3-methoxyphenyl)acetic acid (Example 10, Step 4) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, step 6), using tert-butyl 4-(2-hydroxyethyl)piperazine-1-carboxylate (commercially available) in place of 2-hydroxy-1-morpholinoethanone.

Step 2: Preparation of 2-(piperazin-1-yl)ethyl 2-(4-((2-amino-4-(pentylamino)-5H-pyrrolo[3,2-d]pyrimidin-5-yl)methyl)-3-methoxyphenyl)acetate Tert-butyl 4-(2-(2-(4-((2-amino-4-(pentylamino)-5H-pyrrolo[3,2-d]pyrimidin-5-yl)methyl)-3-methoxyphenyl)acetoxy)ethyl)piperazine-1-carboxylate (1 equiv., from previous step) was dissolved in DCM (0.033M), and was treated with TFA (40 equiv.) at room temperature for 6 hours. DCM was removed under vacuuo, and the residue was purified with reverse phase preparative HPLC (ACN/water) to afford product as a white powder. $^1$H NMR (CD$_3$OD) b 7.36 (d, 1H), 7.04 (s, 1H), 6.86 (d, 1H), 6.71 (d, 1H), 6.22 (d, 1H), 5.51 (s, 2H), 4.30 (t, 2H), 3.92 (s, 3H), 3.69 (s, 2H), 3.53 (t, 2H), 3.27 (t, 4H), 2.97 (t, 4H), 2.93 (t, 2H), 1.53-1.46 (m, 2H), 1.32-1.25 (m, 2H), 1.19-1.12 (m, 2H), 0.87 (t, 3H). LRMS [M+H]=510.3.

Example 26

2-(dimethylamino)ethyl 2-(3-{[2-amino-4-(pentylamino)-5H-pyrrolo[3,2-d]pyrimidin-5-yl]methyl}-4-methoxyphenoxy)acetate

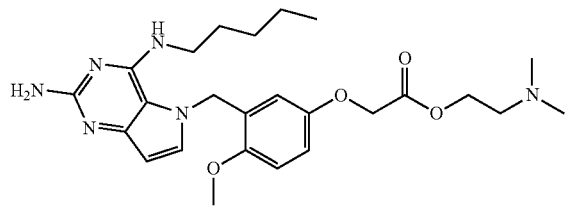 [SMILES: CCCCCNc1nc(N)nc2ccn(Cc3cc(OCC(=O)OCCN(C)C)ccc3OC)c12]

Preparation of 2-(dimethylamino)ethyl 2-(3-((2-amino-4-(pentylamino)-5H-pyrrolo[3,2-d]pyrimidin-5-yl)methyl)-4-methoxyphenoxy)acetate 2-(Dimethylamino)ethyl 2-(3-((2-amino-4-(pentylamino)-5H-pyrrolo[3,2-d]pyrimidin-5-yl)methyl)-4-methoxyphenoxy)acetate was prepared from 2-(3-((2-amino-4-(pentylamino)-5H-pyrrolo[3,2-d]pyrimidin-5-yl)methyl)-4-methoxyphenoxy)acetic acid (Example 8, Step 5) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6), using 2-(dimethylamino)ethanol (commercially available) in place of 2-hydroxy-1-morpholinoethanone. $^1$H NMR (CD$_3$OD): δ 7.36 (d, 1H), 6.99 (d, 1H), 6.88 (d, 1H), 6.35 (s, 1H), 6.18 (d, 1H), 5.46 (s, 2H), 4.23 (s, 2H), 3.86 (s, 3H), 3.75 (t, 2H), 3.49 (t, 2H), 2.88 (t, 2H), 2.60 (s, 6H), 1.51-1.44 (m, 2H), 1.32-1.24 (m, 2H), 1.18-1.10 (m, 2H), 0.87 (t, 3H). LRMS [M+H]=485.3.

Example 27

2-(piperazin-1-yl)ethyl 2-(3-{[2-amino-4-(pentylamino)-5H-pyrrolo[3,2-d]pyrimidin-5-yl]methyl}-4-methoxyphenoxy)acetate

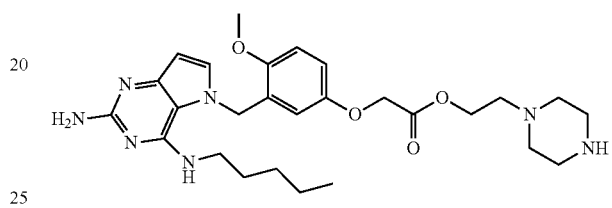

Preparation of 2-(piperazin-1-yl)ethyl 2-(3-((2-amino-4-(pentylamino)-5H-pyrrolo[3,2-d]pyrimidin-5-yl)methyl)-4-methoxyphenoxy)acetate 2-(Piperazin-1-yl)ethyl 2-(3-((2-amino-4-(pentylamino)-5H-pyrrolo[3,2-d]pyrimidin-5-yl)methyl)-4-methoxyphenoxy)acetate was prepared following the same protocol as 2-(piperazin-1-yl)ethyl 2-(4-{[2-amino-4-(pentylamino)-5H-pyrrolo[3,2-d]pyrimidin-5-yl]methyl}-3-methoxyphenyl)acetate (Example 25), using 2-(3-((2-amino-4-(pentylamino)-5H-pyrrolo[3,2-d]pyrimidin-5-yl)methyl)-4-methoxyphenoxy)acetic acid (Example 8, Step 5) in place of 2-(4-((2-amino-4-(pentylamino)-5H-pyrrolo[3,2-d]pyrimidin-5-yl)methyl)-3-methoxyphenyl)acetic acid in step 1. $^1$H NMR (CD$_3$OD): δ 7.40 (d, 1H), 7.02 (d, 1H), 6.90 (d, 1H), 6.28 (s, 1H), 6.25 (d, 1H), 5.50 (s, 2H), 4.57 (s, 2H), 4.31 (t, 2H), 3.88 (s, 3H), 3.53 (t, 2H), 3.25 (t, 4H), 2.88 (t, 4H), 2.85 (t, 2H), 1.53-1.45 (m, 2H), 1.4-1.25 (m, 2H), 1.18-1.10 (m, 2H), 0.87 (t, 3H). LRMS [M+H]=526.3.

Example 28

2-(morpholin-4-yl)ethyl 2-(3-{[2-amino-4-(pentylamino)-5H-pyrrolo[3,2-d]pyrimidin-5-yl]methyl}-4-methoxyphenoxy)acetate

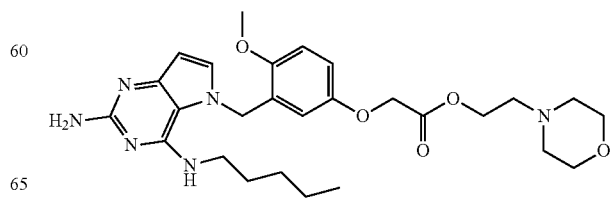

Preparation of 2-morpholinoethyl 2-(3-((2-amino-4-(pentylamino)-5H-pyrrolo[3,2-d]pyrimidin-5-yl)methyl)-4-methoxyphenoxy)acetate 2-Morpholinoethyl 2-(3-((2-amino-4-(pentylamino)-5H-pyrrolo[3,2-d]pyrimidin-5-yl)methyl)-4-methoxyphenoxy)acetate was prepared from 2-(3-((2-amino-4-(pentylamino)-5H-pyrrolo[3,2-d]pyrimidin-5-yl)methyl)-4-methoxyphenoxy)acetic acid (Example 8, Step 5) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6), using 2-morpholinoethanol (commercially available) in place of 2-hydroxy-1-morpholinoethanone. $^1$H NMR (CD$_3$OD): δ 7.40 (d, 1H), 7.03 (d, 1H), 6.92 (d, 1H), 6.32 (s, 1H), 6.24 (d, 1H), 5.52 (s, 2H), 4.64 (s, 2H), 4.51 (t, 2H), 3.95-3.83 (m, 4H), 3.88 (s, 3H), 3.53 (t, 2H), 3.48 (t, 2H), 3.35-3.30 (m, 4H), 1.53-1.46 (m, 2H), 1.32-1.25 (m, 2H), 1.18-1.11 (m, 2H), 0.87 (t, 3H). LRMS [M+H]=527.3.

Example 29

2-(4-methylpiperazin-1-yl)ethyl 2-(3-{[2-amino-4-(pentylamino)-5H-pyrrolo[3,2-d]pyrimidin-5-yl]methyl}-4-methoxyphenoxy)acetate

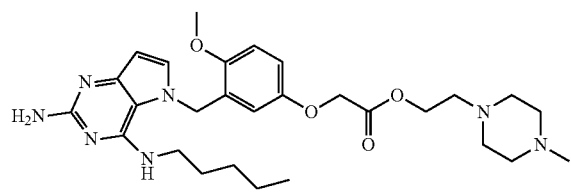 [SMILES: CCCCCNc1nc(N)nc2ccn(Cc3cc(OCC(=O)OCCN4CCN(C)CC4)ccc3OC)c12]

Preparation of 2-(4-methylpiperazin-1-yl)ethyl 2-(3-((2-amino-4-(pentylamino)-5H-pyrrolo[3,2-d]pyrimidin-5-yl)methyl)-4-methoxyphenoxy)acetate 2-(4-Methylpiperazin-1-yl)ethyl 2-(3-((2-amino-4-(pentylamino)-5H-pyrrolo[3,2-d]pyrimidin-5-yl)methyl)-4-methoxyphenoxy)acetate was prepared from 2-(3-((2-amino-4-(pentylamino)-5H-pyrrolo[3,2-d]pyrimidin-5-yl)methyl)-4-methoxyphenoxy)acetic acid (Example 8, Step 5) following the same protocol as 2-morpholino-2-oxoethyl 2-(3-((2-amino-4-(pentylamino)-5H-pyrrolo[3,2-d]pyrimidin-5-yl)methyl)-4-methoxyphenoxy)acetate (Example 8, Step 6), using 2-(4-methylpiperazin-1-yl)ethanol (commercially available) in place of 2-hydroxy-1-morpholinoethanone. $^1$H NMR (CD$_3$OD) b 7.40 (d, 1H), 7.02 (d, 1H), 6.90 (d, 1H), 6.30 (s, 1H), 6.24 (d, 1H), 5.52 (s, 2H), 4.57 (s, 2H), 4.29 (t, 2H), 3.88 (s, 3H), 3.53 (t, 2H), 3.18-3.00 (m, 4H), 2.87 (s, 3H), 2.73 (t, 2H), 2.60-2.35 (m, 4H), 1.53-1.46 (m, 2H), 1.34-1.25 (m, 2H), 1.18-1.10 (m, 2H), 0.87 (t, 3H). LRMS [M+H]=540.3.

Example 30

S)-2-((2-amino-5-(2-methoxy-5-(piperazin-1-ylmethyl)benzyl)-5H-pyrrolo[3,2-d]pyrimidin-4-yl)amino)hexan-1-ol

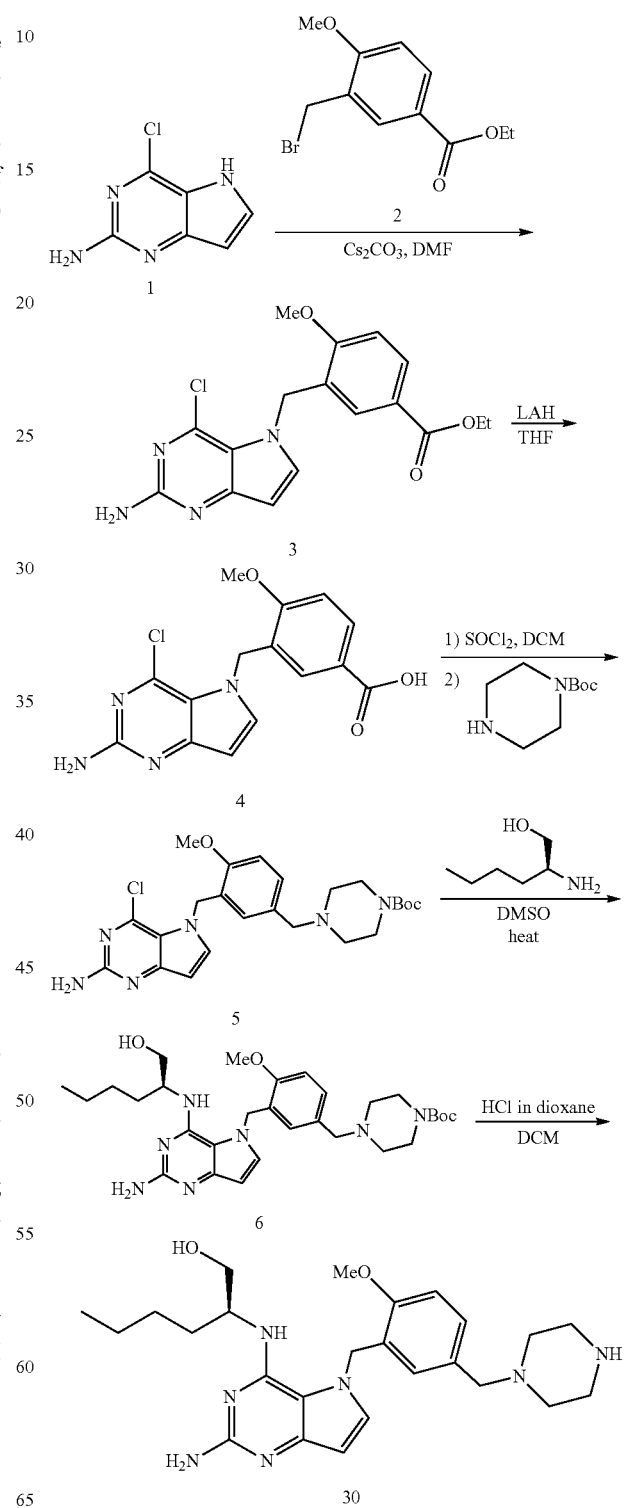

Step 1: Preparation of ethyl 3-((2-amino-4-chloro-5H-pyrrolo[3,2-d]pyrimidin-5-yl)methyl)-4-methoxybenzoate (3)

A round bottom flask was charged with 4-chloro-5H-pyrrolo[3,2-d]pyrimidin-2-amine (1, commercially available, 1 equiv.), ethyl 3-(bromomethyl)-4-methoxybenzoate (2, commercially available, 1 equiv.), caesium carbonate (1 equiv.) and DMF (1 M). The reaction mixture was allowed to stir at room temperature for 18 hours. At this point the solvent was removed in vaccuo. To the resulting mixture was added EtOAc and the solvent was removed in vaccuo. To this mixture was added DCM and the solvent removed in vaccuo. The crude reaction mixture was then purified by ISCO chromatography (0-10% MeOH:DCM, gradient) to afford ethyl 3-((2-amino-4-chloro-5H-pyrrolo[3,2-d]pyrimidin-5-yl)methyl)-4-methoxybenzoate (3) as a solid.

Step 2: (3-((2-amino-4-chloro-5H-pyrrolo[3,2-d]pyrimidin-5-yl)methyl)-4-methoxyphenyl)methanol (4)

A slurry of LAH (1 equiv., powder) in THF (0.3 M) was prepared in a round bottom flask, cooled to 0° C. and vigorously stirred for 15 minutes. To this mixture was added ethyl 3-((2-amino-4-chloro-5H-pyrrolo[3,2-d]pyrimidin-5-yl)methyl)-4-methoxybenzoate (3, 1 equiv. from previous step) in portions. At this point the ice-bath was removed and the reaction mixture was allowed to stir at room temperature for 4 hours (if the reaction was not complete by this time additional LAH was added and stirring continued until the reaction was complete). The reaction mixture was then transferred to an Erlenmeyer flask, transferring with $Et_2O$. The mixture was cooled to 0° C. and vigorously stirred. The reaction was then quenched by the slow addition of ~5 mL of a saturated sodium sulfate solution. A white precipitate was then observed and the mixture was filtered through a frit containing Celite and washed with THF and $Et_2O$. The volatiles were then removed in vacuo and the material used in the next step without further purification.

Step 3: tert-butyl 4-(3-((2-amino-4-chloro-5H-pyrrolo[3,2-d]pyrimidin-5-yl)methyl)-4-methoxybenzyl)piperazine-1-carboxylate (5)

Thionyl chloride (10 equiv.) was added to a round bottom flask containing (3-((2-amino-4-chloro-5H-pyrrolo[3,2-d]pyrimidin-5-yl)methyl)-4-methoxyphenyl)methanol (4, 1 equiv. from previous step) in DCM (0.1 M) at 0° C. The ice-bath was then removed and the reaction mixture allowed to stir at room temperature for 4 hours. The reaction mixture was then cooled back to 0° C. and slowly quenched by the addition of NaOH (1 M, 40 equiv.) and saturated $NaHCO_3$ (aq.). The material was transferred to a separatory funnel and washed with DCM 3×. The combined organic layers were dried with sodium sulfate, filtered and volatiles removed in vacuo. The resulting crude product was then dissolved in DMF (0.1 M) in a round bottom flask and used without further purification. To this material was added tert-butyl piperazine-1-carboxylate (1 equiv.) and Huenig's base (1.2 equiv.) and allowed to stir at room temperature for 18 hours. At this point the reaction mixture was diluted with EtOAc, transferred to a separatory funnel and washed with saturated NaCl (aq.) 2× and water 2×. The combined organic layers were dried with sodium sulfate, filtered and volatiles removed in vacuo. The crude reaction mixture was purified by ISCO chromatography (0-10% MeOH:DCM, gradient) to afford tert-butyl 4-(3-((2-amino-4-chloro-5H-pyrrolo[3,2-d]pyrimidin-5-yl)methyl)-4-methoxybenzyl)piperazine-1-carboxylate (5) as a solid.

Step 4: (S)-tert-butyl 4-(3-((2-amino-4-((1-hydroxyhexan-2-yl)amino)-5H-pyrrolo[3,2-d]pyrimidin-5-yl)methyl)-4-methoxybenzyl)piperazine-1-carboxylate (6)

A round bottom flask was charged with tert-butyl 4-(3-((2-amino-4-chloro-5H-pyrrolo[3,2-d]pyrimidin-5-yl)methyl)-4-methoxybenzyl)piperazine-1-carboxylate (5, 1 equiv. from previous step), commercially available (S)-2-aminohexan-1-ol (3 equiv.), Huenig's base (5 equiv.) and DMSO (0.5 M). The reaction mixture was heated to 120° C. and allowed to stir for 18 hours. At this point the reaction mixture was allowed to cool to room temperature and water added. This mixture was then frozen and the majority of volatiles removed by lyophilization. The crude reaction mixture was purified by ISCO chromatography (0-10% MeOH (the MeOH contained 0.7 N $NH_3$):DCM, gradient) to afford (S)-tert-butyl 4-(3-((2-amino-4-((1-hydroxyhexan-2-yl)amino)-5H-pyrrolo[3,2-d]pyrimidin-5-yl)methyl)-4-methoxybenzyl)piperazine-1-carboxylate (6) as a solid.

Step 5: Example 1-(S)-2-((2-amino-5-(2-methoxy-5-(piperazin-1-ylmethyl)benzyl)-5H-pyrrolo[3,2-d]pyrimidin-4-yl)amino)hexan-1-ol (30)

HCl in dioxane (4 M, 20 equiv.) was added to a solution of (S)-tert-butyl 4-(3-((2-amino-4-((1-hydroxyhexan-2-yl)amino)-5H-pyrrolo[3,2-d]pyrimidin-5-yl)methyl)-4-methoxybenzyl)piperazine-1-carboxylate (6, 1 equiv. from previous step) in DCM (0.1 M) in a round bottom flask at 0° C. The ice-bath was then removed and the reaction mixture was stirred at room temperature for 3 hours. At this point $NH_3$ in MeOH (0.7 N) was added to the reaction mixture and the volatiles removed in vacuo. The addition of $NH_3$ in MeOH (0.7 N) and removal of volatiles in vacuo was repeated two more times. The crude reaction mixture was then purified by ISCO chromatography (0-20% MeOH (the MeOH contained 0.7 N $NH_3$):DCM, gradient) to provide (S)-2-((2-amino-5-(2-methoxy-5-(piperazin-1-ylmethyl)benzyl)-5H-pyrrolo[3,2-d]pyrimidin-4-yl)amino)hexan-1-ol (30) as a solid: $^1$H NMR ($CD_3OD$): δ 7.50 (d, 1H), 7.29 (d, 1H), 7.09 (d, 1H), 6.54 (s, 1H), 6.29 (d, 1H), 5.69 (d, 1H), 5.40 (d, 1H), 4.37-4.31 (m, 1H), 3.95 (s, 3H), 3.52-3.49 (m, 2H), 3.42 (s, 2H), 3.1-2.3 (m, 8H), 1.52-1.16 (m, 4H), 1.05-0.88 (m, 2H), 0.83 (s, 3H). LRMS [M+H]=468.3.

Example 31

5-(2-methoxy-5-(piperazin-1-ylmeth yl)benzyl)-N4-pentyl-5H-pyrrolo[3,2-d]pyrimidine-2,4-diamine

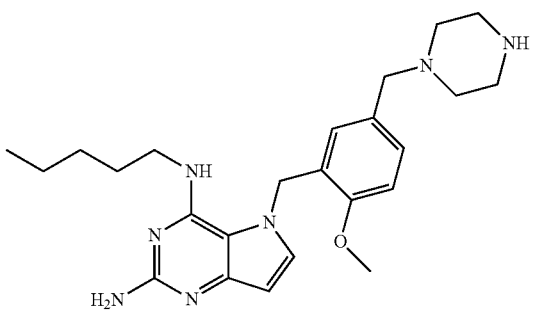 [SMILES: CCCCCNc1nc(N)nc2ccn(Cc3cc(CN4CCNCC4)ccc3OC)c12]

5-(2-methoxy-5-(piperazin-1-ylmethyl)benzyl)-N4-pentyl-5H-pyrrolo[3,2-d]pyrimidine-2,4-diamine was prepared according to the scheme shown for Example 30. Commercially available N-pentylamine was used in place of (S)-2-aminohexan-1-ol in Step 4. ¹H NMR (CD₃OD): δ 7.42 (d, 1H), 7.32 (d, 1H), 7.09 (d, 1H), 6.70 (s, 1H), 6.25 (d, 1H), 5.54 (s, 2H), 3.92 (s, 3H), 3.52 (t, 2H), 3.46 (s, 2H), 3.18-3.10 (m, 4H), 2.63-2.58 (m, 4H), 1.53-1.44 (m, 2H), 1.37-1.24 (m, 2H), 1.17-1.09 (m, 2H), 0.88 (t, 3H). LRMS [M+H]=438.3.

Example 32

5-(2-methoxy-4-(piperazin-1-ylmethyl)benzyl)-N4-pentyl-5H-pyrrolo[3,2-d]pyrimidine-2,4-diamine

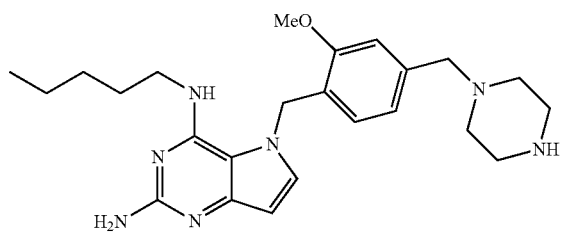 [SMILES: CCCCCNc1nc(N)nc2ccn(Cc3ccc(CN4CCNCC4)cc3OC)c12]

5-(2-methoxy-4-(piperazin-1-ylmethyl)benzyl)-N4-pentyl-5H-pyrrolo[3,2-d]pyrimidine-2,4-diamine was prepared according to the scheme shown for Example 30. Commercially available methyl 4-(bromomethyl)-3-methoxybenzoate was used in place of ethyl 3-(bromomethyl)-4-methoxybenzoate in Step 1, and commercially available N-pentylamine was used in place of (S)-2-aminohexan-1-ol in Step 4. ¹H NMR (CD3OD): δ 7.37 (d, 1H), 7.11 (s, 1H), 6.92 (d, 1H) 6.75 (d, 1H), 6.22 (d, 1H), 5.53 (s, 2H), 3.93 (s, 3H) 3.61 (s, 2H), 3.55 (t, 2H), 3.24-3.22 (m, 4H), 2.69-2.68 (m, 4H), 1.57-1.48 (m, 2H), 1.35-1.26 (m, 2H), 1.21-1.14 (m, 2H), 0.89 (s, 3H). LRMS [M+H]=438.3.

Example 33

(S)-2-((2-amino-5-(2-methoxy-4-(piperazin-1-ylmethyl)benzyl)-5H-pyrrolo[3,2-d]pyrimidin-4-yl)amino)hexan-1-ol

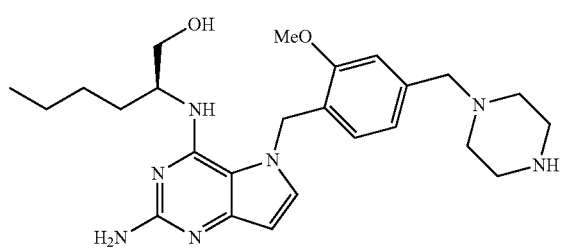 [SMILES: CCCC[C@@H](CO)Nc1nc(N)nc2ccn(Cc3ccc(CN4CCNCC4)cc3OC)c12]

(S)-2-((2-amino-5-(2-methoxy-4-(piperazin-1-ylmethyl)benzyl)-5H-pyrrolo[3,2-d]pyrimidin-4-yl)amino)hexan-1-ol was prepared according to the scheme shown for Example 30. Commercially available methyl 4-(bromomethyl)-3-methoxybenzoate was used in place of ethyl 3-(bromomethyl)-4-methoxybenzoate in Step 1. ¹H NMR (CD₃OD): δ 7.49 (d, 1H), 7.00 (s, 1H), 6.68 (d, 1H), 6.27 (d, 1H), 6.00 (d, 1H), 5.64 (d, 1H), 5.48 (d, 1H), 4.42-4.35 (m, 1H), 3.96 (s, 3H), 3.55-3.49 (m, 2H), 3.45-3.35 (m, 2H), 3.25-2.80 (m, 8H), 1.56-1.18 (m, 4H), 1.12-1.00 (m, 2H), 0.85 (t, 3H). LRMS [M+H]=468.4.

Example 34

5-(5-amino-2-methoxybenzyl)-N4-pentyl-5H-pyrrolo[3,2-d]pyrimidine-2,4-diamine

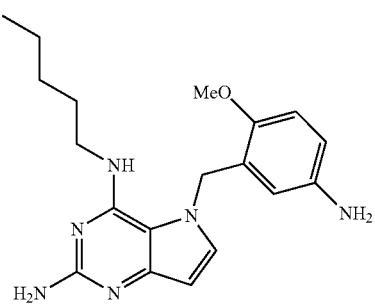

Step 1: Preparation of 5-(2-methoxy-5-nitrobenzyl)-N4-pentyl-5H-pyrrolo[3,2-d]pyrimidine-2,4-diamine

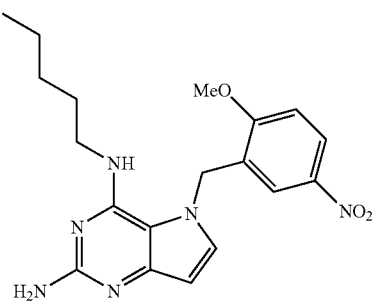 [SMILES: CCCCCNc1nc(N)nc2ccn(Cc3cc([N+](=O)[O-])ccc3OC)c12]

5-(2-methoxy-5-nitrobenzyl)-N4-pentyl-5H-pyrrolo[3,2-d]pyrimidine-2,4-diamine was prepared following the procedure described in step 1 of Example 1, by using 2-(bromomethyl)-1-methoxy-4-nitrobenzene (commercially available) in place of methyl 3-methoxy-4-methylbenzoate.

Step 2: Preparation of 5-(5-amino-2-methoxybenzyl)-N4-pentyl-5H-pyrrolo[3,2-d]pyrimidine-2,4-diamine 5-(2-Methoxy-5-nitrobenzyl)-N4-pentyl-5H-pyrrolo[3,2-d]pyrimidine-2,4-diamine (1 eq.) from step 1 was dissolved in ethanol (0.1 M). Pd on carbon (10% by weight, wet) (0.1 eq.) was added. The reaction was stirred under H₂ atmosphere for 2 hrs. After filtering off solids and removal of volatiles by rotavap, the residue was purified by silica gel chromatography (ISCO, 0-10% methanol in DCM) to afford 5-(5-amino-2-methoxybenzyl)-N4-pentyl-5H-pyrrolo[3,2-d]pyrimidine-2,4-diamine as colorless oil. 1H NMR (CDCl3): δ 7.06 (d, 1H), 6.79 (d, 1H), 6.62 (dd, 1H), 6.25 (d, 1H), 6.05 (d, 1H), 5.27 (s, 2H), 3.86 (s, 3H), 3.33 (m, 2H), 1.38-1.24 (m, 4H), 1.15-1.09 (m, 2H), 0.87 (t, 3H). LRMS[M+1]=355.2.

Assays

Compounds of Formula (I) were assayed to measure their capacity as toll-like receptor 7 agonists.

Human Peripheral Blood Mononuclear Cell Assay

The bioactivity of the compounds of Formula (I) were tested in the human peripheral blood assay (human PBMC) using a panel of independent normal human donors according to approved guidelines by the institutional review committee. Human PBMC were isolated from freshly peripheral blood using a Ficoll density gradient (GE healthcare 17-1440-03). 30-35 mLs of peripheral human blood were layered onto 15 mLs of Ficoll in 50 ml conical tubes, followed by centrifugation at 1800 rpm (Eppendorf Centrifuge 5810R with biohazard caps over the tube buckets) at room temperature for 30 minutes with no acceleration and no brake. The buffy layers were then collected and transferred onto new 50 ml conical tubes and washed twice in complete media consisting of RPMI 1640 (11875085 from Invitrogen Corporation, Carlsbad, Calif.) supplemented with 10% heat inactivated fetal bovine serum (Gibco 10099-141), 1% Pen-Strep (Gibco #15140-122), 1 mM non essential amino acids (Gibco #11140-050), 1 mM sodium pyruvate (Gibco #11360-070), 2 mM L-Glutamine (Gibco #25030-081) and 1 mM HEPES (Gibco #15630-080). Viable cells were then counted using trypan blue staining, plated in 96 well flat bottom plates (Becton Dickinson #353070) at $2\times10^5$ cells per well in 200 □l total volume of complete media. Compounds were then added in a 10 point dose response format starting at 100 µM, 3 fold dilution. Negative controls wells received equal concentration of DMSO. Culture supernatants were collected after 18-24 hours incubation at 37° C., 5% $CO_2$, stored at −20° C. until further use.

IL-6 levels in the culture supernatants were measured using a Luminex kit (Biorad). Data analysis is performed using Prism software from GraphPad (San Diego, Calif.). Dose response curves are generated for each compound and $EC_{50}$ values were determined as the concentration that gives 50% of the maximal signal.

Reporter gene assay Human embryonic kidney 293 (HEK 293) cells were stably transfected with human TLR7 and an NF-kB-driven luciferase reporter vector (pNifty-Luciferase). As a control assay, normal Hek293 transfected with pNifty-Luc were used. Cells were cultured in DMEM supplemented with 2 mM L-glutamine, 10% heart inactivated FBS, 1% penicillin and streptomycin, 2 µg/ml puromycin (InvivoGen # ant-pr-5) and 5 µg/ml of blasticidin (Invitrogen #46-1120). Bright-Glo™ Luciferase assay buffer and substrate were supplied by Promega # E263B and # E264B (assay substrate and buffer respectively). 384 well clear-bottom plates were supplied by Greiner bio-one (#789163-G) and were custom bar-coded plates.

Cells were plated at 25,000 cells/well in 384-well plates in a final volume of 50 µl of media. Cells were allowed to adhere to the plates after overnight (18 hours) culture at 37° C. and 5% $CO_2$. Serially diluted experimental and positive control compounds were then dispensed to each well and incubated for 7 hours at 37° C. and 5% $CO_2$. Cells stimulated with DMSO alone also serve as negative controls. After the incubation, 30 µl of the pre-mix assay buffer and substrate buffer were added to each well according to manufacturer's instructions. The luminescence signal was read on a CLIPR machine with an integration time of 20 seconds per plate.

Dose response curves are generated for each compound and $EC_{50}$ values were determined as the concentration that gives 50% of the maximal signal.

Certain Assay Results

Various compounds of Formula (I) in free form or in pharmaceutically acceptable salt form, exhibit pharmacological properties, for example, as indicated by the in vitro tests described in this application. The $EC_{50}$ value in those experiments is given as that concentration of the test compound in question that provoke a response halfway between the baseline and maximum responses. In other examples, compounds of Formula (I) have $EC_{50}$ values in the range from 1 nM to 2 µM. In other examples, compounds of Formula (I) have $EC_{50}$ values in the range from 1 nM to 1 µM. In other examples, compounds of Formula (I) have $EC_{50}$ values in the range from 1 nM to 500 nM. In other examples, compounds of Formula (I) have $EC_{50}$ values in the range from 1 nM to 250 nM. In other examples, compounds of Formula (I) have $EC_{50}$ values in the range from 1 nM to 100 nM. In other examples, compounds of Formula (I) have $EC_{50}$ values in the range from 1 nM to 50 nM. In other examples, compounds of Formula (I) have $EC_{50}$ values in the range from 1 nM to 25 nM. In other examples, compounds of Formula (I) have $EC_{50}$ values in the range from 1 nM to 10 nM. Such $EC_{50}$ values are obtained relative to the activity of resiquimod set to 100%.

By way of example only, the $EC_{50}$ for TLR-7 stimulation by certain compounds of Formula (I) are listed in Table 1.

TABLE 1

| Example Number | Human TLR7 $EC_{50}$ (µM) HEK293 |
|---|---|
| 1 | 0.01 |
| 2 | <0.005 |
| 3 | 0.02 |
| 4 | <0.005 |
| 5 | 0.01 |
| 6 | 0.03 |
| 7 | 0.1 |
| 8 | 0.04 |
| 9 | 0.01 |
| 10 | 0.006 |
| 11 | 0.02 |
| 12 | 0.03 |
| 13 | 0.01 |
| 14 | 0.01 |
| 15 | 0.02 |
| 16 | <0.005 |
| 17 | 0.05 |
| 18 | 0.2 |
| 19 | 0.2 |
| 20 | 0.08 |
| 21 | <0.005 |
| 22 | <0.006 |
| 23 | 0.007 |
| 24 | 0.008 |
| 25 | 0.03 |
| 26 | 0.3 |
| 27 | 0.5 |
| 28 | 0.4 |
| 29 | 0.2 |
| 30 | 0.08 |
| 31 | 0.02 |
| 32 | <0.005 |
| 33 | 0.007 |
| 34 | 0.001 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A pharmaceutical composition comprising a therapeutically effective amount of a compound of compound of Formula (I), or pharmaceutically acceptable salt thereof, a pharmaceutically acceptable carrier and one or more additional therapeutic agents:

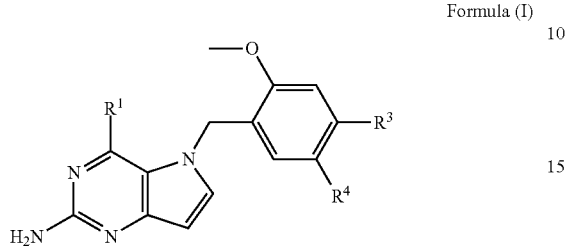

Formula (I)

wherein:
$R^1$ is —$NHR^6$ or —$NHCHR^6R^9$;
$R^3$ is -$L_2$C(=O)$OR^7$, —C(=O)$OL_6R^{12}$, —C(=O)$OL_2R^{12}$, -$L_2$C(=O)$OL_2R^{12}$, -$L_4$C(=O)$OL_5$OH, -$L_4R^{12}$, -$L_2$C(=O)$OL_4$C(=O)$L_2R^{12}$, -$L_2$C(=O)$OL_6R^{12}$, -$L_2$C(=O)$OL_4$C(=O)$OL_2R^{12}$, -$L_2$C(=O)$OL_4$C(=O)$R^{12}$, -$L_4$C(=O)$OL_2$C(=O)$R^{12}$, —$CF_2$C(=O)$R^7$, —CH=CHC(=O)$OL_4$C(=O)$R^{12}$, —$OL_2$C(=O)$OL_4$C(=O)$R^{12}$, —$OL_4$C(=O)$OL_2R^{12}$, —$OL_4$C(=O)$OL_2$C(=O)$R^{12}$ or -$L_2$C(=O)$OL_3R^{12}$;
$R^4$ is -$L_2$C(=O)$OR^7$, —C(=O)$OL_6R^{12}$, —C(=O)$OL_2R^{12}$, -$L_2$C(=O)$OL_2R^{12}$, -$L_4$C(=O)$OL_5$OH, -$L_4R^{12}$, -$L_2$C(=O)$OL_4$C(=O)$L_2R^{12}$, -$L_2$C(=O)$OL_6R^{12}$, -$L_2$C(=O)$OL_4$C(=O)$OL_2R^{12}$, -$L_2$C(=O)$OL_4$C(=O)$R^{12}$, -$L_4$C(=O)$OL_2$C(=O)$R^{12}$, —$CF_2$C(=O)$R^7$, —CH=CHC(=O)$OL_4$C(=O)$R^{12}$, —$OL_2$C(=O)$OL_4$C(=O)$R^{12}$, —$OL_4$C(=O)$OL_2R^{12}$, —$OL_4$C(=O)$OL_2$C(=O)$R^{12}$ or -$L_2$C(=O)$OL_3R^{12}$;
or $R^4$ is H, and $R^3$ is -$L_2$C(=O)$OR^7$, —C(=O)$OL_6R^{12}$, —C(=O)$OL_2R^{12}$, -$L_2$C(=O)$OL_2R^{12}$, -$L_4$C(=O)$OL_5$OH, -$L_4R^{12}$, -$L_2$C(=O)$OL_4$C(=O)$L_2R^{12}$, -$L_2$C(=O)$OL_6R^{12}$, -$L_2$C(=O)$OL_4$C(=O)$OL_2R^{12}$, -$L_2$C(=O)$OL_4$C(=O)$R^{12}$, -$L_4$C(=O)$OL_2$C(=O)$R^{12}$, —$CF_2$C(=O)$R^7$, —$CF_2$C(=O)$OR^7$, —N($R^{11}$)$_2$, —CH=CHC(=O)$OL_4$C(=O)$R^{12}$, —$OL_2$C(=O)$OL_4$C(=O)$R^{12}$, —$OL_4$C(=O)$OL_2R^{12}$, —$OL_4$C(=O)$OL_2$C(=O)$R^{12}$ or -$L_2$C(=O)$OL_3R^{12}$;
or $R^3$ is H, and $R^4$ is -$L_2$C(=O)$OR^7$, —C(=O)$OL_6R^{12}$, —C(=O)$OL_2R^{12}$, -$L_2$C(=O)$OL_2R^{12}$, -$L_4$C(=O)$OL_5$OH, -$L_4R^{12}$, -$L_2$C(=O)$OL_4$C(=O)$L_2R^{12}$, -$L_2$C(=O)$OL_6R^{12}$, -$L_2$C(=O)$OL_4$C(=O)$OL_2R^{12}$, -$L_2$C(=O)$OL_4$C(=O)$R^{12}$, -$L_4$C(=O)$OL_2$C(=O)$R^{12}$, —$CF_2$C(=O)$R^7$, —$CF_2$C(=O)$OR^7$, —N($R^{11}$)$_2$, —CH=CHC(=O)$OL_4$C(=O)$R^{12}$, —$OL_2$C(=O)$OL_4$C(=O)$R^{12}$, —$OL_4$C(=O)$OL_2R^{12}$, —$OL_4$C(=O)$OL_2$C(=O)$R^{12}$ or -$L_2$C(=O)$OL_3R^{12}$;
$L_1$ is —$(CH_2)_m$—;
$L_2$ is —$(CH_2)_m$—;
$L_3$ is —$(CH_2)_m$—;
$L_4$ is —$(CH_2)_m$—;
$L_5$ is —$(CH_2)_m$—;
$L_6$ is —$(CH_2)_mO(CH_2)_m$—;
$R^6$ is —$C_4$-$C_6$alkyl;
$R^7$ is —$C_1$-$C_3$alkyl;
$R^9$ is $L_1$OH;
each $R^{11}$ is independently selected from H or —$C_1$-$C_3$alkyl;
$R^{12}$ is
a) —N($R^{11}$)$_2$;
b) an unsubstituted 5-6 membered heterocycloalkyl having 1 to 2 heteroatoms independently selected from N and O;
c) a 5-6 membered heterocycloalkyl having 1 to 2 heteroatoms independently selected from N and O substituted with =O;
d) a 5-6 membered heterocycloalkyl having 1 to 2 heteroatoms independently selected from N and O substituted with $C_1$-$C_3$alkyl or —C(=O)$OR^7$;
or
e) an unsubstituted phenyl;
and
each m is independently selected from 1, 2, 3, and 4.

2. The pharmaceutical composition of claim 1, wherein:
$R^1$ —$NHR^6$ or —$NHCHR^6R^9$;
$R^3$ is -$L_2$C(=O)$OR^7$, —C(=O)$OL_6R^{12}$, —C(=O)$OL_2R^{12}$, -$L_2$C(=O)$OL_2R^{12}$, -$L_4$C(=O)$OL_5$OH, -$L_4R^{12}$, -$L_2$C(=O)$OL_4$C(=O)$L_2R^{12}$, -$L_2$C(=O)$OL_6R^{12}$, -$L_2$C(=O)$OL_4$C(=O)$OL_2R^{12}$, -$L_2$C(=O)$OL_4$C(=O)$R^{12}$, -$L_4$C(=O)$OL_2$C(=O)$R^{12}$, —$CF_2$C(=O)$R^7$, —CH=CHC(=O)$OL_4$C(=O)$R^{12}$, —$OL_2$C(=O)$OL_4$C(=O)$R^{12}$, —$OL_4$C(=O)$OL_2R^{12}$, —$OL_4$C(=O)$OL_2$C(=O)$R^{12}$ or -$L_2$C(=O)$OL_3R^{12}$;
$R^4$ is -$L_2$C(=O)$OR^7$, —C(=O)$OL_6R^{12}$, —C(=O)$OL_2R^{12}$, -$L_2$C(=O)$OL_2R^{12}$, -$L_4$C(=O)$OL_5$OH, -$L_4R^{12}$, -$L_2$C(=O)$OL_4$C(=O)$L_2R^{12}$, -$L_2$C(=O)$OL_6R^{12}$, -$L_2$C(=O)$OL_4$C(=O)$OL_2R^{12}$, -$L_2$C(=O)$OL_4$C(=O)$R^{12}$, -$L_4$C(=O)$OL_2$C(=O)$R^{12}$, —$CF_2$C(=O)$R^7$, —CH=CHC(=O)$OL_4$C(=O)$R^{12}$, —$OL_2$C(=O)$OL_4$C(=O)$R^{12}$, —$OL_4$C(=O)$OL_2R^{12}$, —$OL_4$C(=O)$OL_2$C(=O)$R^{12}$ or -$L_2$C(=O)$OL_3R^{12}$;
or $R^4$ is H, and $R^3$ is -$L_2$C(=O)$OR^7$, —C(=O)$OL_6R^{12}$, —C(=O)$OL_2R^{12}$, -$L_2$C(=O)$OL_2R^{12}$, -$L_4$C(=O)$OL_5$OH, -$L_4R^{12}$, -$L_2$C(=O)$OL_4$C(=O)$L_2R^{12}$, -$L_2$C(=O)$OL_6R^{12}$, -$L_2$C(=O)$OL_4$C(=O)$OL_2R^{12}$, -$L_2$C(=O)$OL_4$C(=O)$R^{12}$, -$L_4$C(=O)$OL_2$C(=O)$R^{12}$, —$CF_2$C(=O)$R^7$, —CH=CHC(=O)$OL_4$C(=O)$R^{12}$, —$OL_2$C(=O)$OL_4$C(=O)$R^{12}$, —$OL_4$C(=O)$OL_2R^{12}$, —$OL_4$C(=O)$OL_2$C(=O)$R^{12}$ or -$L_2$C(=O)$OL_3R^{12}$;
or $R^3$ is H, and $R^4$ is -$L_2$C(=O)$OR^7$, —C(=O)$OL_6R^{12}$, —C(=O)$OL_2R^{12}$, -$L_2$C(=O)$OL_2R^{12}$, -$L_4$C(=O)$OL_5$OH, -$L_4R^{12}$, -$L_2$C(=O)$OL_4$C(=O)$L_2R^{12}$, -$L_2$C(=O)$OL_6R^{12}$, -$L_2$C(=O)$OL_4$C(=O)$OL_2R^{12}$, -$L_2$C(=O)$OL_4$C(=O)$R^{12}$, -$L_4$C(=O)$OL_2$C(=O)$R^{12}$, —$CF_2$C(=O)$R^7$, —CH=CHC(=O)$OL_4$C(=O)$R^{12}$, —$OL_2$C(=O)$OL_4$C(=O)$R^{12}$, —$OL_4$C(=O)$OL_2R^{12}$, —$OL_4$C(=O)$OL_2$C(=O)$R^{12}$ or -$L_2$C(=O)$OL_3R^{12}$;
$L_1$ is —$(CH_2)_m$—;
$L_2$ is —$(CH_2)_m$—;
$L_3$ is —$(CH_2)_m$—;
$L_4$ is —$(CH_2)_m$—;
$L_5$ is —$(CH_2)_m$—;
$L_6$ is —$(CH_2)_mO(CH_2)_m$—;
$R^6$ is —$C_4$-$C_6$alkyl;
$R^7$ is —$C_1$-$C_3$alkyl;
$R^9$ is $L_1$OH;
each $R^{11}$ is independently selected from H or —$C_1$-$C_3$alkyl;

$R^{12}$ is
a) —N($R^{11}$)$_2$;
b) an unsubstituted 5-6 membered heterocycloalkyl having 1 to 2 heteroatoms independently selected from N and O;
c) a 5-6 membered heterocycloalkyl having 1 to 2 heteroatoms independently selected from N and O substituted with =O;
d) a 5-6 membered heterocycloalkyl having 1 to 2 heteroatoms independently selected from N and O substituted with $C_1$-$C_3$alkyl or —C(=O)O$R^7$;
or
e) an unsubstituted phenyl;
and
each m is independently selected from 1, 2, 3, and 4.

3. The pharmaceutical composition of claim 1, wherein the compound of Formula (I) is a compound of Formula (Ia) or Formula (Ib):

Formula (Ia)

<chemical structure>

Formula (Ib)

<chemical structure>

4. The pharmaceutical composition of claim 1, wherein, $R^1$ is —NH$R^6$ or —NHCH$R^6R^9$;
$R^3$ is -$L_2$C(=O)O$R^7$, —C(=O)O$L_6R^{12}$, —C(=O)O$L_2R^{12}$, -$L_2$C(=O)O$L_2R^{12}$, -$L_4$C(=O)O$L_5$OH, -$L_4R^{12}$, -$L_2$C(=O)O$L_4$C(=O)$L_2R^{12}$, -$L_2$C(=O)O$L_6R^{12}$, -$L_2$C(=O)O$L_4$C(=O)O$L_2R^{12}$, -$L_2$C(=O)O$L_4$C(=O)$R^{12}$, -$L_4$C(=O)O$L_2$C(=O)$R^{12}$ or -$L_2$C(=O)O$L_3R^{12}$;
$R^4$ is —CF$_2$C(=O)$R^7$, -$L_4R^{12}$, —CH=CHC(=O)O$L_4$C(=O)$R^{12}$, —O$L_2$C(=O)O$L_4$C(=O)O$L_4$C(=O)$R^{12}$, —O$L_4$C(=O)O$L_2R^{12}$, -$L_2$C(=O)O$R^7$, -$L_2$C(=O)O$L_4$C(=O)$R^{12}$, —O$L_4$C(=O)O$L_2$C(=O)$R^{12}$ or -$L_2$C(=O)O$L_3R^{12}$;
or $R^4$ is H, and $R^3$ is -$L_2$C(=O)O$R^7$, —C(=O)O$L_6R^{12}$, —C(=O)O$L_2R^{12}$, -$L_2$C(=O)O$L_2R^{12}$, -$L_4$C(=O)O$L_5$OH, -$L_4R^{12}$, -$L_2$C(=O)O$L_4$C(=O)$L_2R^{12}$, -$L_2$C(=O)O$L_6R^{12}$, -$L_2$C(=O)O$L_4$C(=O)O$L_2R^{12}$, -$L_2$C(=O)O$L_4$C(=O)$R^{12}$, -$L_4$C(=O)O$L_2$C(=O)$R^{12}$ or -$L_2$C(=O)O$L_3R^{12}$;
or $R^3$ is H, and $R^4$ is —CF$_2$C(=O)$R^7$, -$L_4R^{12}$, —CH=CHC(=O)O$L_4$C(=O)$R^{12}$, —O$L_2$C(=O)O$L_4$C(=O)O$L_4$C(=O)$R^{12}$, —O$L_4$C(=O)O$L_2R^{12}$, -$L_2$C(=O)O$R^7$, -$L_2$C(=O)O$L_4$C(=O)$R^{12}$, —O$L_4$C(=O)O$L_2$C(=O)$R^{12}$ or -$L_2$C(=O)O$L_3R^{12}$;
$L_1$ is —CH$_2$—;
$L_2$ is —CH$_2$— or —CH$_2$CH$_2$—;
$L_3$ is —CH$_2$CH$_2$— or —CH$_2$CH$_2$CH$_2$CH$_2$—;
$L_4$ is —CH$_2$—,
$L_5$ is —CH$_2$CH$_2$—,
$L_6$ is —(CH$_2$)$_2$O(CH$_2$)$_2$—;
$R^6$ is —C$_4$alkyl or —C$_5$alkyl;
$R^7$ is methyl, ethyl or propyl;
$R^9$ is $L_1$OH;
each $R^{11}$ is independently selected from —$C_1$-$C_3$alkyl;
and
$R^{12}$ is
a) —N($R^{11}$)$_2$;
b) an unsubstituted piperazinyl or an unsubstituted morpholinyl;
c) a 5-6 membered heterocycloalkyl having 1 to 2 heteroatoms independently selected from N and O substituted with =O;
d) a piperazinyl substituted with $C_1$-$C_3$alkyl or —C(=O)O$R^7$;
or
e) an unsubstituted phenyl.

5. The pharmaceutical composition of claim 1, wherein, $R^1$ is —NH$R^6$ or —NHCH$R^6R^9$;
$R^4$ is H, and $R^3$ is -$L_2$C(=O)O$R^7$, —C(=O)O$L_6R^{12}$, —C(=O)O$L_2R^{12}$, -$L_2$C(=O)O$L_2R^{12}$, -$L_4$C(=O)O$L_5$OH, -$L_4R^{12}$, -$L_2$C(=O)O$L_4$C(=O)$L_2R^{12}$, -$L_2$C(=O)O$L_6R^{12}$, -$L_2$C(=O)O$L_4$C(=O)O$L_2R^{12}$, -$L_2$C(=O)O$L_4$C(=O)$R^{12}$, -$L_4$C(=O)O$L_2$C(=O)$R^{12}$, —CF$_2$C(=O)O$R^7$, —N($R^{11}$)$_2$ or -$L_2$C(=O)O$L_3R^{12}$;
or $R^3$ is H, and $R^4$ is —CF$_2$C(=O)$R^7$, -$L_4R^{12}$, —CH=CHC(=O)O$L_4$C(=O)$R^{12}$, —O$L_2$C(=O)O$L_4$C(=O)$R^{12}$, —O$L_4$C(=O)O$L_2R^{12}$, -$L_2$C(=O)O$R^7$, -$L_2$C(=O)O$L_4$C(=O)$R^{12}$, —O$L_4$C(=O)O$L_2$C(=O)$R^{12}$, —CF$_2$C(=O)O$R^7$, —N($R^{11}$)$_2$ or -$L_2$C(=O)O$L_3R^{12}$;
$L_1$ is —CH$_2$—;
$L_2$ is —CH$_2$— or —CH$_2$CH$_2$—;
$L_3$ is —CH$_2$CH$_2$— or —CH$_2$CH$_2$CH$_2$CH$_2$—;
$L_4$ is —CH$_2$—,
$L_5$ is —CH$_2$CH$_2$—,
$L_6$ is —(CH$_2$)$_2$O(CH$_2$)$_2$—;
$R^6$ is —C$_4$alkyl or —C$_5$alkyl;
$R^7$ is methyl, ethyl or propyl;
$R^9$ is $L_1$OH;
each $R^{11}$ is independently selected from —$C_1$-$C_3$alkyl;
and
$R^{12}$ is
a) —N($R^{11}$)$_2$;
b) an unsubstituted piperazinyl or an unsubstituted morpholinyl;
c) a 5-6 membered heterocycloalkyl having 1 to 2 heteroatoms independently selected from N and O substituted with =O;
d) a piperazinyl substituted with $C_1$-$C_3$alkyl or —C(=O)O$R^7$;
or
e) an unsubstituted phenyl.

6. The pharmaceutical composition of claim 3, wherein, $R^1$ is —NH$R^6$ or —NHCH$R^6R^9$;
$R^4$ is H, and $R^3$ is -$L_2$C(=O)O$R^7$, —C(=O)O$L_6R^{12}$, —C(=O)O$L_2R^{12}$, -$L_2$C(=O)O$L_2R^{12}$, -$L_4$C(=O)O$L_5$OH, -$L_4R^{12}$, -$L_2$C(=O)O$L_4$C(=O)$L_2R^{12}$, -$L_2$C(=O)O$L_6R^{12}$, -$L_2$C(=O)O$L_4$C(=O)O$L_2R^{12}$, -$L_2$C(=O)O$L_4$C(=O)$R^{12}$, -$L_4$C(=O)O$L_2$C(=O)$R^{12}$ or -$L_2$C(=O)O$L_3R^{12}$;
$R^3$ is H, and $R^4$ is —CF$_2$C(=O)$R^7$, -$L_4R^{12}$, —CH=CHC(=O)O$L_4$C(=O)$R^{12}$, —O$L_2$C(=O)O$L_4$C(=O)$R^{12}$, —O$L_4$C(=O)O$L_2R^{12}$, -$L_2$C(=O)O$R^7$, -$L_2$C(=O)O$L_4$C(=O)$R^{12}$, —O$L_4$C(=O)O$L_2$C(=O)$R^{12}$ or -$L_2$C(=O)O$L_3R^{12}$;

L₁ is —CH₂—;
L₂ is —CH₂— or —CH₂CH₂—;
L₃ is —CH₂CH₂— or —CH₂CH₂CH₂CH₂—;
L₄ is —CH₂—,
L₅ is —CH₂CH₂—,
L₆ is —(CH₂)₂O(CH₂)₂—;
R⁶ is —C₄alkyl or —C₅alkyl;
R⁷ is methyl, ethyl or propyl;
R⁹ is L₁OH;
each R¹¹ is independently selected from —C₁-C₃alkyl;
and
R¹² is
  a) —N(R¹¹)₂;
  b) an unsubstituted piperazinyl or an unsubstituted morpholinyl;
  c) a 5-6 membered heterocycloalkyl having 1 to 2 heteroatoms independently selected from N and O substituted with =O;
  d) a piperazinyl substituted with C₁-C₃alkyl or —C(=O)OR⁷;
  or
  e) an unsubstituted phenyl.

7. The pharmaceutical composition of claim 1, wherein,
R¹ is —NHR⁶;
R³ is -L₂C(=O)OL₄C(=O)R¹² and R⁴ is H;
or R³ is H and R⁴ is -L₂C(=O)OL₄C(=O)R¹²;
R⁶ is —C₄-C₆alkyl;
L₂ is —(CH₂)ₘ—;
L₄ is —(CH₂)ₘ—;
R¹² is an unsubstituted 5-6 membered heterocycloalkyl having 1 to 2 heteroatoms independently selected from N and O;
and
each m is independently selected from 1, 2, 3, and 4.

8. The pharmaceutical composition of claim 1, wherein,
R¹ is —NHR⁶;
R³ is -L₂C(=O)OL₄C(=O)L₂R¹² and R⁴ is H;
or R³ is H and R⁴ is -L₂C(=O)OL₄C(=O)L₂R¹²;
R⁶ is —C₄-C₆alkyl;
L₂ is —(CH₂)ₘ—;
L₄ is —(CH₂)ₘ—;
R¹² is an unsubstituted 5-6 membered heterocycloalkyl having 1 to 2 heteroatoms independently selected from N and O;
and
each m is independently selected from 1, 2, 3, and 4.

9. The pharmaceutical composition of claim 1, wherein,
R¹ is —NHR⁶;
R³ is -L₂C(=O)OL₄C(=O)R¹² and R⁴ is H;
or R³ is H and R⁴ is -L₂C(=O)OL₄C(=O)R¹²;
R⁶ is —C₅alkyl;
L₂ is —CH₂— or —CH₂CH₂—;
L₄ is —CH₂—,
and
R¹² is an unsubstituted piperazinyl or an unsubstituted morpholinyl.

10. The pharmaceutical composition of claim 1, wherein,
R¹ is —NHR⁶;
R³ is -L₂C(=O)OL₄C(=O)L₂R¹² and R⁴ is H;
or R³ is H and R⁴ is -L₂C(=O)OL₄C(=O)L₂R¹²;
R⁶ is —C₅alkyl;
L₂ is —CH₂— or —CH₂CH₂—;
L₄ is —CH₂—,
and
R¹² is an unsubstituted piperazinyl or an unsubstituted morpholinyl.

11. The pharmaceutical composition of claim 1, wherein,
R¹ is —NHR⁶ or —NHCHR⁶R⁹;
R³ is H and R⁴ is -L₄R¹²;
or R³ is -L₄R¹² and R⁴ is H;
L₁ is —(CH₂)ₘ—;
L₄ is —(CH₂)ₘ—;
R⁶ is —C₄-C₆alkyl;
R⁹ is L₁OH;
R¹² is an unsubstituted 5-6 membered heterocycloalkyl having 1 to 2 heteroatoms independently selected from N and O;
and
each m is independently selected from 1, 2, 3, and 4.

12. The pharmaceutical composition of claim 1, wherein,
R¹ is —NHR⁶ or —NHCHR⁶R⁹;
R³ is H and R⁴ is -L₄R¹²;
or R³ is -L₄R¹² and R⁴ is H;
L₁ is —(CH₂)—;
L₄ is —(CH₂)—;
R⁶ is —C₄alkyl or —C₅alkyl;
R⁹ is L₁OH,
and
R¹² is an unsubstituted piperazinyl.

13. The pharmaceutical composition of claim 1, wherein,
R¹ is —NHR⁶ or —NHCHR⁶R⁹;
R³ is H and R⁴ is —N(R¹¹)₂;
or R³ is —N(R¹¹)₂ and R⁴ is H;
L₁ is —(CH₂)—;
R⁶ is —C₄alkyl or —C₅alkyl;
R⁹ is L₁OH,
and
each R¹ is H.

14. The pharmaceutical composition of claim 1, wherein the compound is selected from:
  2-(dimethylamino)ethyl 4-((2-amino-4-(pentylamino)-5H-pyrrolo[3,2-d]pyrimidin-5-yl)methyl)-3-methoxybenzoate;
  2-(2-(dimethylamino)ethoxy)ethyl 4-((2-amino-4-(pentylamino)-5H-pyrrolo[3,2-d]pyrimidin-5-yl)methyl)-3-methoxybenzoate;
  methyl 2-(3-((2-amino-4-(pentylamino)-5H-pyrrolo[3,2-d]pyrimidin-5-yl)methyl)-4-methoxyphenyl)acetate;
  ethyl 3-(3-((2-amino-4-(pentylamino)-5H-pyrrolo[3,2-d]pyrimidin-5-yl)methyl)-4-methoxyphenyl)propanoate;
  methyl 2-(3-((2-amino-4-(pentylamino)-5H-pyrrolo[3,2-d]pyrimidin-5-yl)methyl)-4-methoxyphenyl)-2,2-difluoroacetate;
  2-morpholino-2-oxoethyl 2-(3-((2-amino-4-(pentylamino)-5H-pyrrolo[3,2-d]pyrimidin-5-yl)methyl)-4-methoxyphenoxy)acetate;
  2-morpholino-2-oxoethyl 2-(3-((2-amino-4-(pentylamino)-5H-pyrrolo[3,2-d]pyrimidin-5-yl)methyl)-4-methoxyphenyl)acetate;
  2-morpholino-2-oxoethyl 2-(4-((2-amino-4-(pentylamino)-5H-pyrrolo[3,2-d]pyrimidin-5-yl)methyl)-3-methoxyphenyl)acetate;
  2-(morpholin-4-yl)-2-oxoethyl 3-(4-{[2-amino-4-(pentylamino)-5H-pyrrolo[3,2-d]pyrimidin-5-yl]methyl}-3-methoxyphenyl)propanoate;
  (S)-2-morpholino-2-oxoethyl 3-(3-((2-amino-4-((1-hydroxyhexan-2-yl)amino)-5H-pyrrolo[3,2-d]pyrimidin-5-yl)methyl)-4-methoxyphenyl)propanoate;
  (S)-2-morpholino-2-oxoethyl 2-(4-((2-amino-4-((1-hydroxyhexan-2-yl)amino)-5H-pyrrolo[3,2-d]pyrimidin-5-yl)methyl)-3-methoxyphenyl)acetate;
  (S)-2-morpholino-2-oxoethyl 2-(3-((2-amino-4-((1-hydroxyhexan-2-yl)amino)-5H-pyrrolo[3,2-d]pyrimidin-5-yl)methyl)-4-methoxyphenyl)acetate;

(S)-2-morpholino-2-oxoethyl 3-(4-((2-amino-4-((1-hydroxyhexan-2-yl)amino)-5H-pyrrolo[3,2-d]pyrimidin-5-yl)methyl)-3-methoxyphenyl)propanoate;

2-(morpholin-4-yl)-2-oxoethyl (2E)-3-(3-{[2-amino-4-(pentylamino)-5H-pyrrolo[3,2-d]pyrimidin-5-yl]methyl}-4-methoxyphenyl)prop-2-enoate;

2-(morpholin-4-yl)-2-oxoethyl 3-(3-{[2-amino-4-(pentylamino)-5H-pyrrolo[3,2-d]pyrimidin-5-yl]methyl}-4-methoxyphenyl)propanoate;

2-(benzyloxy)-2-oxoethyl 2-(4-{[2-amino-4-(pentylamino)-5H-pyrrolo[3,2-d]pyrimidin-5-yl]methyl}-3-methoxyphenyl)acetate;

2-(dipropylcarbamoyl)methyl 2-(4-{[2-amino-4-(pentylamino)-5H-pyrrolo[3,2-d]pyrimidin-5-yl]methyl}-3-methoxyphenyl)acetate;

2-(dimethylamino)-2-oxoethyl 2-(4-((2-amino-4-(pentylamino)-5H-pyrrolo[3,2-d]pyrimidin-5-yl)methyl)-3-methoxyphenyl)acetate;

2-(4-methylpiperazin-1-yl)ethyl 2-(4-{[2-amino-4-(pentylamino)-5H-pyrrolo[3,2-d]pyrimidin-5-yl]methyl}-3-methoxyphenyl)acetate;

2-hydroxyethyl 2-(4-{[2-amino-4-(pentylamino)-5H-pyrrolo[3,2-d]pyrimidin-5-yl]methyl}-3-methoxyphenyl)acetate;

4-(dimethylamino)butyl 2-(4-{[2-amino-4-(pentylamino)-5H-pyrrolo[3,2-d]pyrimidin-5-yl]methyl}-3-methoxyphenyl)acetate;

2-(morpholin-4-yl)ethyl 2-(4-{[2-amino-4-(pentylamino)-5H-pyrrolo[3,2-d]pyrimidin-5-yl]methyl}-3-methoxyphenyl)acetate;

2-(piperazin-1-yl)ethyl 2-(4-{[2-amino-4-(pentylamino)-5H-pyrrolo[3,2-d]pyrimidin-5-yl]methyl}-3-methoxyphenyl)acetate;

2-(dimethylamino)ethyl 2-(3-{[2-amino-4-(pentylamino)-5H-pyrrolo[3,2-d]pyrimidin-5-yl]methyl}-4-methoxyphenoxy)acetate;

2-(piperazin-1-yl)ethyl 2-(3-{[2-amino-4-(pentylamino)-5H-pyrrolo[3,2-d]pyrimidin-5-yl]methyl}-4-methoxyphenoxy)acetate;

2-(morpholin-4-yl)ethyl 2-(3-{[2-amino-4-(pentylamino)-5H-pyrrolo[3,2-d]pyrimidin-5-yl]methyl}-4-methoxyphenoxy)acetate;

2-(4-methylpiperazin-1-yl)ethyl 2-(3-{[2-amino-4-(pentylamino)-5H-pyrrolo[3,2-d]pyrimidin-5-yl]methyl}-4-methoxyphenoxy)acetate;

(S)-2-((2-amino-5-(2-methoxy-4-(piperazin-1-ylmethyl)benzyl)-5H-pyrrolo[3,2-d]pyrimidin-4-yl)amino)hexan-1-ol;

5-(2-methoxy-4-(piperazin-1-ylmethyl)benzyl)-N4-pentyl-5H-pyrrolo[3,2-d]pyrimidine-2,4-diamine;

5-(2-methoxy-5-(piperazin-1-ylmethyl)benzyl)-N4-pentyl-5H-pyrrolo[3,2-d]pyrimidine-2,4-diamine;

(S)-2-((2-amino-5-(2-methoxy-5-(piperazin-1-ylmethyl)benzyl)-5H-pyrrolo[3,2-d]pyrimidin-4-yl)amino)hexan-1-ol, and 5-(5-amino-2-methoxybenzyl)-N4-pentyl-5H-pyrrolo[3,2-d]pyrimidine-2,4-diamine.

15. The pharmaceutical composition of claim 1, wherein the compound is selected from:

2-morpholino-2-oxoethyl 2-(3-((2-amino-4-(pentylamino)-5H-pyrrolo[3,2-d]pyrimidin-5-yl)methyl)-4-methoxyphenoxy)acetate;

2-morpholino-2-oxoethyl 2-(3-((2-amino-4-(pentylamino)-5H-pyrrolo[3,2-d]pyrimidin-5-yl)methyl)-4-methoxyphenyl)acetate;

2-morpholino-2-oxoethyl 2-(4-((2-amino-4-(pentylamino)-5H-pyrrolo[3,2-d]pyrimidin-5-yl)methyl)-3-methoxyphenyl)acetate, and 2-(morpholin-4-yl)-2-oxoethyl 3-(4-{[2-amino-4-(pentylamino)-5H-pyrrolo[3,2-d]pyrimidin-5-yl]methyl}-3-methoxyphenyl)propanoate.

16. The pharmaceutical composition of claim 1, wherein the compound is selected from:

(S)-2-((2-amino-5-(2-methoxy-4-(piperazin-1-ylmethyl)benzyl)-5H-pyrrolo[3,2-d]pyrimidin-4-yl)amino)hexan-1-ol;

5-(2-methoxy-4-(piperazin-1-ylmethyl)benzyl)-N4-pentyl-5H-pyrrolo[3,2-d]pyrimidine-2,4-diamine;

5-(2-methoxy-5-(piperazin-1-ylmethyl)benzyl)-N4-pentyl-5H-pyrrolo[3,2-d]pyrimidine-2,4-diamine;

(S)-2-((2-amino-5-(2-methoxy-5-(piperazin-1-ylmethyl)benzyl)-5H-pyrrolo[3,2-d]pyrimidin-4-yl)amino)hexan-1-ol, and 5-(5-amino-2-methoxybenzyl)-N4-pentyl-5H-pyrrolo[3,2-d]pyrimidine-2,4-diamine.

\* \* \* \* \*